US010284964B2

(12) United States Patent
Olsen et al.

(10) Patent No.: US 10,284,964 B2
(45) Date of Patent: May 7, 2019

(54) ANATOMICALLY CUSTOMIZED EAR CANAL HEARING APPARATUS

(71) Applicant: EarLens Corporation, Menlo Park, CA (US)

(72) Inventors: Jake L. Olsen, Palo Alto, CA (US); David Chazan, Palo Alto, CA (US); Jonathan P. Fay, San Mateo, CA (US); Micha Rosen, Tsur Hadass (IL); Sunil Puria, Sunnyvale, CA (US)

(73) Assignee: EarLens Corporation, Menlo Park, CA (US)

( * ) Notice: Subject to any disclaimer, the term of this patent is extended or adjusted under 35 U.S.C. 154(b) by 160 days.

(21) Appl. No.: 15/180,719

(22) Filed: Jun. 13, 2016

(65) Prior Publication Data

US 2016/0302011 A1 Oct. 13, 2016

Related U.S. Application Data

(63) Continuation of application No. 13/919,079, filed on Jun. 17, 2013, now Pat. No. 9,392,377, which is a (Continued)

(51) Int. Cl.

| | |
|---|---|
| ***A61F 2/18*** | (2006.01) |
| ***H04R 25/02*** | (2006.01) |
| ***H04R 25/00*** | (2006.01) |

(52) U.S. Cl.

CPC ........... *H04R 25/02* (2013.01); *H04R 25/606* (2013.01); *H04R 25/652* (2013.01); *H04R 2225/023* (2013.01)

(58) Field of Classification Search

CPC ......... C23C 16/01; H04R 25/65; A61F 11/08; A61F 2011/085

(Continued)

(56) References Cited

U.S. PATENT DOCUMENTS 2,763,334 A * 9/1956 Starkey ................ H04R 25/652 181/135
3,209,082 A 9/1965 McCarrell et al.
(Continued)

FOREIGN PATENT DOCUMENTS

AU 2004301961 A1 2/2005
DE 2044870 A1 3/1972
(Continued)

OTHER PUBLICATIONS

Dundas et al. The Earlens Light-Driven Hearing Aid: Top 10 questions and answers. Hearing Review. 2018;25(2):36-39.
(Continued)

*Primary Examiner* — Cachet I Sellman
(74) *Attorney, Agent, or Firm* — Wilson Sonsini Goodrich and Rosati, P.C.

(57) ABSTRACT

Embodiments of the present invention provide improved methods and apparatus suitable for use with hearing devices. A vapor deposition process can be used to make a retention structure having a shape profile corresponding to a tissue surface, such as a retention structure having a shape profile corresponding to one or more of an eardrum, the eardrum annulus, or a skin of the ear canal. The retention structure can be resilient and may comprise an anatomically accurate shape profile corresponding to a portion of the ear, such that the resilient retention structure provides mechanical stability for an output transducer assembly placed in the ear for an extended time. The output transducer may couple to the eardrum with direct mechanical coupling or acoustic coupling when retained in the ear canal with the retention structure.

24 Claims, 27 Drawing Sheets

Related U.S. Application Data continuation of application No. PCT/US2011/066306, filed on Dec. 20, 2011.

(60) Provisional application No. 61/425,000, filed on Dec. 20, 2010.

(58) Field of Classification Search
USPC .................... 264/81; 381/328; 184/129, 135
See application file for complete search history.

(56) References Cited

U.S. PATENT DOCUMENTS 3,229,049 A 1/1966 Goldberg
3,440,314 A 4/1969 Eldon
3,526,949 A * 9/1970 Genovese ........ B29D 11/00278 29/424
3,549,818 A 12/1970 Justin
3,585,416 A 6/1971 Howard
3,594,514 A 7/1971 Robert
3,710,399 A 1/1973 Hurst
3,712,962 A 1/1973 Epley
3,764,748 A 10/1973 Branch et al.
3,808,179 A 4/1974 Gaylord
3,882,285 A 5/1975 Nunley et al.
3,965,430 A 6/1976 Brandt
3,985,977 A 10/1976 Beaty et al.
4,002,897 A 1/1977 Kleinman et al.
4,031,318 A 6/1977 Pitre
4,061,972 A 12/1977 Burgess
4,075,042 A 2/1978 Das
4,098,277 A 7/1978 Mendell
4,109,116 A 8/1978 Victoreen
4,120,570 A 10/1978 Gaylord
4,248,899 A 2/1981 Lyon et al.
4,252,440 A 2/1981 Frosch et al.
4,303,772 A 12/1981 Novicky
4,319,359 A 3/1982 Wolf
4,334,315 A 6/1982 Ono et al.
4,334,321 A 6/1982 Edelman
4,338,929 A 7/1982 Lundin et al.
4,339,954 A 7/1982 Anson et al.
4,357,497 A 11/1982 Hochmair et al.
4,380,689 A 4/1983 Giannetti
4,428,377 A 1/1984 Zollner et al.
4,524,294 A 6/1985 Brody
4,540,761 A 9/1985 Kawamura et al.
4,556,122 A 12/1985 Goode
4,592,087 A 5/1986 Killion et al.
4,606,329 A 8/1986 Hough
4,611,598 A 9/1986 Hortmann et al.
4,628,907 A * 12/1986 Epley .................. H04R 25/606 381/322
4,641,377 A 2/1987 Rush et al.
4,652,414 A * 3/1987 Schlaegel ........... H04R 25/652 181/129
4,654,554 A 3/1987 Kishi
4,689,819 A 8/1987 Killion et al.
4,696,287 A 9/1987 Hortmann et al.
4,729,366 A 3/1988 Schaefer
4,741,339 A 5/1988 Harrison et al.
4,742,499 A 5/1988 Butler
4,756,312 A 7/1988 Epley
4,759,070 A 7/1988 Voroba et al.
4,766,607 A 8/1988 Feldman
4,774,933 A 10/1988 Hough et al.
4,776,322 A 10/1988 Hough et al.
4,782,818 A 11/1988 Mori
4,800,884 A 1/1989 Heide et al.
4,800,982 A 1/1989 Carlson
4,817,607 A 4/1989 Tatge
4,840,178 A 6/1989 Heide et al.
4,845,755 A 7/1989 Busch et al.
4,865,035 A 9/1989 Mori
4,870,688 A 9/1989 Voroba et al.
4,932,405 A 6/1990 Peeters et al.
4,936,305 A 6/1990 Ashtiani et al.
4,944,301 A 7/1990 Widin et al.
4,948,855 A 8/1990 Novicky
4,957,478 A 9/1990 Maniglia
4,963,963 A 10/1990 Dorman
4,999,819 A 3/1991 Newnham et al.
5,003,608 A 3/1991 Carlson
5,012,520 A 4/1991 Steeger
5,015,224 A 5/1991 Maniglia
5,015,225 A 5/1991 Hough et al.
5,031,219 A 7/1991 Ward et al.
5,061,282 A 10/1991 Jacobs
5,066,091 A 11/1991 Stoy et al.
5,068,902 A 11/1991 Ward
5,094,108 A 3/1992 Kim et al.
5,117,461 A 5/1992 Moseley
5,142,186 A 8/1992 Cross et al.
5,163,957 A 11/1992 Sade et al.
5,167,235 A 12/1992 Seacord et al.
5,201,007 A 4/1993 Ward et al.
5,259,032 A 11/1993 Perkins et al.
5,272,757 A 12/1993 Scofield et al.
5,276,910 A 1/1994 Buchele
5,277,694 A 1/1994 Leysieffer et al.
5,282,858 A 2/1994 Bisch et al.
5,360,388 A 11/1994 Spindel et al.
5,378,933 A 1/1995 Pfannenmueller et al.
5,402,496 A 3/1995 Soli et al.
5,411,467 A 5/1995 Hortmann et al.
5,425,104 A 6/1995 Shennib
5,440,082 A 8/1995 Claes
5,440,237 A 8/1995 Brown et al.
5,455,994 A 10/1995 Termeer et al.
5,456,654 A 10/1995 Ball
5,531,787 A 7/1996 Lesinski et al.
5,531,954 A 7/1996 Heide et al.
5,535,282 A 7/1996 Luca
5,554,096 A 9/1996 Ball
5,558,618 A 9/1996 Maniglia
5,572,594 A 11/1996 Devoe et al.
5,606,621 A 2/1997 Reiter et al.
5,624,376 A 4/1997 Ball et al.
5,654,530 A 8/1997 Sauer et al.
5,692,059 A 11/1997 Kruger
5,699,809 A 12/1997 Combs et al.
5,701,348 A 12/1997 Shennib et al.
5,707,338 A 1/1998 Adams et al.
5,715,321 A 2/1998 Andrea et al.
5,721,783 A 2/1998 Anderson
5,722,411 A 3/1998 Suzuki et al.
5,729,077 A 3/1998 Newnham et al.
5,740,258 A 4/1998 Goodwin-Johansson
5,749,912 A 5/1998 Zhang et al.
5,762,583 A 6/1998 Adams et al.
5,772,575 A 6/1998 Lesinski et al.
5,774,259 A 6/1998 Saitoh et al.
5,782,744 A 7/1998 Money
5,788,711 A 8/1998 Lehner et al.
5,795,287 A 8/1998 Ball et al.
5,797,834 A 8/1998 Goode
5,800,336 A 9/1998 Ball et al.
5,804,109 A 9/1998 Perkins
5,804,907 A 9/1998 Park et al.
5,814,095 A 9/1998 Mueller et al.
5,825,122 A 10/1998 Givargizov et al.
5,836,863 A 11/1998 Bushek et al.
5,842,967 A 12/1998 Kroll
5,857,958 A 1/1999 Ball et al.
5,859,916 A 1/1999 Ball et al.
5,868,682 A 2/1999 Combs et al.
5,879,283 A 3/1999 Adams et al.
5,888,187 A 3/1999 Jaeger et al.
5,897,486 A 4/1999 Ball et al.
5,899,847 A 5/1999 Adams et al.
5,900,274 A 5/1999 Chatterjee et al.
5,906,635 A 5/1999 Maniglia
5,913,815 A 6/1999 Ball et al.
5,922,077 A 7/1999 Espy et al.

(56) References Cited

U.S. PATENT DOCUMENTS 5,940,519 A 8/1999 Kuo
5,949,895 A 9/1999 Ball et al.
5,984,859 A 11/1999 Lesinski
5,987,146 A 11/1999 Pluvinage et al.
6,005,955 A 12/1999 Kroll et al.
6,024,717 A 2/2000 Ball et al.
6,045,528 A 4/2000 Arenberg et al.
6,050,933 A 4/2000 Bushek et al.
6,068,589 A 5/2000 Neukermans
6,068,590 A 5/2000 Brisken
6,084,975 A 7/2000 Perkins
6,093,144 A 7/2000 Jaeger et al.
6,135,612 A 10/2000 Clore
6,137,889 A 10/2000 Shennib et al.
6,139,488 A 10/2000 Ball
6,153,966 A 11/2000 Neukermans
6,168,948 B1 * 1/2001 Anderson ........... B01F 11/0266 366/DIG. 3
6,174,278 B1 1/2001 Jaeger et al.
6,181,801 B1 1/2001 Puthuff et al.
6,190,305 B1 2/2001 Ball et al.
6,190,306 B1 2/2001 Kennedy
6,208,445 B1 3/2001 Reime
6,217,508 B1 4/2001 Ball et al.
6,222,302 B1 4/2001 Imada et al.
6,222,927 B1 4/2001 Feng et al.
6,240,192 B1 5/2001 Brennan et al.
6,241,767 B1 6/2001 Stennert et al.
6,259,951 B1 7/2001 Kuzma et al.
6,261,224 B1 7/2001 Adams et al.
6,264,603 B1 7/2001 Kennedy
6,277,148 B1 8/2001 Dormer
6,312,959 B1 11/2001 Datskos
6,339,648 B1 1/2002 McIntosh et al.
6,354,990 B1 3/2002 Juneau et al.
6,359,993 B2 3/2002 Brimhall
6,366,863 B1 4/2002 Bye et al.
6,385,363 B1 5/2002 Rajic et al.
6,387,039 B1 5/2002 Moses
6,393,130 B1 5/2002 Stonikas et al.
6,422,991 B1 7/2002 Jaeger
6,432,248 B1 8/2002 Popp et al.
6,436,028 B1 8/2002 Dormer
6,438,244 B1 8/2002 Juneau et al.
6,445,799 B1 9/2002 Taenzer et al.
6,473,512 B1 10/2002 Juneau et al.
6,475,134 B1 11/2002 Ball et al.
6,491,644 B1 12/2002 Vujanic et al.
6,493,453 B1 12/2002 Glendon
6,493,454 B1 12/2002 Loi et al.
6,498,858 B2 12/2002 Kates
6,519,376 B2 2/2003 Biagi et al.
6,536,530 B2 3/2003 Schultz et al.
6,537,200 B2 3/2003 Leysieffer et al.
6,549,633 B1 4/2003 Westermann
6,549,635 B1 4/2003 Gebert
6,554,761 B1 4/2003 Puria et al.
6,575,894 B2 6/2003 Leysieffer et al.
6,592,513 B1 7/2003 Kroll et al.
6,603,860 B1 8/2003 Taenzer et al.
6,620,110 B2 9/2003 Schmid
6,626,822 B1 9/2003 Jaeger et al.
6,629,922 B1 10/2003 Puria et al.
6,631,196 B1 10/2003 Taenzer et al.
6,663,575 B2 12/2003 Leysieffer
6,668,062 B1 12/2003 Luo et al.
6,676,592 B2 1/2004 Ball et al.
6,681,022 B1 1/2004 Puthuff et al.
6,695,943 B2 2/2004 Juneau et al.
6,697,674 B2 2/2004 Leysieffer
6,724,902 B1 4/2004 Shennib et al.
6,726,618 B2 4/2004 Miller
6,726,718 B1 4/2004 Carlyle et al.
6,727,789 B2 4/2004 Tibbetts et al.
6,728,024 B2 4/2004 Ribak
6,735,318 B2 5/2004 Cho
6,754,358 B1 6/2004 Boesen et al.
6,754,359 B1 6/2004 Svean et al.
6,754,537 B1 6/2004 Harrison et al.
6,785,394 B1 8/2004 Olsen et al.
6,801,629 B2 10/2004 Brimhall et al.
6,829,363 B2 12/2004 Sacha
6,837,857 B2 1/2005 Stirnemann
6,842,647 B1 1/2005 Griffith et al.
6,888,949 B1 5/2005 Vanden et al.
6,900,926 B2 5/2005 Ribak
6,912,289 B2 6/2005 Vonlanthen et al.
6,920,340 B2 7/2005 Laderman
6,931,231 B1 8/2005 Griffin
6,940,988 B1 9/2005 Shennib et al.
6,940,989 B1 9/2005 Shennib et al.
D512,979 S 12/2005 Corcoran et al.
6,975,402 B2 12/2005 Bisson et al.
6,978,159 B2 12/2005 Feng et al.
7,043,037 B2 5/2006 Lichtblau et al.
7,050,675 B2 5/2006 Zhou et al.
7,050,876 B1 5/2006 Fu et al.
7,057,256 B2 6/2006 Mazur et al.
7,058,182 B2 6/2006 Kates
7,072,475 B1 7/2006 Denap et al.
7,076,076 B2 7/2006 Bauman
7,095,981 B1 8/2006 Voroba et al.
7,167,572 B1 1/2007 Harrison et al.
7,174,026 B2 2/2007 Niederdrank et al.
7,203,331 B2 4/2007 Boesen
7,239,069 B2 7/2007 Cho
7,245,732 B2 7/2007 Jorgensen et al.
7,255,457 B2 8/2007 Ducharme et al.
7,266,208 B2 9/2007 Charvin et al.
7,289,639 B2 10/2007 Abel et al.
7,313,245 B1 12/2007 Shennib
7,322,930 B2 1/2008 Jaeger et al.
7,349,741 B2 3/2008 Maltan et al.
7,354,792 B2 4/2008 Mazur et al.
7,376,563 B2 5/2008 Leysieffer et al.
7,390,689 B2 6/2008 Mazur et al.
7,394,909 B1 7/2008 Widmer et al.
7,421,087 B2 9/2008 Perkins et al.
7,424,122 B2 9/2008 Ryan
7,444,877 B2 11/2008 Li et al.
7,547,275 B2 6/2009 Cho et al.
7,630,646 B2 12/2009 Anderson et al.
7,668,325 B2 2/2010 Puria et al.
7,747,295 B2 6/2010 Choi
7,826,632 B2 11/2010 Von et al.
7,853,033 B2 12/2010 Maltan et al.
7,867,160 B2 1/2011 Pluvinage et al.
7,983,435 B2 7/2011 Moses
8,090,134 B2 1/2012 Takigawa et al.
8,116,494 B2 2/2012 Rass
8,128,551 B2 3/2012 Jolly
8,157,730 B2 4/2012 Leboeuf et al.
8,197,461 B1 6/2012 Arenberg et al.
8,204,786 B2 6/2012 Leboeuf et al.
8,233,651 B1 7/2012 Haller
8,251,903 B2 8/2012 Leboeuf et al.
8,295,505 B2 10/2012 Weinans et al.
8,295,523 B2 10/2012 Fay et al.
8,320,601 B2 11/2012 Takigawa et al.
8,320,982 B2 11/2012 Leboeuf et al.
8,340,335 B1 12/2012 Shennib
8,391,527 B2 3/2013 Feucht et al.
8,396,239 B2 3/2013 Fay et al.
8,401,212 B2 3/2013 Puria et al.
8,506,473 B2 8/2013 Puria
8,512,242 B2 8/2013 Leboeuf et al.
8,526,651 B2 9/2013 Van et al.
8,545,383 B2 10/2013 Wenzel et al.
8,600,089 B2 12/2013 Wenzel et al.
8,647,270 B2 2/2014 Leboeuf et al.
8,652,040 B2 2/2014 Leboeuf et al.
8,696,054 B2 4/2014 Crum
8,696,541 B2 4/2014 Pluvinage et al.
8,700,111 B2 4/2014 Leboeuf et al.

(56) References Cited

U.S. PATENT DOCUMENTS

| | | | |
|---|---|---|---|
| 8,702,607 B2 | 4/2014 | Leboeuf et al. | |
| 8,715,152 B2 | 5/2014 | Puria et al. | |
| 8,715,153 B2 | 5/2014 | Puria et al. | |
| 8,715,154 B2 | 5/2014 | Perkins et al. | |
| 8,761,423 B2 | 6/2014 | Wagner et al. | |
| 8,788,002 B2 | 7/2014 | Leboeuf et al. | |
| 8,824,715 B2 | 9/2014 | Fay et al. | |
| 8,855,323 B2 | 10/2014 | Kroman | |
| 8,858,419 B2 | 10/2014 | Puria et al. | |
| 8,885,860 B2 | 11/2014 | Djalilian et al. | |
| 8,886,269 B2 | 11/2014 | Leboeuf et al. | |
| 8,888,701 B2 | 11/2014 | Leboeuf et al. | |
| 8,923,941 B2 | 12/2014 | Leboeuf et al. | |
| 8,929,965 B2 | 1/2015 | Leboeuf et al. | |
| 8,929,966 B2 | 1/2015 | Leboeuf et al. | |
| 8,934,952 B2 | 1/2015 | Leboeuf et al. | |
| 8,942,776 B2 | 1/2015 | Leboeuf et al. | |
| 8,961,415 B2 | 2/2015 | Leboeuf et al. | |
| 8,989,830 B2 | 3/2015 | Leboeuf et al. | |
| 9,044,180 B2 | 6/2015 | Leboeuf et al. | |
| 9,049,528 B2 | 6/2015 | Fay et al. | |
| 9,131,312 B2 | 9/2015 | Leboeuf et al. | |
| 9,154,891 B2 | 10/2015 | Puria et al. | |
| 9,211,069 B2 | 12/2015 | Larsen et al. | |
| 9,226,083 B2 | 12/2015 | Puria et al. | |
| 9,289,135 B2 | 3/2016 | Leboeuf et al. | |
| 9,289,175 B2 | 3/2016 | Leboeuf et al. | |
| 9,301,696 B2 | 4/2016 | Leboeuf et al. | |
| 9,314,167 B2 | 4/2016 | Leboeuf et al. | |
| 9,392,377 B2 | 7/2016 | Olsen et al. | |
| 9,427,191 B2 | 8/2016 | Leboeuf et al. | |
| 9,521,962 B2 | 12/2016 | Leboeuf | |
| 9,538,921 B2 | 1/2017 | Leboeuf et al. | |
| 9,544,700 B2 | 1/2017 | Puria et al. | |
| 9,749,758 B2 | 8/2017 | Puria et al. | |
| 9,750,462 B2 | 9/2017 | Leboeuf et al. | |
| 9,788,785 B2 | 10/2017 | Leboeuf | |
| 9,788,794 B2 | 10/2017 | Leboeuf et al. | |
| 9,794,653 B2 | 10/2017 | Aumer et al. | |
| 9,801,552 B2 | 10/2017 | Romesburg et al. | |
| 9,808,204 B2 | 11/2017 | Leboeuf et al. | |
| 9,949,045 B2 * | 4/2018 | Kure .................... | H04R 25/652 |
| 2001/0003788 A1 | 6/2001 | Ball et al. | |
| 2001/0007050 A1 | 7/2001 | Adelman | |
| 2001/0024507 A1 | 9/2001 | Boesen | |
| 2001/0027342 A1 | 10/2001 | Dormer | |
| 2001/0043708 A1 | 11/2001 | Brimhall | |
| 2001/0053871 A1 | 12/2001 | Zilberman et al. | |
| 2002/0012438 A1 | 1/2002 | Leysieffer et al. | |
| 2002/0029070 A1 | 3/2002 | Leysieffer et al. | |
| 2002/0030871 A1 | 3/2002 | Anderson et al. | |
| 2002/0035309 A1 | 3/2002 | Leysieffer | |
| 2002/0085728 A1 | 7/2002 | Shennib et al. | |
| 2002/0086715 A1 | 7/2002 | Sahagen | |
| 2002/0172350 A1 | 11/2002 | Edwards et al. | |
| 2002/0183587 A1 | 12/2002 | Dormer | |
| 2003/0021903 A1 | 1/2003 | Shlenker et al. | |
| 2003/0064746 A1 | 4/2003 | Rader et al. | |
| 2003/0081803 A1 | 5/2003 | Petilli et al. | |
| 2003/0097178 A1 | 5/2003 | Roberson et al. | |
| 2003/0125602 A1 | 7/2003 | Sokolich et al. | |
| 2003/0142841 A1 | 7/2003 | Wiegand | |
| 2003/0208099 A1 | 11/2003 | Ball | |
| 2003/0208888 A1 | 11/2003 | Fearing et al. | |
| 2004/0019294 A1 | 1/2004 | Stirnemann | |
| 2004/0121291 A1 * | 6/2004 | Knapp ............... | A61C 13/0006 433/218 |
| 2004/0165742 A1 | 8/2004 | Shennib et al. | |
| 2004/0166495 A1 | 8/2004 | Greinwald et al. | |
| 2004/0167377 A1 | 8/2004 | Schafer et al. | |
| 2004/0184732 A1 | 9/2004 | Zhou et al. | |
| 2004/0202339 A1 | 10/2004 | O'Brien et al. | |
| 2004/0202340 A1 | 10/2004 | Armstrong et al. | |
| 2004/0208333 A1 | 10/2004 | Cheung et al. | |
| 2004/0234089 A1 | 11/2004 | Rembrand et al. | |
| 2004/0234092 A1 | 11/2004 | Wada et al. | |
| 2004/0236416 A1 | 11/2004 | Falotico | |
| 2004/0240691 A1 | 12/2004 | Grafenberg | |
| 2005/0018859 A1 | 1/2005 | Buchholz | |
| 2005/0020873 A1 | 1/2005 | Berrang et al. | |
| 2005/0036639 A1 | 2/2005 | Bachler et al. | |
| 2005/0038498 A1 | 2/2005 | Dubrow et al. | |
| 2005/0088435 A1 | 4/2005 | Geng | |
| 2005/0101830 A1 | 5/2005 | Easter et al. | |
| 2005/0163333 A1 | 7/2005 | Abel et al. | |
| 2005/0226446 A1 | 10/2005 | Luo et al. | |
| 2005/0271870 A1 | 12/2005 | Jackson | |
| 2006/0015155 A1 | 1/2006 | Charvin et al. | |
| 2006/0023908 A1 | 2/2006 | Perkins et al. | |
| 2006/0058573 A1 | 3/2006 | Neisz et al. | |
| 2006/0062420 A1 | 3/2006 | Araki | |
| 2006/0074159 A1 | 4/2006 | Lu et al. | |
| 2006/0075175 A1 | 4/2006 | Jensen et al. | |
| 2006/0107744 A1 | 5/2006 | Li et al. | |
| 2006/0161255 A1 | 7/2006 | Zarowski et al. | |
| 2006/0177079 A1 | 8/2006 | Baekgaard et al. | |
| 2006/0177082 A1 * | 8/2006 | Solomito, Jr. .......... | A61F 11/08 381/322 |
| 2006/0183965 A1 | 8/2006 | Kasic et al. | |
| 2006/0189841 A1 | 8/2006 | Pluvinage et al. | |
| 2006/0231914 A1 | 10/2006 | Carey, III | |
| 2006/0233398 A1 | 10/2006 | Husung | |
| 2006/0237126 A1 | 10/2006 | Guffrey et al. | |
| 2006/0247735 A1 | 11/2006 | Honert et al. | |
| 2006/0251278 A1 | 11/2006 | Puria et al. | |
| 2006/0256989 A1 | 11/2006 | Olsen et al. | |
| 2006/0278245 A1 | 12/2006 | Gan | |
| 2007/0030990 A1 | 2/2007 | Fischer | |
| 2007/0036377 A1 | 2/2007 | Stirnemann | |
| 2007/0076913 A1 | 4/2007 | Schanz | |
| 2007/0083078 A1 | 4/2007 | Easter et al. | |
| 2007/0100197 A1 | 5/2007 | Perkins et al. | |
| 2007/0127748 A1 | 6/2007 | Carlile et al. | |
| 2007/0127752 A1 | 6/2007 | Armstrong | |
| 2007/0127766 A1 | 6/2007 | Combest | |
| 2007/0135870 A1 | 6/2007 | Shanks et al. | |
| 2007/0161848 A1 | 7/2007 | Dalton et al. | |
| 2007/0191673 A1 | 8/2007 | Ball et al. | |
| 2007/0206825 A1 | 9/2007 | Thomasson | |
| 2007/0225776 A1 | 9/2007 | Fritsch et al. | |
| 2007/0236704 A1 | 10/2007 | Carr et al. | |
| 2007/0250119 A1 | 10/2007 | Tyler et al. | |
| 2007/0251082 A1 | 11/2007 | Milojevic et al. | |
| 2007/0286429 A1 | 12/2007 | Grafenberg et al. | |
| 2008/0021518 A1 | 1/2008 | Hochmair et al. | |
| 2008/0051623 A1 | 2/2008 | Schneider et al. | |
| 2008/0054509 A1 | 3/2008 | Berman et al. | |
| 2008/0063228 A1 | 3/2008 | Mejia et al. | |
| 2008/0063231 A1 | 3/2008 | Juneau et al. | |
| 2008/0064918 A1 | 3/2008 | Jolly | |
| 2008/0089292 A1 | 4/2008 | Kitazoe et al. | |
| 2008/0107292 A1 | 5/2008 | Kornagel | |
| 2008/0123866 A1 | 5/2008 | Rule et al. | |
| 2008/0188707 A1 | 8/2008 | Bernard et al. | |
| 2008/0298600 A1 | 12/2008 | Poe et al. | |
| 2008/0300703 A1 | 12/2008 | Widmer et al. | |
| 2009/0023976 A1 | 1/2009 | Cho et al. | |
| 2009/0043149 A1 | 2/2009 | Abel et al. | |
| 2009/0076581 A1 | 3/2009 | Gibson | |
| 2009/0092271 A1 | 4/2009 | Fay et al. | |
| 2009/0097681 A1 | 4/2009 | Puria et al. | |
| 2009/0141919 A1 | 6/2009 | Spitaels et al. | |
| 2009/0149697 A1 | 6/2009 | Steinhardt et al. | |
| 2009/0253951 A1 | 10/2009 | Ball et al. | |
| 2009/0262966 A1 | 10/2009 | Vestergaard et al. | |
| 2009/0281367 A1 | 11/2009 | Cho et al. | |
| 2009/0310805 A1 | 12/2009 | Petroff | |
| 2010/0034409 A1 | 2/2010 | Fay et al. | |
| 2010/0036488 A1 | 2/2010 | De, Jr. et al. | |
| 2010/0048982 A1 | 2/2010 | Puria et al. | |
| 2010/0085176 A1 | 4/2010 | Flick | |
| 2010/0111315 A1 | 5/2010 | Kroman | |
| 2010/0152527 A1 | 6/2010 | Puria | |
| 2010/0177918 A1 | 7/2010 | Keady et al. | |

(56) References Cited

U.S. PATENT DOCUMENTS

| | | | | |
|---|---|---|---|---|
| 2010/0202645 | A1 | 8/2010 | Puria et al. | |
| 2010/0222639 | A1 | 9/2010 | Purcell et al. | |
| 2010/0272299 | A1 | 10/2010 | Van et al. | |
| 2010/0290653 | A1 | 11/2010 | Wiggins et al. | |
| 2010/0312040 | A1 | 12/2010 | Puria et al. | |
| 2011/0069852 | A1 | 3/2011 | Arndt et al. | |
| 2011/0077453 | A1 | 3/2011 | Pluvinage et al. | |
| 2011/0112462 | A1 | 5/2011 | Parker et al. | |
| 2011/0116666 | A1 | 5/2011 | Dittberner et al. | |
| 2011/0130622 | A1 | 6/2011 | Ilberg et al. | |
| 2011/0144414 | A1 | 6/2011 | Spearman et al. | |
| 2011/0152602 | A1 | 6/2011 | Perkins et al. | |
| 2011/0182453 | A1 | 7/2011 | Van et al. | |
| 2011/0221391 | A1 | 9/2011 | Won et al. | |
| 2011/0258839 | A1 | 10/2011 | Probst | |
| 2012/0008807 | A1 | 1/2012 | Gran | |
| 2012/0014546 | A1 | 1/2012 | Puria et al. | |
| 2012/0038881 | A1* | 2/2012 | Amirparviz .............. | G02C 7/04<br>351/159.02 |
| 2012/0039493 | A1 | 2/2012 | Rucker et al. | |
| 2012/0140967 | A1 | 6/2012 | Aubert et al. | |
| 2012/0236524 | A1 | 9/2012 | Pugh et al. | |
| 2013/0004004 | A1* | 1/2013 | Zhao ................... | H04R 25/656<br>381/328 |
| 2013/0034258 | A1 | 2/2013 | Lin | |
| 2013/0083938 | A1 | 4/2013 | Bakalos et al. | |
| 2013/0287239 | A1 | 10/2013 | Fay et al. | |
| 2013/0308782 | A1 | 11/2013 | Dittberner et al. | |
| 2013/0343584 | A1 | 12/2013 | Bennett et al. | |
| 2013/0343585 | A1 | 12/2013 | Bennett et al. | |
| 2014/0003640 | A1 | 1/2014 | Puria et al. | |
| 2014/0056453 | A1 | 2/2014 | Olsen et al. | |
| 2014/0153761 | A1 | 6/2014 | Shennib et al. | |
| 2014/0169603 | A1 | 6/2014 | Sacha et al. | |
| 2014/0254856 | A1 | 9/2014 | Blick et al. | |
| 2014/0286514 | A1 | 9/2014 | Pluvinage et al. | |
| 2014/0288356 | A1 | 9/2014 | Van | |
| 2014/0296620 | A1 | 10/2014 | Puria et al. | |
| 2014/0321657 | A1 | 10/2014 | Stirnemann | |
| 2014/0379874 | A1 | 12/2014 | Starr et al. | |
| 2015/0023540 | A1 | 1/2015 | Fay et al. | |
| 2015/0031941 | A1 | 1/2015 | Perkins et al. | |
| 2015/0201269 | A1 | 7/2015 | Dahl et al. | |
| 2015/0222978 | A1 | 8/2015 | Murozaki et al. | |
| 2015/0271609 | A1 | 9/2015 | Puria | |
| 2016/0029132 | A1 | 1/2016 | Freed et al. | |
| 2016/0064814 | A1 | 3/2016 | Jang et al. | |
| 2016/0066101 | A1 | 3/2016 | Puria et al. | |
| 2016/0134976 | A1 | 5/2016 | Puria et al. | |
| 2016/0150331 | A1 | 5/2016 | Wenzel | |
| 2016/0183017 | A1 | 6/2016 | Rucker et al. | |
| 2016/0309266 | A1 | 10/2016 | Olsen et al. | |
| 2017/0095167 | A1 | 4/2017 | Facteau et al. | |
| 2017/0095202 | A1 | 4/2017 | Facteau et al. | |
| 2017/0134866 | A1 | 5/2017 | Puria et al. | |
| 2017/0150275 | A1 | 5/2017 | Puria et al. | |
| 2017/0195801 | A1 | 7/2017 | Rucker et al. | |
| 2017/0195804 | A1 | 7/2017 | Sandhu et al. | |
| 2017/0195806 | A1 | 7/2017 | Atamaniuk et al. | |
| 2017/0195809 | A1 | 7/2017 | Teran et al. | |
| 2018/0007472 | A1 | 1/2018 | Puria et al. | |
| 2018/0014128 | A1 | 1/2018 | Puria et al. | |
| 2018/0020291 | A1 | 1/2018 | Puria et al. | |
| 2018/0020296 | A1 | 1/2018 | Wenzel | |
| 2018/0063652 | A1 | 3/2018 | Perkins et al. | |
| 2018/0077503 | A1 | 3/2018 | Shaquer et al. | |
| 2018/0167750 | A1 | 6/2018 | Freed et al. | |
| 2018/0213331 | A1 | 7/2018 | Rucker et al. | |
| 2018/0213335 | A1 | 7/2018 | Puria et al. | |
| 2018/0262846 | A1 | 9/2018 | Perkins et al. | |

FOREIGN PATENT DOCUMENTS

| | | | |
|---|---|---|---|
| DE | 3243850 | A1 | 5/1984 |
| DE | 3508830 | A1 | 9/1986 |
| EP | 0092822 | A2 | 11/1983 |
| EP | 0242038 | A2 | 10/1987 |
| EP | 0291325 | A2 | 11/1988 |
| EP | 0296092 | A2 | 12/1988 |
| EP | 0242038 | A3 | 5/1989 |
| EP | 0296092 | A3 | 8/1989 |
| EP | 0352954 | A2 | 1/1990 |
| EP | 0291325 | A3 | 6/1990 |
| EP | 0352954 | A3 | 8/1991 |
| EP | 1845919 | A1 | 10/2007 |
| EP | 1845919 | B1 | 9/2010 |
| FR | 2455820 | A1 | 11/1980 |
| JP | S60154800 | A | 8/1985 |
| JP | H09327098 | A | 12/1997 |
| JP | 2000504913 | A | 4/2000 |
| JP | 2004187953 | A | 7/2004 |
| KR | 100624445 | B1 | 9/2006 |
| WO | WO-9209181 | A1 | 5/1992 |
| WO | WO-9621334 | A1 | 7/1996 |
| WO | WO-9736457 | A1 | 10/1997 |
| WO | WO-9745074 | A1 | 12/1997 |
| WO | WO-9806236 | A1 | 2/1998 |
| WO | WO-9903146 | A1 | 1/1999 |
| WO | WO-9915111 | A1 | 4/1999 |
| WO | WO-0022875 | A2 | 4/2000 |
| WO | WO-0022875 | A3 | 7/2000 |
| WO | WO-0150815 | A1 | 7/2001 |
| WO | WO-0158206 | A2 | 8/2001 |
| WO | WO-0176059 | A2 | 10/2001 |
| WO | WO-0158206 | A3 | 2/2002 |
| WO | WO-0239874 | A2 | 5/2002 |
| WO | WO-0239874 | A3 | 2/2003 |
| WO | WO-03063542 | A2 | 7/2003 |
| WO | WO-03063542 | A3 | 1/2004 |
| WO | WO-2004010733 | A1 | 1/2004 |
| WO | WO-2005015952 | A1 | 2/2005 |
| WO | WO-2005107320 | A1 | 11/2005 |
| WO | WO-2006014915 | A2 | 2/2006 |
| WO | WO-2006037156 | A1 | 4/2006 |
| WO | WO-2006042298 | A2 | 4/2006 |
| WO | WO-2006075169 | A1 | 7/2006 |
| WO | WO-2006075175 | A1 | 7/2006 |
| WO | WO-2006118819 | A2 | 11/2006 |
| WO | WO-2006042298 | A3 | 12/2006 |
| WO | WO-2009046329 | A1 | 4/2009 |
| WO | WO-2009047370 | A2 | 4/2009 |
| WO | WO-2009049320 | A1 | 4/2009 |
| WO | WO-2009056167 | A1 | 5/2009 |
| WO | WO-2009047370 | A3 | 7/2009 |
| WO | WO-2009145842 | A2 | 12/2009 |
| WO | WO-2009146151 | A2 | 12/2009 |
| WO | WO-2009155358 | A1 | 12/2009 |
| WO | WO-2009155361 | A1 | 12/2009 |
| WO | WO-2010033932 | A1 | 3/2010 |
| WO | WO-2010033933 | A1 | 3/2010 |
| WO | WO-2010077781 | A2 | 7/2010 |
| WO | WO-2012088187 | A2 | 6/2012 |
| WO | WO-2012149970 | A1 | 11/2012 |
| WO | WO-2016011044 | A1 | 1/2016 |
| WO | WO-2017059218 | A1 | 4/2017 |
| WO | WO-2017059240 | A1 | 4/2017 |
| WO | WO-2017116791 | A1 | 7/2017 |
| WO | WO-2017116865 | A1 | 7/2017 |
| WO | WO-2018081121 | A1 | 5/2018 |

OTHER PUBLICATIONS

Khaleghi et al. Attenuating the ear canal feedback pressure of a laser-driven hearing aid. J Acoust Soc Am. Mar. 2017;141(3):1683.

Khaleghi et al. Attenuating the feedback pressure of a light-activated hearing device to allows microphone placement at the ear canal entrance. IHCON 2016, International Hearing Aid Research Conference, Tahoe City, CA, Aug. 2016.

(56) References Cited

OTHER PUBLICATIONS

Khaleghi et al. Mechano-Electro-Magnetic Finite Element Model of a Balanced Armature Transducer for a Contact Hearing Aid. Proc. MoH 2017, Mechanics of Hearing workshop, Brock University, Jun. 2017.
Khaleghi et al. Multiphysics Finite Element Model of a Balanced Armature Transducer used in a Contact Hearing Device. ARO 2017, 40th ARO MidWinter Meeting, Baltimore, MD, Feb. 2017.
Levy et al. Light-driven contact hearing aid: a removable direct-drive hearing device option for mild to severe sensorineural hearing impairment. Conference on Implantable Auditory Prostheses, Tahoe City, CA, Jul. 2017. 1 page.
McElveen et al. Overcoming High-Frequency Limitations of Air Conduction Hearing Devices Using a Light-Driven Contact Hearing Aid. Poster presentation at The Triological Society, 120th Annual Meeting at COSM, Apr. 28, 2017; San Diego, CA.
Park, et al. Design and analysis of a microelectromagnetic vibration transducer used as an implantable middle ear hearing aid. J. Micromech. Microeng. vol. 12 (2002), pp. 505-511.
Asbeck, et al. Scaling Hard Vertical Surfaces with Compliant Microspine Arrays, The International Journal of Robotics Research 2006; 25; 1165-79.
Autumn, et al. Dynamics of geckos running vertically, The Journal of Experimental Biology 209, 260-272, (2006).
Autumn, et al., Evidence for van der Waals adhesion in gecko setae, www.pnas.orgycgiyodiy10.1073ypnas.192252799 (2002).
Boedts. Tympanic epithelial migration, Clinical Otolaryngology 1978, 3, 249-253.
Cheng; et al., "A silicon microspeaker for hearing instruments. Journal of Micromechanics and Microengineering 14, No. 7 (2004): 859-866.".
Fay. Cat eardrum mechanics. Ph.D. thesis. Disseration submitted to Department of Aeronautics and Astronautics. Standford University. May 2001; 210 pages total.
Fay, et al. The discordant eardrum, PNAS, Dec. 26, 2006, vol. 103, No. 52, p. 19743-19748.
Gantz, et al. Light-Driven Contact Hearing Aid for Broad-Spectrum Amplification: Safety and Effectiveness Pivotal Study. Otology & Neurotology. Copyright 2016. 7 pages.
Ge, et al., Carbon nanotube-based synthetic gecko tapes, p. 10792-10795, PNAS, Jun. 26, 2007, vol. 104, No. 26.
Gorb, et al. Structural Design and Biomechanics of Friction-Based Releasable Attachment Devices in Insects, INTEGR. COMP_ BIOL., 42:1127-1139 (2002).
Izzo, et al. Laser Stimulation of Auditory Neurons: Effect of Shorter Pulse Duration and Penetration Depth. Biophys J. Apr. 15, 2008;94(8):3159-3166.
Izzo, et al. Laser Stimulation of the Auditory Nerve. Lasers Surg Med. Sep. 2006;38(8):745-753.
Izzo, et al. Selectivity of Neural Stimulation in the Auditory System: A Comparison of Optic and Electric Stimuli. J Biomed Opt. Mar.-Apr. 2007;12(2):021008.
Makino, et al. Epithelial migration in the healing process of tympanic membrane perforations. Eur Arch Otorhinolaryngol. 1990; 247: 352-355.
Makino, et al., Epithelial migration on the tympanic membrane and external canal, Arch Otorhinolaryngol (1986) 243:39-42.
Markoff. Intuition + Money: An Aha Moment. New York Times Oct. 11, 2008, p. BU4, 3 pages total.
Michaels, et al., Auditory Epithelial Migration on the Human Tympanic Membrane: II. The Existence of Two Discrete Migratory Pathways and Their Embryologic Correlates, The American Journal of Anatomy 189:189-200 (1990).
Murphy M, Aksak B, Sitti M. Adhesion and anisotropic friction enhancements of angled heterogeneous micro-fiber arrays with spherical and spatula tips. J Adhesion Sci Technol, vol. 21, No. 12-13, p. 1281-1296, 2007.
Nishihara, et al. Effect of changes in mass on middle ear function. Otolaryngol Head Neck Surg. Nov. 1993;109(5):889-910.
Puria, et al., Mechano-Acoustical Transformations in A. Basbaum et al., eds., The Senses: A Comprehensive Reference, v3, p. 165-202, Academic Press (2008).
Qu, et al. Carbon Nanotube Arrays with Strong Shear Binding-On and Easy Normal Lifting-Off, Oct. 10, 2008 vol. 322 Science. 238-242.
Roush. SiOnyx Brings "Black Silicon" into the Light; Material Could Upend Solar, Imaging Industries. Xconomy, Oct. 12, 2008, retrieved from the Internet: www.xconomy.com/boston/2008/10/12/sionyx-brings-black-silicon-into-the-light-material-could-upend-solar-imaging-industries> 4 pages total.
R.P. Jackson, C. Chlebicki, T.B. Krasieva, R. Zalpuri, W.J. Triffo, S. Puria, "Multiphoton and Transmission Electron Microscopy of Collagen in Ex Vivo Tympanic Membranes," Biomedcal Computation at STandford, Oct. 2008.
Rubinstein. How Cochlear Implants Encode Speech, Curr Opin Otolaryngol Head Neck Surg. Oct. 2004;12(5):444-8; retrieved from the Internet: www.ohsu.edu/nod/documents/week3/Rubenstein.pdf.
Spolenak, et al. Effects of contact shape on the scaling of biological attachments. Proc. R. Soc. A. 2005; 461:305-319.
Stenfelt, et al. Bone-Conducted Sound: Physiological and Clinical Aspects. Otology & Neurotology, Nov. 2005; 26 (6):1245-1261.
Struck, et al. Comparison of Real-world Bandwidth in Hearing Aids vs Earlens Light-driven Hearing Aid System. The Hearing Review. TechTopic: EarLens. Hearingreview.com. Mar. 14, 2017. pp. 24-28.
The Scientist and Engineers Guide to Digital Signal Processing, copyright 01997-1998 by Steven W. Smith, available online at www.DSPguide.com.
Vinikman-Pinhasi, et al. Piezoelectric and Piezooptic Effects in Porous Silicon. Applied Physics Letters, Mar. 2006; 88(11): 11905-111906.
Yao, et al. Adhesion and sliding response of a biologically inspired fibrillar surface: experimental observations, J. R. Soc. Interface (2008) 5, 723-733 doi:10.1098/rsif.2007.1225 Published online Oct. 30, 2007.
Yao, et al. Maximum strength for intermolecular adhesion of nanospheres at an optimal size. J. R. Soc. Interface doi:10.10981rsif.2008.0066 Published online 2008.
Atasoy [Paper] Opto-acoustic Imaging. for BYM504E Biomedical Imaging Systems class at ITU, downloaded from the Internet www2.itu.edu.td-cilesiz/courses/BYM504- 2005-OA504041413.pdf, 14 pages.
Athanassiou, et al. Laser controlled photomechanical actuation of photochromic polymers Microsystems. Rev. Adv. Mater. Sci. 2003; 5:245-251.
Ayatollahi, et al. Design and Modeling of Micromachined Condenser MEMS Loudspeaker using Permanent Magnet Neodymium-Iron-Boron (Nd—Fe—B). IEEE International Conference on Semiconductor Electronics, 2006. ICSE '06, Oct. 29, 2006-Dec. 1, 2006; 160-166.
Baer, et al. Effects of Low Pass Filtering on the Intelligibility of Speech in Noise for People With and Without Dead Regions at High Frequencies. J. Acost. Soc. Am 112 (3), pt. 1, (Sep. 2002), pp. 1133-1144.
Best, et al. The influence of high frequencies on speech localization. Abstract 981 (Feb. 24, 2003) from www.aro.org/abstracts/abstracts.html.
Birch, et al. Microengineered systems for the hearing impaired. IEE Colloquium on Medical Applications of Microengineering, Jan. 31, 1996; pp. 2/1-2/5.
Burkhard, et al. Anthropometric Manikin for Acoustic Research. J. Acoust. Soc. Am., vol. 58, No. 1, (Jul. 1975), pp. 214-222.
Camacho-Lopez, et al. Fast Liquid Crystal Elastomer Swims Into the Dark, Electronic Liquid Crystal Communications. Nov. 26, 2003; 9 pages total.
Carlile, et al. Frequency bandwidth and multi-talker environments. Audio Engineering Society Convention 120. Audio Engineering Society, May 20-23, 2006. Paris, France. 118: 8 pages.
Carlile, et al. Spatialisation of talkers and the segregation of concurrent speech. Abstract 1264 (Feb. 24, 2004) from www.aro.org/abstracts/abstracts.html.

(56) References Cited

OTHER PUBLICATIONS

Cheng, et al. A Silicon Microspeaker for Hearing Instruments. Journal of Micromechanics and Microengineering 2004; 14(7):859-866.
Co-pending U.S. Appl. No. 14/949,495, filed Nov. 23, 2015.
Co-pending U.S. Appl. No. 15/187,407, filed Jun. 20, 2016.
Datskos, et al. Photoinduced and thermal stress in silicon microcantilevers. Applied Physics Letters. Oct. 19, 1998; 73(16):2319-2321.
Decraemer, et al. A method for determining three-dimensional vibration in the ear. Hearing Res., 77:19-37 (1994).
Ear. Retrieved from the Internet: http://wwwmgs.bionet.nsc.ru/mgs/gnw/trrd/thesaurus/Se/ear.html. Accessed Jun. 17, 2008.
Fay, et al. Cat eardrum response mechanics. Mechanics and Computation Division. Department of Mechanical Engineering. Standford University. 2002; 10 pages total.
Fay, et al. Preliminary evaluation of a light-based contact hearing device for the hearing impaired. Otol Neurotol. Jul. 2013;34(5):912-21. doi: 10.1097/MAO.0b013e31827de4b1.
Fletcher. Effects of Distortion on the Individual Speech Sounds. Chapter 18, ASA Edition of Speech and Hearing in Communication, Acoust Soc.of Am. (republished in 1995) pp. 415-423.
Freyman, et al. Spatial Release from Informational Masking in Speech Recognition. J. Acost. Soc. Am., vol. 109, No. 5, pt. 1, (May 2001); 2112-2122.
Freyman, et al. The Role of Perceived Spatial Separation in the Unmasking of Speech. J. Acoust. Soc. Am., vol. 106, No. 6, (Dec. 1999); 3578-3588.
Fritsch, et al. EarLens transducer behavior in high-field strength MRI scanners. Otolaryngol Head Neck Surg. Mar. 2009;140(3):426-8. doi: 10.1016/j.otohns.2008.10.016.
Gantz, et al. Broad Spectrum Amplification with a Light Driven Hearing System. Combined Otolaryngology Spring Meetings, 2016 (Chicago).
Gantz, et al. Light Driven Hearing Aid: A Multi-Center Clinical Study. Association for Research in Otolaryngology Annual Meeting, 2016 (San Diego).
Gantz, et al. Light-Driven Contact Hearing Aid for Broad Spectrum Amplification: Safety and Effectiveness Pivotal Study. Otology & Neurotology Journal, 2016 (in review).
Gennum, GA3280 Preliminary Data Sheet: Voyageur TD Open Platform DSP System for Ultra Low Audio Processing, downloaded from the Internet:<<http://www.sounddesigntechnologies.com/products/pdf/37601DOC.pdf>>, Oct. 2006; 17 pages.
Gobin, et al. Comments on the physical basis of the active materials concept. Proc. SPIE 2003; 4512:84-92.
Hato, et al. Three-dimensional stapes footplate motion in human temporal bones. Audiol. Neurootol., 8:140-152 (Jan. 30, 2003).
Headphones. Wikipedia Entry, downloaded from the Internet : en.wikipedia.org/wiki/Headphones. Accessed Oct. 27, 2008. 7 pages total.
Hofman, et al. Relearning Sound Localization With New Ears. Nature Neuroscience, vol. 1, No. 5, (Sep. 1998); 417-421.
International search report and written opinion dated Jun. 19, 2012 for PCT Application No. US2011/066306.
Jian, et al. A 0.6 V, 1.66 mW energy harvester and audio driver for tympanic membrane transducer with wirelessly optical signal and power transfer. InCircuits and Systems (ISCAS), 2014 IEEE International Symposium on Jun 1, 2014. 874-7. IEEE.
Jin, et al. Speech Localization. J. Audio Eng. Soc. convention paper, presented at the AES 112th Convention, Munich, Germany, May 10-13, 2002, 13 pages total.
Khaleghi, et al. Characterization of Ear-Canal Feedback Pressure due to Umbo-Drive Forces: Finite-Element vs. Circuit Models. ARO Midwinter Meeting 2016, (San Diego).
Killion, et al. The case of the missing dots: AI and SNR loss. The Hearing Journal, 1998. 51(5), 32-47.
Killion. Myths About Hearing Noise and Directional Microphones. The Hearing Review. Feb. 2004; 11(2):14, 16, 18, 19, 72 & 73.
Killion. SNR loss: I can hear what people say but I can't understand them. The Hearing Review, 1997; 4(12):8-14.
Lee, et al. A Novel Opto-Electromagnetic Actuator Coupled to the tympanic Membrane. J Biomech. Dec. 5, 2008;41(16):3515-8. Epub Nov. 7, 2008.
Lee, et al. The optimal magnetic force for a novel actuator coupled to the tympanic membrane: a finite element analysis. Biomedical engineering: applications, basis and communications. 2007; 19(3):171-177.
Levy, et al. Characterization of the available feedback gain margin at two device microphone locations, in the fossa triangularis and Behind the Ear, for the light-based contact hearing device. Acoustical Society of America (ASA) meeting, 2013 (San Francisco).
Levy, et al. Extended High-Frequency Bandwidth Improves Speech Reception in the Presence of Spatially Separated Masking Speech. Ear Hear. Sep.-Oct. 2015;36(5):e214-24. doi: 10.1097/AUD.0000000000000161.
Lezal. Chalcogenide glasses—survey and progress. Journal of Optoelectronics and Advanced Materials. Mar. 2003; 5(1):23-34.
Martin, et al. Utility of Monaural Spectral Cues is Enhanced in the Presence of Cues to Sound-Source Lateral Angle. JARO. 2004; 5:80-89.
Moore, et al. Perceived naturalness of spectrally distorted speech and music. J Acoust Soc Am. Jul. 2003;114(1):408-19.
Moore, et al. Spectro-temporal characteristics of speech at high frequencies, and the potential for restoration of audibility to people with mild-to-moderate hearing loss. Ear Hear. Dec. 2008;29(6):907-22. doi: 10.1097/AUD.0b013e31818246f6.
Moore. Loudness perception and intensity resolution. Cochlear Hearing Loss, Chapter 4, pp. 90-115, Whurr Publishers Ltd., London (1998).
Murugasu, et al. Malleus-to-footplate versus malleus-to-stapes-head ossicular reconstruction prostheses: temporal bone pressure gain measurements and clinical audiological data. Otol Neurotol. Jul. 2005; 2694):572-582.
Musicant, et al. Direction-Dependent Spectral Properties of Cat External Ear: New Data and Cross-Species Comparisons. J. Acostic. Soc. Am, May 10-13, 2002, vol. 87, No. 2, (Feb. 1990), pp. 757-781.
National Semiconductor, LM4673 Boomer: Filterless, 2.65W, Mono, Class D Audio Power Amplifier, [Data Sheet] downloaded from the Internet:<<http://www.national.com/ds/LM/LM4673.pdf>>; Nov. 1, 2007; 24 pages.
Notice of allowance dated Feb. 4, 2016 for U.S. Appl. No. 13/919,079.
Notice of allowance dated Mar. 16, 2016 for U.S. Appl. No. 13/919,079.
O'Connor, et al. Middle ear Cavity and Ear Canal Pressure-Driven Stapes Velocity Responses in Human Cadaveric Temporal Bones. J Acoust Soc Am. Sep. 2006;120(3):1517-28.
Office action dated Dec. 31, 2014 for U.S. Appl. No. 13/919,079.
Perkins, et al. Light-based Contact Hearing Device: Characterization of available Feedback Gain Margin at two device microphone locations. Presented at AAO-HNSF Annual Meeting, 2013 (Vancouver).
Perkins, et al. The EarLens Photonic Transducer: Extended bandwidth. Presented at AAO-HNSF Annual Meeting, 2011 (San Francisco).
Perkins, et al. The EarLens System: New sound transduction methods. Hear Res. Feb. 2, 2010; 10 pages total.
Perkins, R. Earlens tympanic contact transducer: a new method of sound transduction to the human ear. Otolaryngol Head Neck Surg. Jun. 1996;114(6):720-8.
Poosanaas, et al. Influence of sample thickness on the performance of photostrictive ceramics, J. App. Phys. Aug. 1, 1998; 84(3):1508-1512.
Puria et al. A gear in the middle ear. ARO Denver CO, 2007b.
Puria, et al. Cues above 4 kilohertz can improve spatially separated speech recognition. The Journal of the Acoustical Society of America, 2011, 129, 2384.
Puria, et al. Extending bandwidth above 4 kHz improves speech understanding in the presence of masking speech. Association for Research in Otolaryngology Annual Meeting, 2012 (San Diego).

(56) References Cited

OTHER PUBLICATIONS

Puria, et al. Extending bandwidth provides the brain what it needs to improve hearing in noise. First international conference on cognitive hearing science for communication, 2011 (Linkoping, Sweden).
Puria, et al. Hearing Restoration: Improved Multi-talker Speech Understanding. 5th International Symposium on Middle Ear Mechanics in Research and Otology (MEMRO), Jun. 2009 (Stanford University).
Puria, et al. Imaging, Physiology and Biomechanics of the middle ear: Towards understating the functional consequences of anatomy. Stanford Mechanics and Computation Symposium, 2005, ed Fong J.
Puria, et al. Malleus-to-footplate ossicular reconstruction prosthesis positioning: cochleovestibular pressure optimization. Otol Nerotol. May 2005; 2693):368-379.
Puria, et al. Measurements and model of the cat middle ear: Evidence of tympanic membrane acoustic delay. J. Acoust. Soc. Am., 104(6):3463-3481 (Dec. 1998).
Puria, et al. Middle Ear Morphometry From Cadaveric Temporal Bone MicroCT Imaging. Proceedings of the 4th International Symposium, Zurich, Switzerland, Jul. 27-30, 2006, Middle Ear Mechanics in Research and Otology, pp. 259-268.
Puria, et al. Sound-Pressure Measurements in the Cochlear Vestibule of Human-Cadaver Ears. Journal of the Acoustical Society of America. 1997; 101 (5-1): 2754-2770.
Puria, et al. Temporal-Bone Measurements of the Maximum Equivalent Pressure Output and Maximum Stable Gain of a Light-Driven Hearing System That Mechanically Stimulates the Umbo. Otol Neurotol. Feb. 2016;37(2):160-6. doi: 10.1097/MAO.0000000000000941.
Puria, et al. The EarLens Photonic Hearing Aid. Association for Research in Otolaryngology Annual Meeting, 2012 (San Diego).
Puria, et al. The Effects of bandwidth and microphone location on understanding of masked speech by normal-hearing and hearing-impaired listeners. International Conference for Hearing Aid Research (IHCON) meeting, 2012 (Tahoe City).
Puria, et al. Tympanic-membrane and malleus-incus-complex co-adaptations for high-frequency hearing in mammals. Hear Res. May 2010;263(1-2):183-90. doi: 10.1016/j.heares.2009.10.013. Epub Oct. 28, 2009.
Puria. Measurements of human middle ear forward and reverse acoustics: implications for otoacoustic emissions. J Acoust Soc Am. May 2003;113(5):2773-89.
Puria, S. Middle Ear Hearing Devices. Chapter 10. Part of the series Springer Handbook of Auditory Research pp. 273-308. Date: Feb. 9, 2013.
Sekaric, et al. Nanomechanical resonant structures as tunable passive modulators. App. Phys. Lett. Nov. 2003; 80(19):3617-3619.
Shaw. Transformation of Sound Pressure Level From the Free Field to the Eardrum in the Horizontal Plane. J. Acoust. Soc. Am., vol. 56, No. 6, (Dec. 1974), 1848-1861.
Shih. Shape and displacement control of beams with various boundary conditions via photostrictive optical actuators. Proc. IMECE. Nov. 2003; 1-10.
Song, et al. The development of a non-surgical direct drive hearing device with a wireless actuator coupled to the tympanic membrane. Applied Acoustics. Dec. 31, 2013;74(12):1511-8.
Sound Design Technologies,—Voyager TDTM Open Platform DSP System for Ultra Low Power Audio Processing—GA3280 Data Sheet. 2007 Oct; retrieved from the Internet:<<http://www.sounddes.com/pdf/37601DOC.pdf>>, 15 page total.
Stuchlik, et al. Micro-Nano Actuators Driven by Polarized Light. IEEE Proc. Sci. Meas. Techn. Mar. 2004; 151(2):131-136.
Suski, et al. Optically activated ZnO/Si02/Si cantilever beams. Sensors and Actuators A (Physical), 0 (nr: 24). 2003; 221-225.
Takagi, et al. Mechanochemical Synthesis of Piezoelectric PLZT Powder. KONA. 2003; 51(21):234-241.
Thakoor, et al. Optical microactuation in piezoceramics. Proc. SPIE. Jul. 1998; 3328:376-391.
Thompson. Tutorial on microphone technologies for directional hearing aids. Hearing Journal. Nov. 2003; 56(11):14-16,18, 20-21.
Tzou, et al. Smart Materials, Precision Sensors/Actuators, Smart Structures, and Structronic Systems. Mechanics of Advanced Materials and Structures. 2004; 11:367-393.
Uchino, et al. Photostricitve actuators. Ferroelectrics. 2001; 258:147-158.
Vickers, et al. Effects of Low-Pass Filtering on the Intelligibility of Speech in Quiet for People With and Without Dead Regions at High Frequencies. J. Acoust. Soc. Am. Aug. 2001; 110(2):1164-1175.
Wang, et al. Preliminary Assessment of Remote Photoelectric Excitation of an Actuator for a Hearing Implant. Proceeding of the 2005 IEEE, Engineering in Medicine and Biology 27th nnual Conference, Shanghai, China. Sep. 1-4, 2005; 6233-6234.
Wiener, et al. On the Sound Pressure Transformation by the Head and Auditory Meatus of the Cat. Acta Otolaryngol. Mar. 1966; 61(3):255-269.
Wightman, et al. Monaural Sound Localization Revisited. J Acoust Soc Am. Feb. 1997;101(2):1050-1063.
Yi, et al. Piezoelectric Microspeaker with Compressive Nitride Diaphragm. The Fifteenth IEEE International Conference on Micro Electro Mechanical Systems, 2002; 260-263.
Yu, et al. Photomechanics: Directed bending of a polymer film by light. Nature. Sep. 2003; 425:145.
Co-pending U.S. Appl. No. 16/013,839, filed Jun. 20, 2018.
Galbraith et al. A wide-band efficient inductive transdermal power and data link with coupling insensitive gain IEEE Trans Biomed Eng. Apr. 1987;34(4):265-75.
Kiessling, et al. Occlusion Effect of Earmolds with Different Venting Systems. J Am Acad Audiol. Apr. 2005;16(4):237-49.
School of Physics Sydney, Australia. Acoustic Compliance, Inertance and Impedance. 1-6. (2018). http://www.animations.physics.unsw.edu.au/jw/compliance-inertance-impedance.htm.
Wikipedia. Inductive Coupling. 1-2 (Jan. 11, 2018). https://en.wikipedia.org/wiki/Inductive_coupling.
Wikipedia. Pulse-density Coupling. 1-4 (Apr. 6, 2017). https://en.wikipedia.org/wiki/Pulse-density_modulation.
Vinge. Wireless Energy Transfer by Resonant Inductive Coupling. Master of Science Thesis. Chalmers University of Technology. 1-83 (2015).
Wikipedia. Resonant Inductive Coupling. 1-11 (Jan. 12, 2018). https://en.wikipedia.org/wiki/Resonant_inductive_coupling#cite_note-13.

* cited by examiner

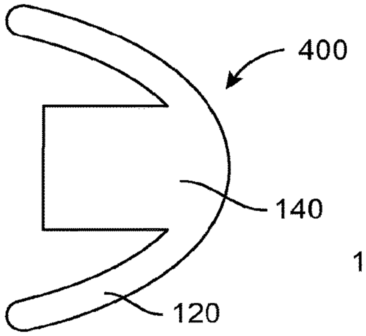
FIG. 5A1
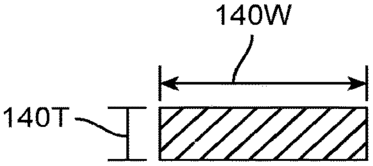
FIG. 5A2
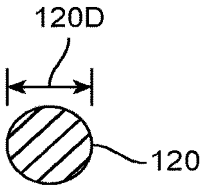
FIG. 5A3
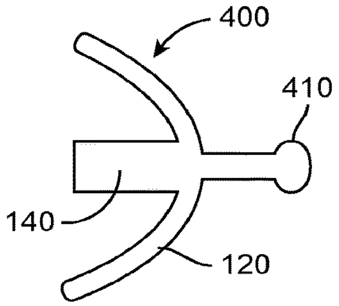
FIG. 5A4
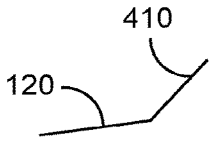
FIG. 5A5

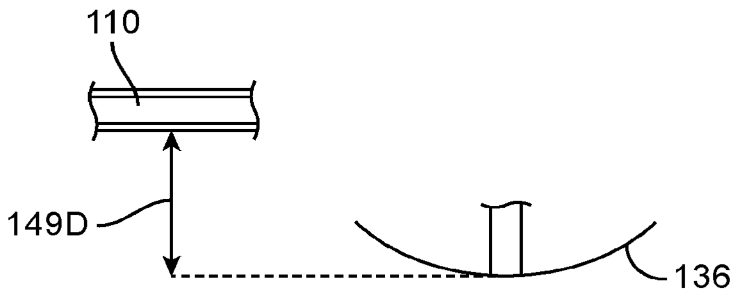
FIG. 5B1
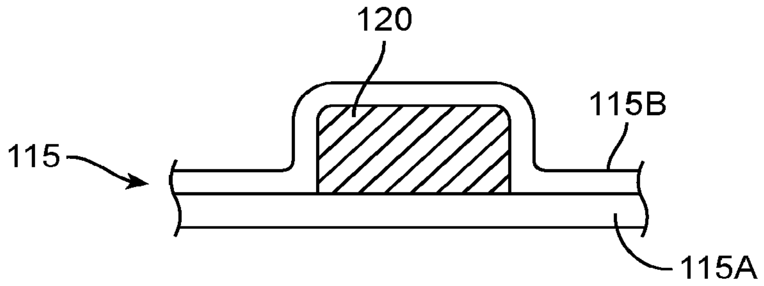
FIG. 5B2

ANATOMICALLY CUSTOMIZED EAR CANAL HEARING APPARATUS

CROSS-REFERENCES TO RELATED APPLICATIONS

This application is a continuation of U.S. patent application Ser. No. 13/919,079, filed Jun. 17, 2013, which is a continuation of international application number PCT/US11/66306, filed Dec. 20, 2011, which claims priority to U.S. Pat. App. Ser. No. 61/425,000, filed Dec. 20, 2010, entitled "Anatomically Customized Ear Canal Hearing Apparatus", the entire disclosures of which are incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

1. Field of the Invention

The present invention is related to systems, devices and methods that couple to tissue such as hearing systems. Although specific reference is made to hearing aid systems, embodiments of the present invention can be used in many applications in which a signal is used to stimulate the ear.

People like to hear. Hearing allows people to listen to and understand others. Natural hearing can include spatial cues that allow a user to hear a speaker, even when background noise is present. People also like to communicate with those who are far away, such as with cellular phones.

Hearing devices can be used with communication systems to help the hearing impaired and to help people communicate with others who are far away. Hearing impaired subjects may need hearing aids to verbally communicate with those around them. Unfortunately, the prior hearing devices can provide less than ideal performance in at least some respects, such that users of prior hearing devices remain less than completely satisfied in at least some instances.

Examples of deficiencies of prior hearing devices include feedback, distorted sound quality, less than desirable sound localization, discomfort and autophony. Feedback can occur when a microphone picks up amplified sound and generates a whistling sound. Autophony includes the unusually loud hearing of a person's own self-generated sounds such as voice, breathing or other internally generated sound. Possible causes of autophony include occlusion of the ear canal, which may be caused by an object blocking the ear canal and reflecting sound vibration back toward the eardrum, such as an unvented hearing aid or a plug of earwax reflecting sound back toward the eardrum.

Although acoustic hearing aids can increase the volume of sound to a user, acoustic hearing aids provide sound quality that can be less than ideal and may not provide adequate speech recognition for the hearing impaired in at least some instances. Acoustic hearing aids can rely on sound pressure to transmit sound from a speaker within the hearing aid to the eardrum of the user. However, the sound quality can be less than ideal and the sound pressure can cause feedback to a microphone placed near the ear canal opening Although placement of an acoustic hearing aid along the bony portion of the ear canal may decrease autophony and feedback, the fitting of such deep canal acoustic devices can be less than ideal such that many people are not able to use the devices. In at least some instances sound leakage around the device may result in feedback. The ear canal may comprise a complex anatomy and the prior deep canal acoustic devices may be less than ideally suited for the ear canals of at least some patients. Also, the amount of time a hearing device can remain inserted in the bony portion of the ear canal can be less than ideal, and in at least some instances skin of the ear canal may adhere to the hearing device such that removal and comfort may be less than ideal.

Although it has been proposed to couple a transducer to the eardrum to stimulate the eardrum with direct mechanical coupling, the clinical implementation of the prior direct mechanical coupling devices has been less than ideal in at least some instances. Coupling the transducer to the eardrum can provide amplified sound with decreased feedback, such that in at least some instances a microphone can be placed in or near the ear canal to provide hearing with spatial information cues. However, the eardrum is a delicate tissue structure, and in at least some instances the placement and coupling of the direct mechanical coupling devices can be less than ideal. For example, in many patients the deepest portion of the ear canal comprises the anterior sulcus, and a device extending to the anterior sulcus can be difficult for a clinician to view in at least some instances. Further, at least some prior direct coupling devices have inhibited viewing of the eardrum and the portion of the device near the eardrum, which may result in less than ideal placement and coupling of the transducer to the eardrum. Also, direct coupling may result in autophony in at least some instances. The eardrum can move substantially in response to atmospheric pressure changes, for example about one millimeter, and at least some of the prior direct coupling devices may not be well suited to accommodate significant movement of the eardrum in at least some instances. Also, the naturally occurring movement of the user such as chewing and eardrum movement may decouple at least some of the prior hearing devices. Although prior devices have been provided with a support to couple a magnet to the eardrum, the success of such coupling devices can vary among patients and the results can be less than ideal in at least some instances.

Although the above described prior systems can help people hear better, many people continue to have less than ideal hearing with such devices and it would be beneficial to provide improved coupling of the transducer assembly to the eardrum and ear canal. Also, it would be helpful to provide improved coupling in simplified manner such that the assemblies can be manufactured reliably for many users such that many people can enjoy the benefits of better hearing.

For the above reasons, it would be desirable to provide hearing systems and improved manufacturing which at least decrease, or even avoid, at least some of the above mentioned limitations of the prior hearing devices. For example, there is a need to provide improved manufacturing of reliable, comfortable hearing devices which provide hearing with natural sound qualities, for example with spatial information cues, and which decrease autophony, distortion and feedback.

2. Description of the Background Art

Patents and publications that may be relevant to the present application include: U.S. Pat. Nos. 3,585,416; 3,764,748; 3,882,285; 5,142,186; 5,554,096; 5,624,376; 5,795,287; 5,800,336; 5,825,122; 5,857,958; 5,859,916; 5,888,187; 5,897,486; 5,913,815; 5,949,895; 6,005,955; 6,068,590; 6,093,144; 6,139,488; 6,174,278; 6,190,305; 6,208,445; 6,217,508; 6,222,302; 6,241,767; 6,422,991; 6,475,134; 6,519,376; 6,620,110; 6,626,822; 6,676,592; 6,728,024; 6,735,318; 6,900,926; 6,920,340; 7,072,475; 7,095,981; 7,239,069; 7,289,639; D512,979; 2002/0086715; 2003/0142841; 2004/0234092; 2005/0020873; 2006/0107744; 2006/0233398; 2006/075175; 2007/0083078; 2007/0191673; 2008/0021518; 2008/0107292; commonly owned U.S. Pat. Nos. 5,259,032; 5,276,910; 5,425,104; 5,804,109; 6,084,975; 6,554,761; 6,629,922; U.S. Publication Nos. 2006/0023908; 2006/0189841; 2006/0251278; and 2007/0100197. Non-U.S. patents and publications that may be relevant include EP1845919 PCT Publication Nos. WO 03/063542; WO 2006/075175; U.S. Publication Nos. Journal publications that may be relevant include: Ayatollahi et al., "Design and Modeling of Micromachines Condenser MEMS Loudspeaker using Permanent Magnet Neodymium-Iron-Boron (Nd—Fe—B)", ISCE, Kuala Lampur, 2006; Birch et al, "Microengineered Systems for the Hearing Impaired", IEE, London, 1996; Cheng et al., "A silicon microspeaker for hearing instruments", J. Micromech. Microeng., 14(2004) 859-866; Yi et al., "Piezoelectric microspeaker with compressive nitride diaphragm", IEEE, 2006, and Zhigang Wang et al., "Preliminary Assessment of Remote Photoelectric Excitation of an Actuator for a Hearing Implant", IEEE Engineering in Medicine and Biology 27th Annual Conference, Shanghai, China, Sep. 1-4, 2005. Other publications of interest include: Gennum GA3280 Preliminary Data Sheet, "Voyager TD™. Open Platform DSP System for Ultra Low Power Audio Processing" and National Semiconductor LM4673 Data Sheet, "LM4673 Filterless, 2.65 W, Mono, Class D audio Power Amplifier"; Puria, S. and Steele, C Tympanic-membrane and malleus-incus-complex co-adaptations for high-frequency hearing in mammals. Hear Res 2010 263(1-2):183-90; O'Connor, K. and Puria, S. "Middle ear cavity and ear canal pressure-driven stapes velocity responses in human cadaveric temporal bones" J. Acoust. Soc. Am. 120(3) 1517-1528.

BRIEF SUMMARY OF THE INVENTION

The present invention is related to hearing systems, devices and methods. Although specific reference is made to hearing aid systems, embodiments of the present invention can be used in many applications in which a signal is used to transmit sound to a user, for example cellular communication and entertainment systems. The vapor deposition and polymerization as described herein can be used with many devices, such as medical devices comprising a component having a shape profile corresponding to a tissue surface. Although specific reference is made to a transducer assembly for placement in an ear canal of a user, embodiments of the present invention can be used with many devices and tissues, such as dental tissue, teeth, orthopedic tissue, bones, joints, ocular tissue, eyes and combinations thereof. In many embodiments, the vapor deposition and polymerization can be used to manufacture a component of a hearing system used to transmit sound to a user.

Embodiments of the present invention provide improved methods of manufacturing suitable for use with hearing devices so as to overcome at least some of the aforementioned limitations of the prior methods and apparatus. In many embodiments, a vapor deposition process can be used to make a support structure having a shape profile corresponding to a tissue surface, such as a retention structure having a shape profile corresponding to one or more of the eardrum, the eardrum annulus, or a skin of the ear canal. The retention structure can be deflectable to provide comfort, resilient to provide support, and may comprise a component of an output transducer assembly to couple to the eardrum of the user. The resilient retention structure may comprise an anatomically accurate shape profile corresponding to a portion of the ear, such that the resilient retention structure provides mechanical stability for the output transducer assembly and comfort for the user when worn for an extended time. The output transducer assembly comprising the retention structure having the shape profile can be placed in the ear of the user, and can be comfortably worn for months and in many embodiments worn comfortably and maintain functionality for years.

The output transducer assembly may comprise a support having stiffness greater than a stiffness of the resilient retention structure, and the stiff support may comprise one or more of arms, a rigid frame, or a chassis. The support stiffness greater than the retention structure can maintain alignment of the components coupled to the support, such that appropriate amounts of force can be used to urge a coupling structure against the eardrum so as to couple the transducer to the eardrum with decreased autophony. The stiff support can be coupled to at least one spring so as to provide appropriate amounts of force to the eardrum with the coupling structure and to inhibit deformation of the device when placed in the loaded configuration for the extended time. The deflectable retention structure may provide a narrow profile configuration when advanced into the ear canal and a wide profile configuration when placed in the ear canal, and the stiff support can be used to deflect and advance the retention structure along the ear canal. A photodetector and an output transducer can be coupled to the support, such that the transducer assembly can be mechanically secure and stable when placed within the anatomy of the ear canal of the user. The support can have an elastomeric bumper structure placed thereon so as to protect the eardrum and skin when the support and retention structure are coupled to the eardrum and skin. Alternatively, the stiff support can be placed on the layer of vapor deposited polymer and affixed to the layer, such that the vapor deposited layer contacts the eardrum or skin. A second layer can be deposited on the first layer when the first layer has been placed on the first layer to situate the stiff support structure between the layers. The stiff support may comprise a part comprising arms, an intermediate portion extending between the arms, and at least one spring, such that the stiff support part can be placed an affixed to the retention structure.

The output transducer assembly may comprise a biasing structure coupled to the support to adjust a position of a coupling structure that engages the eardrum. The at least one spring can be coupled to the support and the transducer, so as to support the transducer and the coupling structure in an unloaded configuration. The biasing structure can be configured to adjust the unloaded position of the coupling structure prior to placement. The at least one spring can be coupled to the coupling structure such that the coupling structure can move about one millimeter from the unloaded position in response to the eardrum loading the coupling structure. The spring can be configured to provide an appropriate force to the coupling structure engage the eardrum and to inhibit occlusion when the coupling structure comprises either the unloaded configuration or the configuration with displacement in response to eardrum movement of about one millimeter. Alternatively or in combination, the biasing structure may comprise a dynamic biasing structure having a biasing transducer coupled to the at least one spring to urge the coupling structure into engagement with the eardrum in response to a signal to the output transducer.

A vapor deposition and polymerization process can be used to provide a strong and secure connection extending between the support and the resilient retention structure. The vapor deposition process may comprise a poly(p-xylylene) polymer deposition process and the resilient retention structure may comprise a layer of vapor deposited poly(p-xylylene) polymer adhered to the support. The vapor-deposited Poly(p-xylylene) polymer may also adhere to the elastomeric bumper structure material such as a silicone material. The vapor deposition of the layer of material to form the retention structure can provide a uniform accurate shape profile in a semi-automated manner that can increase reproducibility and accuracy with decreased labor so as to improve coupling and hearing for many people.

The vapor deposition process can be used to manufacture the output transducer assembly with a positive mold of the ear canal of the user. The positive mold may comprise an optically transmissive material, and a release agent may coat an inner surface of the positive mold. The release agent may comprise a hydrophilic material such that the coating can be removed from the mold with water. The layer can be formed with vapor deposition within the positive mold. The components can be placed on the layer. The positive mold may comprise a transparent material, such that the placement of the components within the positive mold can be visualized. A second layer can be vapor deposited over the first layer to affix the components to the first layer and the second layer.

The retention structure may comprise a deflection to receive epithelium. The retention structure may comprise a surface to contact a surface of an epithelial tissue. The epithelial tissue may migrate under the retention structure when placed for an extended time. The deflection of the retention structure surface can be located near an edge of the retention structure and extend away from the surface of the tissue so as to inhibit accumulation of epithelial tissue near the edge of the retention structure. The deflected edge can be oriented toward a source of epithelium such as the umbo when the retention structure is placed in the ear canal.

The output transducer assembly may comprise an oleophobic coating to inhibit autophony and accumulation of oil on components of the assembly.

The retention structure can be configured in many ways to permit viewing of the retention structure and the eardrum. The retention structure may comprise a transparent material, which can allow a clinician to evaluate coupling of the retention structure to the tissue of the ear canal. In many embodiments, the ear canal comprises an opening, which allows a clinician to view at least a portion of the eardrum and evaluate placement of the output transducer assembly. In many embodiments, the retention structure is dimensioned and shaped to avoid extending into the anterior sulcus to improve visibility when placed, and the retention structure may extend substantially around an outer portion of the eardrum such as the eardrum annulus so as to define an aperture through which the eardrum can be viewed. Alternatively, the retention structure may extend around no more than a portion of the annulus. In many embodiments, the retention structure extends to a viewable location an opposite side of the ear canal, so as to limit the depth of placement in the ear canal and facilitate the clinician viewing of the retention structure. The visibility of the retention structure can be increased substantially when the retention structure extends around no more than a portion of the annulus and also extends to a portion of the ear canal opposite the eardrum. The wall opposite the eardrum can support the transducer with the portion opposite the annulus so as to improve coupling. The portions of the retention structure extending to the canal wall opposite the eardrum and around no more than a portion of the annulus can be easily viewed and may define a viewing aperture through which the eardrum can be viewed.

In a first aspect, embodiments provide a method of making a support for placement on a tissue of a user. A material of a vapor is deposited on a substrate to form the support. The substrate has a shape profile corresponding to the tissue, and the support is separated from the substrate.

In many embodiments, the material is polymerized on the substrate to form the support having the shape profile.

In many embodiments, a solid layer of the material forms having the shape profile and wherein the support comprises the solid layer when separated from the substrate.

In many embodiments, the release agent is disposed on the substrate between the substrate and the support when the vapor is deposited on the release agent to form the support. The release agent may comprise one or more of one or more of PEG, a hydrophilic coating, a surface treatment such as corona discharge, a surfactant, a wax, hydrophilic wax, or petroleum jelly. The release agent may comprise a solid when the vapor is deposited at an ambient temperature, and the release agent can be heated so as to comprise a liquid when the support is separated from the substrate. The release agent may have a first surface oriented toward the substrate and in contact with the substrate and a second surface oriented away from the substrate so as to contact the support, and the second surface can be smoother than the first surface such that the release agent may also comprise a smoothing agent.

In many embodiments, the release agent comprises a water soluble material such as water soluble polymer or a surfactant.

In many embodiments, the material of the vapor comprises monomer molecules having aromatic rings and wherein the monomer molecules are polymerized to form a polymer on the substrate having the aromatic rings.

In many embodiments, the material of the vapor comprises Poly(p-xylylene) polymer and the slip agent comprises petroleum jelly.

In many embodiments, the material of the vapor comprises polyvinyl alcohol (hereinafter "PVA") or polyvinyl alcohol hydrogel (hereinafter "PVA-H").

In many embodiments, the material of the vapor can deposited with one or more of thermal deposition, radio frequency deposition, or plasma deposition.

In many embodiments, the shape profile of the substrate corresponds to a shape profile of a tissue surface, and the shape profile comprises a portion having a deflection away from the shape profile of the tissue surface so as to provide a deflection in the support away from a surface of the tissue. The tissue surface may comprise an epithelial surface, and the deflection is configured to extend away from the epithelial surface when the support is placed. The deflection can be oriented on the support so as to receive the advancing epithelium under the deflection.

In many embodiments, the substrate comprises a portion of an optically transmissive positive mold of the tissue, and components of a hearing device are placed in the mold with visualization of the components through the optically transmissive positive mold.

In many embodiments, the tissue comprises at least a portion of an ear canal or a tympanic membrane of a user. A negative mold is made of the at least the portion or the tympanic membrane. The negative mold is coated with an optically transmissive material. The coating is cured. The cured coating is placed in a container comprising an optically transmissive flowable material. The optically transmissive flowable material is cured to form a positive mold, the cured coating inhibits deformation of the negative mold when the optically transmissive flowable material is cured.

In many embodiments, the support comprises a first layer of the polymerizable material and a second layer of the polymerizable material, and components of a hearing device are situated between the first layer and the second layer.

In many embodiments, components of the hearing device are placed on the first layer and the second layer deposited on the components placed on the first layer and the first layer.

In many embodiments, an oleophobic coating is placed on one or more of the first transducer or the retention structure.

In many embodiments, the support comprises a retention structure shaped for placement in an ear canal of a user, and a part is placed. The part comprises a support component comprising arms, and the arms are affixed to the retention structure.

In many embodiments, the vapor is deposited on the part to affix the part to the retention structure.

In many embodiments, a projection extends from the part to place the retention structure in the ear canal of the user.

In many embodiments, the support comprises a retention structure shaped for placement in an ear canal of a user, and the support is cut along a portion toward an eardrum and a portion toward an opening of the ear canal so as to define an opening to couple a transducer to an eardrum of the user. The portion toward the eardrum may correspond to an anterior sulcus of the ear canal, and the portion toward the opening of the ear canal may correspond to the bony part of the ear canal. The portion toward the eardrum can be cut to limit insertion depth such that a clinician can view the portion toward the eardrum when placed.

In another aspect, embodiments provide an apparatus for placement with a user, the apparatus comprises a transducer and a retention structure. The retention structure comprises a layer of polymer having a shape profile corresponding to a tissue of the user to couple the transducer to the user.

In many embodiments, the retention structure comprises a curved portion having an inner surface toward an eardrum when placed, and the curved portion couples to an ear canal wall oriented toward the eardrum when placed to couple a transducer to the eardrum. The curved portion may couple to the ear canal on a first side of the ear canal opposite the eardrum, and a second portion of the retention structure may couple to a second side of the ear canal opposite the first side to hold the retention structure in the ear canal. The curved portion and the second portion can be connected so as to define an aperture extending therebetween to view at least a portion of the eardrum when the curved portion couples to the first side of the ear canal and the second portion couples to the second side.

In many embodiments, the support comprises a first layer of a polymerizable material and a second layer of a polymerizable material and wherein components of a hearing device are situated between the first layer and the second layer.

In many embodiments, an oleophobic layer is coated on one or more of the first transducer or the retention structure.

In many embodiments, the tissue comprises an eardrum having a first resistance to deflection and a bony portion of the ear canal having a second resistance to deflection greater than the first resistance, and the layer comprises a resistance to deflection greater than the eardrum and less than the bony portion of the ear canal.

In many embodiments, the layer comprises a material having a thickness to resist deflection away from the shape profile and wherein the layer comprises the shape profile in an unloaded configuration.

In many embodiments, the transducer couples to a tissue structure having a resistance to deflection, and the layer comprises a resistance to deflection greater than the tissue structure.

In many embodiments, the layer comprises a thickness within a range from about 1 um to about 100 um. The layer may comprise a substantially uniform thickness to provide the resistance to deflection and the shape profile in the unloaded configuration. The thickness of the layer can be uniform to within about +/−25 percent of an average thickness to provide the shape profile.

In many embodiments, the retention structure comprises a resilient retention structure to maintain a location of the transducer when coupled to the user.

In many embodiments, wherein the resilient retention structure is sized to fit within an ear canal of the user and contact one or more of a skin of the ear canal or an eardrum annulus so as to maintain a location of the transducer when placed in the ear canal.

In many embodiments, the retention structure comprises a layer composed of one or more of poly(chloro-p-xylene), poly(p-xylene), poly(dichloro-p-xylene), or fluorinated poly (p-xylene).

In many embodiments, the apparatus comprises a support to couple the transducer to the retention structure. The support may comprises a stiff support having a pair of curved arms extending substantially along outer portions of the retention structure, and the curved arms can be configured to deflect inward with the retention structure when the support is advanced along an ear canal of the user.

In many embodiments, the transducer is supported with at least one spring extending between the support and the transducer. The support may comprise an intermediate portion extending between the arms, and the at least one spring may extends from the intermediate portion to the transducer to support the transducer. The at least one spring comprises a cantilever extending from the intermediate portion to the transducer to support the transducer. The at least one spring, the arms, and the intermediate section may comprise a single part manufactured with a material.

In many embodiments, a projection extends from the single part to place the retention structure in the ear canal of the user. The single part may comprise one or more of a molded part, an injection molded part, or a machined part.

In many embodiments, the at least one spring comprises a pair of springs, a first spring of the pair coupled to a first side of the transducer, a second spring of the pair coupled to a second side of the transducer opposite the first side, so as to support the transducer with springs coupled to the support on opposing sides.

In many embodiments, the apparatus further comprises a coupling structure shaped to engage the eardrum to vibrate the eardrum, and a biasing structure to adjust an offset between the support and the coupling structure.

In many embodiments, the biasing structure is configured to adjust a separation distance extending between a lower surface of the retention structure and a lower surface of the coupling structure in an unloaded configuration, and the coupling structure is coupled to the support with at least one spring such that the separation distance decreases when the coupling structure contacts the eardrum.

In many embodiments, the biasing structure, the support, and the coupling structure are coupled to the at least one spring so as to provide about one mm or more of deflection of the coupling structure toward the support when the coupling structure engages the eardrum in a loaded configuration.

In many embodiments, the biasing structure is configured to adjust a position of the transducer in relation so as to the support to position the coupling structure with the offset.

In many embodiments, a photodetector attached to a casing of the transducer. The transducer can be configured to pivot relative to the support, and the photodetector pivots with the transducer.

In many embodiments, the shape profile corresponds to a shape profile of a tissue surface, and the shape profile comprises a portion having a deflection away from the shape profile of the tissue surface. The tissue surface may comprise an epithelial surface, and the deflection extends away from the epithelial surface when the support is placed. The deflection may be oriented on the support so as to receive advancing epithelium under the deflection.

In another aspect, embodiments provide a method of manufacturing an output transducer assembly for placement within a canal of an ear of a user, in which the user has an eardrum. A retention structure is provided that is sized to fit within the ear canal and contact one or more of a skin of the ear canal or an eardrum annulus. A support is coupled to the retention structure, and the support is sized to fit within the ear canal and defines an aperture. A transducer is coupled to the support, and the transducer comprises an elongate vibratory structure. The transducer is coupled to the support such that the elongate vibratory structure extends through the aperture to couple the transducer to the eardrum when the elongate structure is placed within the ear canal.

In many embodiments, the retention structure has a shape profile based on a mold corresponding to an anterior sulcus of the ear canal of the user.

In many embodiments, the retention structure comprises Poly(p-xylylene) polymer.

In many embodiments, the retention structure comprises a substantially annular retention structure and wherein the substantially annular retention structure defines an inner region, and the inner region is aligned with the aperture when the support is coupled to the retention structure such that the vibratory structure extends through the inner region and the aperture.

In many embodiments, the retention structure comprise a resilient retention structure and wherein the resilient retention structure has a first configuration comprising first dimensions so as to contact the eardrum annulus when placed, and the resilient retention structure has a second configuration when compressed. The second configuration comprises second dimensions such that the retention structure is sized to move along the ear canal for placement. Upon removal of compression the retention structure returns from the second configuration substantially to the first configuration.

In many embodiments, the support comprises an elongate dimension and rigidity greater than the retention structure and wherein the retention structure comprises a first portion sized to fit an anterior sulcus of the ear canal, and the elongate dimension is aligned with the first portion such that the retention structure can be compressed when moved along the ear canal.

In many embodiments, the support comprises a rigid sheet material cut so as to define the aperture and an outer perimeter of the support.

In many embodiments, the transducer comprises a housing having a first end and a second end and wherein the vibratory structure extends through a first end of the housing and a pair of coil springs is coupled to the second end of the housing. The pair extends between the second end and the support such that transducer is supported with the springs, and the vibratory structure is urged through the aperture when the retention structure is placed within the ear canal. Each of the coil springs may have a pivot axis extending through the coil and the pivot axis of said each coil can extend through the other coil such that the transducer pivots about a pivot axis extending through the coils to couple to the eardrum when the vibratory structure extends through the aperture. The aperture can be sized to receive the housing of the transducer assembly such that the transducer assembly can pivot through the aperture to increase the dynamic range of the pivoting of the transducer to couple to the eardrum.

In many embodiments, a photo transducer is coupled to the support and the transducer.

In another aspect, embodiments provide an output transducer assembly for placement in an ear of a user. A retention structure is sized to fit within the ear canal and contact one or more of a skin of the ear canal or an eardrum annulus. A support is coupled to the retention structure, and the support is sized to fit within the ear canal and defines an aperture. A transducer is coupled to the support. The transducer comprises an elongate vibratory structure, and the elongate vibratory structure extends through the aperture to couple the transducer to the eardrum when the elongate structure is placed within the ear canal.

In many embodiments, the aperture is sized to receive a housing of the transducer such that the housing extends at least partially through the aperture when the elongate vibratory structure is coupled to the eardrum.

In another aspect, embodiments provide a method of placing output transducer assembly in an ear of a user. A retention structure is compressed from a first wide profile configuration to a narrow profile configuration. The wide profile configuration is sized to fit within the ear canal and contact one or more of a skin of the ear canal or an eardrum annulus, and the narrow profile configuration sized to advance along the ear canal. A support coupled to the retention structure is advanced along the ear canal when the retention structure comprises the narrow profile configuration. The support is sized to fit within the ear canal and defines an aperture. A transducer is coupled to the support, and the transducer comprising an elongate vibratory structure. The elongate vibratory structure extends through the aperture to couple the transducer to the eardrum when the elongate structure is placed within the ear canal.

In many embodiments, the retention structure comprises a resilient retention structure in which the wide profile configuration has a shape profile corresponding to a portion of the ear canal of the user. The resilient retention structure expands from the narrow profile configuration to the wide profile configuration when advanced along the ear canal. The support comprises a rigid support having a substantially constant profile when the resilient retention structure is compressed and when the resilient retention structure is expanded.

BRIEF DESCRIPTION OF THE DRAWINGS

FIG. 3-1 shows an injection step, in accordance with embodiments of the present invention;

FIG. 3-2 shows a removal step, in accordance with embodiments of the present invention;

FIG. 3-3 shows a coating step, in accordance with embodiments of the present invention;

FIG. 3-4 shows an embedding step, in accordance with embodiments of the present invention;

FIG. 3-5 shows a machining step, in accordance with embodiments of the present invention;

FIG. 3-6 shows a submersion step, in accordance with embodiments of the present invention;

FIG. 3-7 shows a pretreatment step of coating a support, in accordance with embodiments of the present invention;

FIG. 3-8 shows a step of coupling the coated support to the mold, in accordance with embodiments of the present invention;

FIG. 3-9 shows vapor deposition of monomer to the mold to form a layer Parylene™ polymer film, in accordance with embodiments of the present invention;

FIG. 3-9A shows the structure Parylene™, in accordance with embodiments of the present invention;

FIG. 3-9B shows the structure Parylene™ C, in accordance with embodiments of the present invention;

FIG. 3-10 shows a top view of the mold and cutting of the layer of Parylene™ polymer film to prepare the film for removal from the mold, in accordance with embodiments of the present invention;

FIG. 3-11 shows the layer of Parylene™ polymer film removed from the mold and suitable for supporting with a backing material, in accordance with embodiments of the present invention;

FIG. 3-12 shows cutting the layer with a backing material, in accordance with embodiments of the present invention;

FIG. 4 shows a method of assembling an output transducer assembly, in accordance with embodiments of the present invention;

FIG. 5A1 shows an integrated component comprising the stiff support and resilient spring, in accordance with embodiments of the present invention;

FIGS. 5A2 and 5A3 show cross-sectional views of the resilient spring and the stiff support, respectively, in accordance with embodiments of the present invention;

FIGS. 5A4 and 5A5 show a top view and a side view, respectively, of a support comprising a graspable projection to place the output transducer assembly in the ear canal, in accordance with embodiments of the present invention;

FIG. 5B 1 shows a lower surface support positioned a distance beneath the lower surface of retention structure, in accordance with embodiments of the present invention;

FIG. 5B2 shows a component of the output transducer assembly retained between a first layer and a second layer, in accordance with embodiments of the present invention;

FIG. 9A shows a retention structure comprising an curved portion shaped to extend along a surface of the bony portion of the ear canal opposite an eardrum when placed, in which the curved portion is coupled to a transducer with a structure extending from the curved portion to the transducer to couple the transducer with the eardrum, in accordance with embodiments of the present invention;

FIG. 9B shows a dynamic biasing system, in accordance with embodiments of the present invention;

FIG. 11 shows a transducer to deflect the output transducer toward the eardrum and couple the output transducer to the eardrum in response to the output signal, in accordance with embodiments of the present invention; and FIG. 12 shows a retention structure configured for placement in the middle ear supporting an acoustic hearing aid, in accordance with embodiments of the present invention.

DETAILED DESCRIPTION OF THE INVENTION

Embodiments of the present invention are well suited to improve communication among people, for example with cellular communication and as a hearing aid with decreased invasiveness that can be readily placed by a health care provider.

As used herein, light encompasses electromagnetic radiation having wavelengths within the visible, infrared and ultraviolet regions of the electromagnetic spectrum.

In many embodiments, the hearing device comprises a photonic hearing device, in which sound is transmitted with photons having energy, such that the signal transmitted to the ear can be encoded with transmitted light.

As used herein, an emitter encompasses a source that radiates electromagnetic radiation and a light emitter encompasses a light source that emits light.

As used herein like references numerals and letters indicate similar elements having similar structure, function and methods of use.

As used herein a surfactant encompasses a wetting agent capable of reducing the surface tension of a liquid.

As used herein, scientific notation may comprises known E notation known to persons of ordinary skill in the art using computer programs such as spreadsheets, for example. The exponential value $A \times 10^{-B}$ can be expressed as Ae-B, or AE-B, for example.

As used herein reference to a chemical structure encompasses the chemical structure and derivatives thereof.

Transducer assemblies that couple the transducer to the eardrum so as to decrease occlusion are described in U.S. Pat. App. No. 61/217,801, filed Jun. 3, 2009, entitled "Balanced Armature Device and Methods for Hearing"; and PCT/US2009/057719, filed 21 Sep. 2009, entitled "Balanced Armature Device and Methods for Hearing", published as WO 2010/033933, the full disclosures of which are incorporated herein by reference and suitable for combination in accordance with embodiments as described herein.

Figure 1:
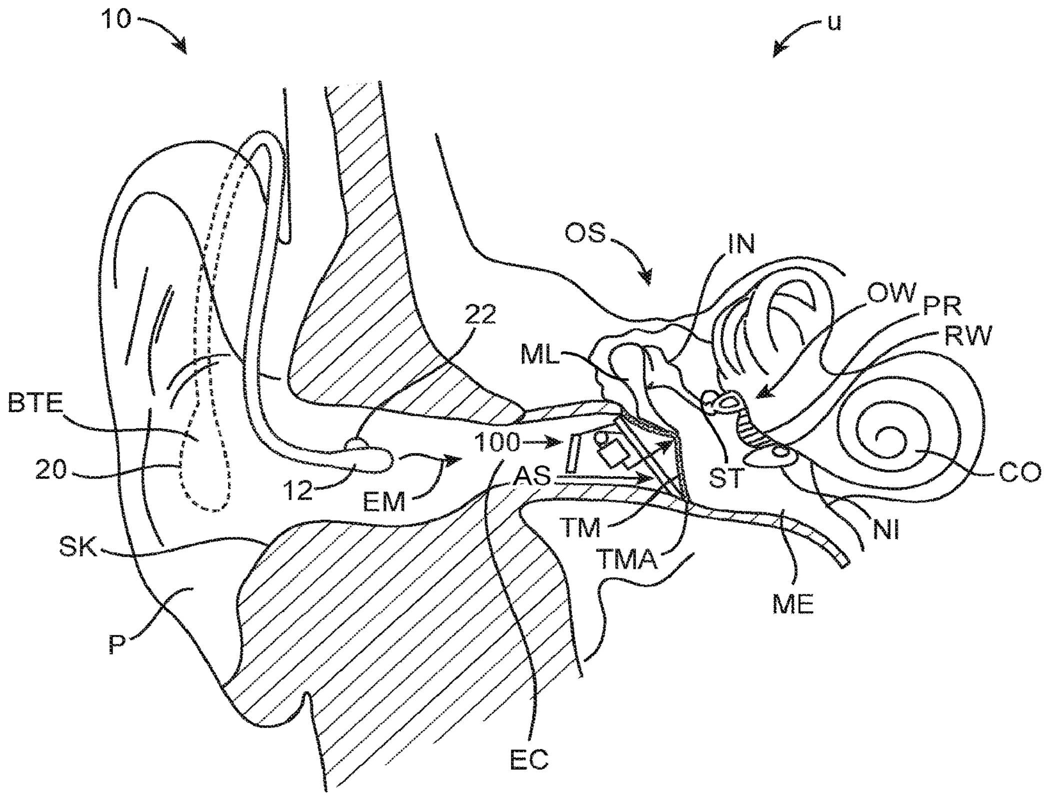
FIG. 1 shows a hearing aid system configured to transmit electromagnetic energy to an output transducer assembly, in accordance with embodiments of the present invention.

FIG. 1 shows a hearing aid system 10 configured to transmit electromagnetic energy to an output transducer assembly 100 positioned in the ear canal EC of the user. The ear comprises an external ear, a middle ear ME and an inner ear. The external ear comprises a Pinna P and an ear canal EC and is bounded medially by an eardrum TM. Ear canal EC extends medially from pinna P to eardrum TM. Ear canal EC is at least partially defined by a skin SK disposed along the surface of the ear canal. The eardrum TM comprises an annulus TMA that extends circumferentially around a majority of the eardrum to hold the eardrum in place. The middle ear ME is disposed between eardrum TM of the ear and a cochlea CO of the ear. The middle ear ME comprises the ossicles OS to couple the eardrum TM to cochlea CO. The ossicles OS comprise an incus IN, a malleus ML and a stapes ST. The malleus ML is connected to the eardrum TM and the stapes ST is connected to an oval window OW, with the incus IN disposed between the malleus ML and stapes ST. Stapes ST is coupled to the oval window OW so as to conduct sound from the middle ear to the cochlea.

The hearing system 10 includes an input transducer assembly 20 and an output transducer assembly 100 to transmit sound to the user. Hearing system 10 may comprise a behind the ear unit BTE. Behind the ear unit BTE may comprise many components of system 10 such as a speech processor, battery, wireless transmission circuitry and input transducer assembly 10. Behind the ear unit BTE may comprise many component as described in U.S. Pat. Pub. Nos. 2007/0100197, entitled "Output transducers for hearing systems"; and 2006/0251278, entitled "Hearing system having improved high frequency response", the full disclosures of which are incorporated herein by reference and may be suitable for combination in accordance with some embodiments of the present invention. The input transducer assembly 20 can be located at least partially behind the pinna P, although the input transducer assembly may be located at many sites. For example, the input transducer assembly may be located substantially within the ear canal, as described in U.S. Pub. No. 2006/0251278. The input transducer assembly may comprise a blue tooth connection to couple to a cell phone and my comprise, for example, components of the commercially available Sound ID 300, available from Sound ID of Palo Alto, Calif. The output transducer assembly 100 may comprise components to receive the light energy and vibrate the eardrum in response to light energy. An example of an output transducer assembly having components suitable for combination in accordance with embodiments as described herein is described in U.S. Pat. App. No. 61/217,801, filed Jun. 3, 2009, entitled "Balanced Armature Device and Methods for Hearing" and PCT/US2009/057719, filed 21 Sep. 2009, Balanced Armature Device and Methods for Hearing", the full disclosure of which is incorporated herein by reference.

The input transducer assembly 20 can receive a sound input, for example an audio sound. With hearing aids for hearing impaired individuals, the input can be ambient sound. The input transducer assembly comprises at least one input transducer, for example a microphone 22. Microphone 22 can be positioned in many locations such as behind the ear, as appropriate. Microphone 22 is shown positioned to detect spatial localization cues from the ambient sound, such that the user can determine where a speaker is located based on the transmitted sound. The pinna P of the ear can diffract sound waves toward the ear canal opening such that sound localization cues can be detected with frequencies above at least about 4 kHz. The sound localization cues can be detected when the microphone is positioned within ear canal EC and also when the microphone is positioned outside the ear canal EC and within about 5 mm of the ear canal opening. The at least one input transducer may comprise a second microphone located away from the ear canal and the ear canal opening, for example positioned on the behind the ear unit BTE. The input transducer assembly can include a suitable amplifier or other electronic interface. In some embodiments, the input may comprise an electronic sound signal from a sound producing or receiving device, such as a telephone, a cellular telephone, a Bluetooth connection, a radio, a digital audio unit, and the like.

In many embodiments, at least a first microphone can be positioned in an ear canal or near an opening of the ear canal to measure high frequency sound above at least about one 4 kHz comprising spatial localization cues. A second microphone can be positioned away from the ear canal and the ear canal opening to measure at least low frequency sound below about 4 kHz. This configuration may decrease feedback to the user, as described in U.S. Pat. Pub. No. US 2009/0097681, the full disclosure of which is incorporated herein by reference and may be suitable for combination in accordance with embodiments of the present invention.

Input transducer assembly 20 includes a signal output source 12 which may comprise a light source such as an LED or a laser diode, an electromagnet, an RF source, or the like. The signal output source can produce an output based on the sound input. Output transducer assembly 100 can receive the output from input transducer assembly 20 and can produce mechanical vibrations in response. Output transducer assembly 100 comprises a sound transducer and may comprise at least one of a coil, a magnet, a magnetostrictive element, a photostrictive element, or a piezoelectric element, for example. For example, the output transducer assembly 100 can be coupled input transducer assembly 20 comprising an elongate flexible support having a coil supported thereon for insertion into the ear canal as described in U.S. Pat. Pub. No. 2009/0092271, entitled "Energy Delivery and Microphone Placement Methods for Improved Comfort in an Open Canal Hearing Aid", the full disclosure of which is incorporated herein by reference and may be suitable for combination in accordance with some embodiments of the present invention. Alternatively or in combination, the input transducer assembly 20 may comprise a light source coupled to a fiber optic, for example as described in U.S. Pat. Pub. No. 2006/0189841 entitled, "Systems and Methods for Photo-Mechanical Hearing Transduction", the full disclosure of which is incorporated herein by reference and may be suitable for combination in accordance with some embodiments of the present invention. The light source of the input transducer assembly 20 may also be positioned in the ear canal, and the output transducer assembly and the BTE circuitry components may be located within the ear canal so as to fit within the ear canal. When properly coupled to the subject's hearing transduction pathway, the mechanical vibrations caused by output transducer assembly 100 can induce neural impulses in the subject which can be interpreted by the subject as the original sound input.

Figure 2A:
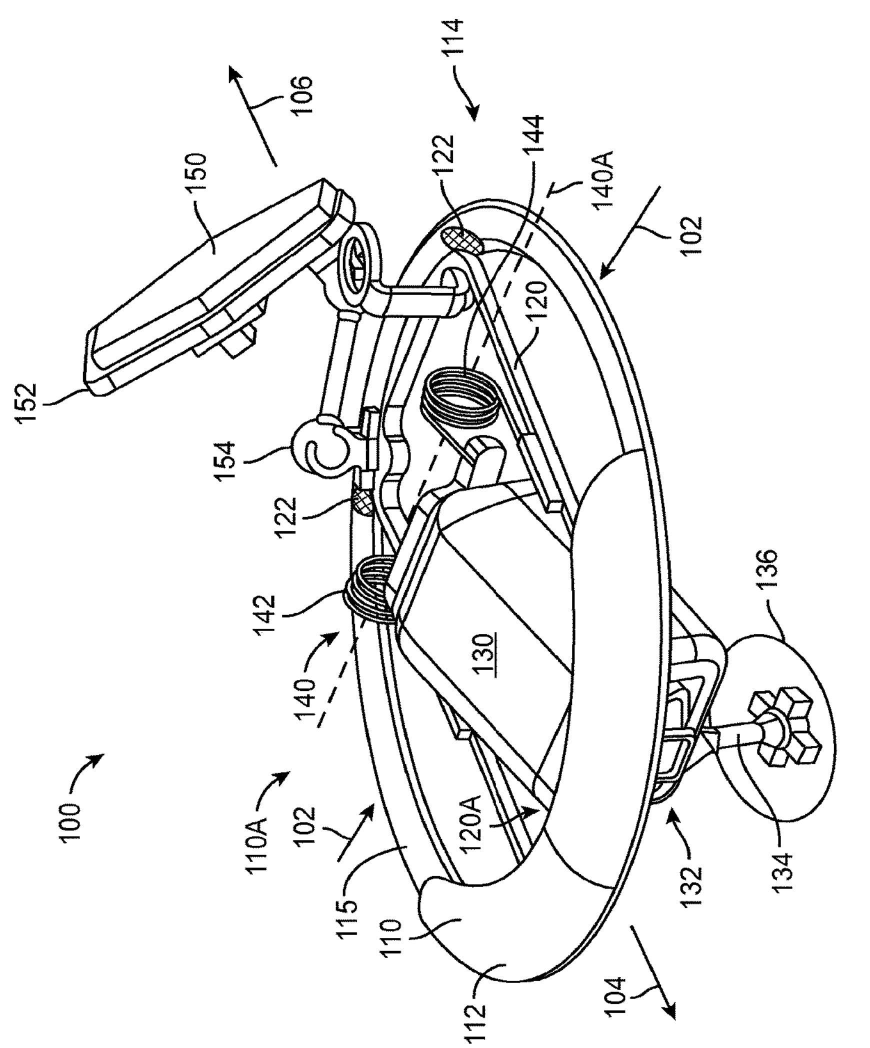
FIGS. 2A and 2B show isometric and top views, respectively, of the output transducer assembly in accordance with embodiments of the present invention.
Figure 2B:
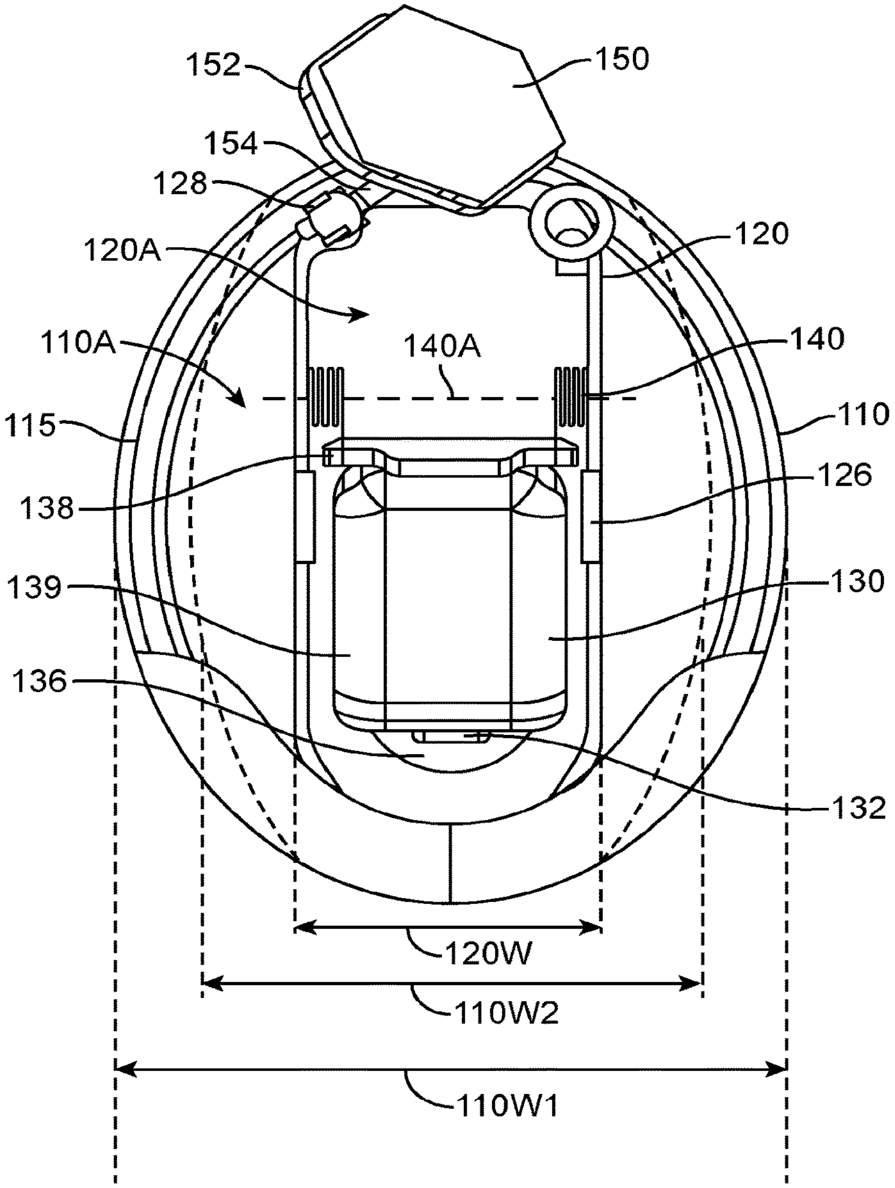

FIGS. 2A and 2B show isometric and top views, respectively, of the output transducer assembly 100. Output transducer assembly 100 comprises a retention structure 110, a support 120, a transducer 130, at least one spring 140 and a photodetector 150. Retention structure 110 is sized to couple to the eardrum annulus TMA and at least a portion of the anterior sulcus AS of the ear canal EC. Retention structure 110 comprises an aperture 110A. Aperture 110A is sized to receive transducer 130.

The retention structure 110 can be sized to the user and may comprise one or more of an o-ring, a c-ring, a molded structure, or a structure having a shape profile so as to correspond to a mold of the ear of the user. For example retention structure 110 may comprise a polymer layer 115 coated on a positive mold of a user, such as an elastomer or other polymer. Alternatively or in combination, retention structure 110 may comprise a layer 115 of material formed with vapor deposition on a positive mold of the user, as described herein. Retention structure 110 may comprise a resilient retention structure such that the retention structure can be compressed radially inward as indicated by arrows 102 from an expanded wide profile configuration to a narrow profile configuration when passing through the ear canal and subsequently expand to the wide profile configuration when placed on one or more of the eardrum, the eardrum annulus, or the skin of the ear canal.

The retention structure 110 may comprise a shape profile corresponding to anatomical structures that define the ear canal. For example, the retention structure 110 may comprise a first end 112 corresponding to a shape profile of the anterior sulcus AS of the ear canal and the anterior portion of the eardrum annulus TMA. The first end 112 may comprise an end portion having a convex shape profile, for example a nose, so as to fit the anterior sulcus and so as to facilitate advancement of the first end 112 into the anterior sulcus. The retention structure 110 may comprise a second end 114 having a shape profile corresponding to the posterior portion of eardrum annulus TMA.

The support 120 may comprise a frame, or chassis, so as to support the components connected to support 120. Support 120 may comprise a rigid material and can be coupled to the retention structure 110, the transducer 130, the at least one spring 140 and the photodetector 150. The support 120 may comprise a biocompatible metal such as stainless steel so as to support the retention structure 110, the transducer 130, the at least one spring 140 and the photodetector 150. For example, support 120 may comprise cut sheet metal material. Alternatively, support 120 may comprise injection molded biocompatible plastic. The support 120 may comprise an elastomeric bumper structure 122 extending between the support and the retention structure, so as to couple the support to the retention structure with the elastomeric bumper. The elastomeric bumper structure 122 can also extend between the support 120 and the eardrum, such that the elastomeric bumper structure 122 contacts the eardrum TM and protects the eardrum TM from the rigid support 120. The support 120 may define an aperture 120A formed thereon. The aperture 120A can be sized so as to receive the balanced armature transducer 130, for example such that the housing of the balanced armature transducer 130 can extend at least partially through the aperture 120A when the balanced armature transducer is coupled to the eardrum TM. The support 120 may comprise an elongate dimension such that support 120 can be passed through the ear canal EC without substantial deformation when advanced along an axis corresponding to the elongate dimension, such that support 120 may comprise a substantially rigid material and thickness.

The transducer 130 comprises structures to couple to the eardrum when the retention structure 120 contacts one or more of the eardrum, the eardrum annulus, or the skin of the ear canal. The transducer 130 may comprise a balanced armature transducer having a housing and a vibratory reed 132 extending through the housing of the transducer. The vibratory reed 132 is affixed to an extension 134, for example a post, and an inner soft coupling structure 136. The soft coupling structure 136 has a convex surface that contacts the eardrum TM and vibrates the eardrum TM. The soft coupling structure 136 may comprise an elastomer such as silicone elastomer. The soft coupling structure 136 can be anatomically customized to the anatomy of the ear of the user. For example, the soft coupling structure 136 can be customized based a shape profile of the ear of the user, such as from a mold of the ear of the user as described herein.

At least one spring 140 can be connected to the support 120 and the transducer 130, so as to support the transducer 130. The at least one spring 140 may comprise a first spring 122 and a second spring 124, in which each spring is connected to opposing sides of a first end of transducer 130. The springs may comprise coil springs having a first end attached to support 120 and a second end attached to a housing of transducer 130 or a mount affixed to the housing of the transducer 130, such that the coil springs pivot the transducer about axes 140A of the coils of the coil springs and resiliently urge the transducer toward the eardrum when the retention structure contacts one or more of the eardrum, the eardrum annulus, or the skin of the ear canal. The support 120 may comprise a tube sized to receiving an end of the at least one spring 140, so as to couple the at least one spring to support 120.

A photodetector 150 can be coupled to the support 120. A bracket mount 152 can extend substantially around photodetector 150. An arm 154 extend between support 120 and bracket 152 so as to support photodetector 150 with an orientation relative to support 120 when placed in the ear canal EC. The arm 154 may comprise a ball portion so as to couple to support 120 with a ball-joint. The photodetector 150 can be coupled to transducer 130 so as to driven transducer 130 with electrical energy in response to the light energy signal from the output transducer assembly.

Resilient retention structure 110 can be resiliently deformed when inserted into the ear canal EC. The retention structure 110 can be compressed radially inward along the pivot axes 140A of the coil springs such that the retention structure 110 is compressed as indicated by arrows 102 from a wide profile configuration having a first width 110W1 to an elongate narrow profile configuration having a second width 110W2 when advanced along the ear canal EC as indicated by arrow 104 and when removed from the ear canal as indicated by arrow 106. The elongate narrow profile configuration may comprise an elongate dimension extending along an elongate axis corresponding to an elongate dimension of support 120 and aperture 120A. The elongate narrow profile configuration may comprise a shorter dimension corresponding to a width 120W of the support 120 and aperture 120A along a shorter dimension. The retention structure 110 and support 120 can be passed through the ear canal EC for placement. The reed 132 of the balanced armature transducer 130 can be aligned substantially with the ear canal EC when the assembly 100 is advanced along the ear canal EC in the elongate narrow profile configuration having second width 110W2.

The support 120 may comprise a rigidity greater than the resilient retention structure 110, such that the width 120W remains substantially fixed when the resilient retention structure is compressed from the first configuration having width 110W 1 to the second configuration having width 110W2. The rigidity of support 120 greater than the resilient retention structure 110 can provide an intended amount of force to the eardrum TM when the inner soft coupling structure 136 couples to the eardrum, as the support 120 can maintain a substantially fixed shape with coupling of the at least one spring 140. In many embodiments, the outer edges of the resilient retention structure 110 can be rolled upwards toward the side of the photodetector 150 so as to compress the resilient retention structure from the first configuration having width 110W 1 to the second configuration having width 110W2, such that the assembly can be easily advanced along the ear canal EC.

FIGS. 3-1 to 3-12 show a method 300 of making resilient retention structure 110 to hold an output transducer assembly in an ear of the user. The method 300 can be performed with one or more components of an apparatus 200 to make the resilient retention structure.

The process may comprise making an anatomically accurate mold and the vapor deposition polymerization of Parylene™ onto the mold. The mold can be constructed and prepared in such a way as to provide both the dimensional accuracy of the deposited Parylene™ and the removal the Parylene™ without distortion or strain. Additionally or alternatively, the Parylene™ may comprise an integrated structural member of the finished assembly, for example when the Parylene™ is deposited on the support 120.

Formation of Negative Impression of Ear Canal

Figures 1, 3:
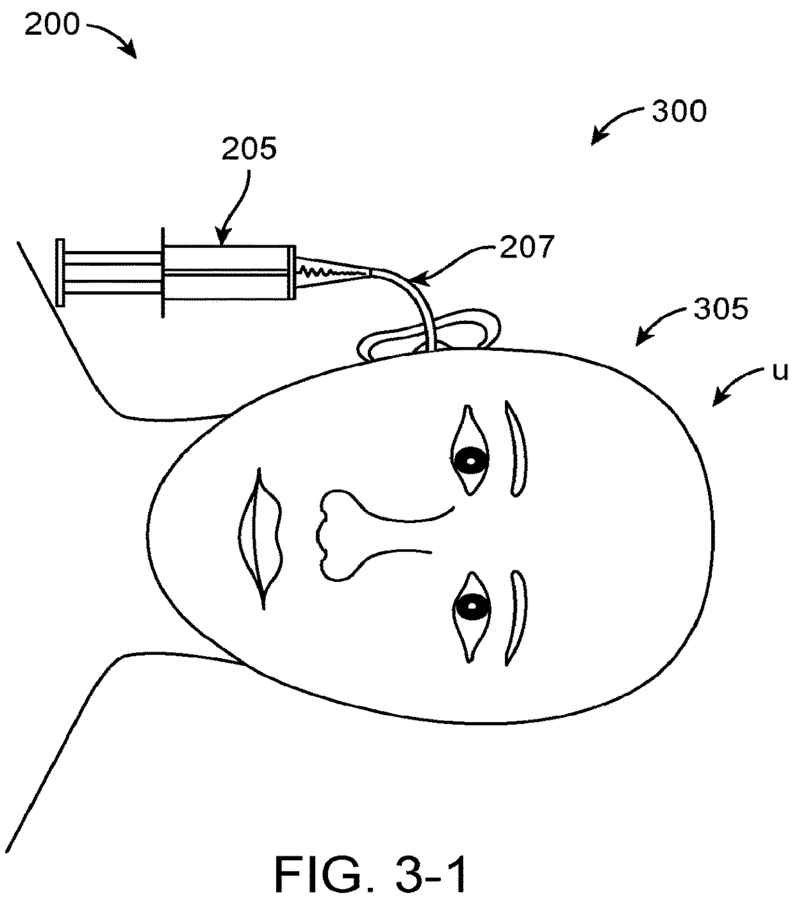

FIG. 3-1 shows an injection step 305. The process for creating an anatomically accurate, uniformly thick, and flexible platform of biocompatible material can include with the creation of a representation of the human ear canal of interest. A physician can perform this procedure in a clinical setting. A biocompatible, two-part silicone 205, for example polyvinyl siloxane hereinafter "PVS", can be dispensed into the ear canal with a dispensing tube 207 such as a bent stainless steel tube. The PVS may include mineral oil or other oil, for example.

Figures 2, 3:
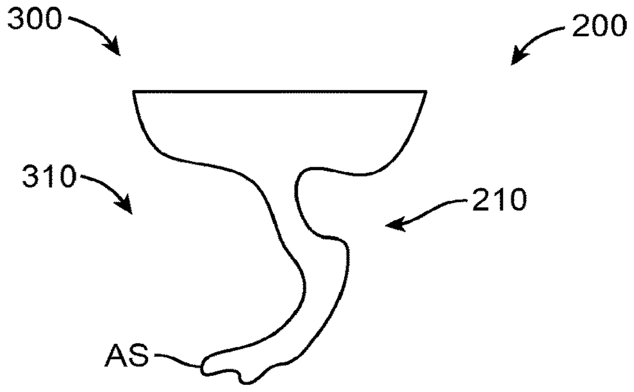
Figure 3:
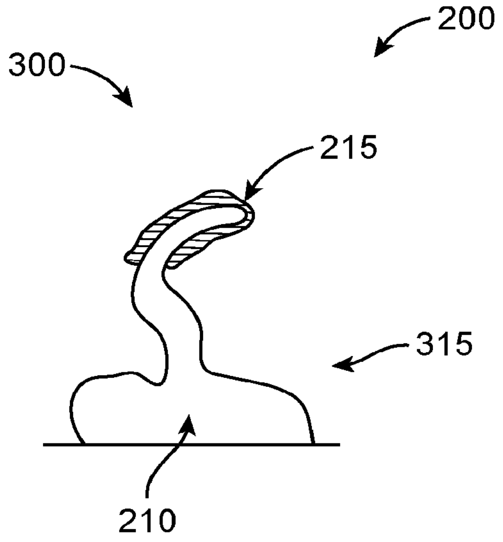

FIG. 3-2 shows a removal step 310. The PVS can be allowed to fully cure, and then be removed. The resulting negative impression 210 comprises a dimensionally accurate, customized negative representation of the ear canal (herein "PVS impression"). The PVS impression may exude mineral oil, such that the impression can be easily removed from the ear canal and eardrum, and may form an anatomically accurate impression of the anterior sulcus AS.

Formation of Positive Mold of Ear Canal

The positive mold of the ear canal can be formed based on the negative impression in many ways. The positive mold may have a shape profile corresponding to the ear canal and may comprise a substrate for vapor deposition so as to form the resilient retention structure 110 having the shape profile corresponding to the ear canal, for example with a release agent disposed between the substrate and the vapor deposition layer 115.

The material used to form the positive mold may comprise one or more of many materials such as an acrylate, an epoxy, a UV curable epoxy, a plaster, or a dental mold.

FIG. 3-3 shows a coating step 315. The PVS negative impression 210 can be coated to create a thin rigid coating 215, for example a shell, corresponding to the retention structure 110. The thin coating may comprise a resin such as an acrylate resin, for example pattern resin comprising acrylate such as polymethylmethacrylate (hereinafter "PMMA"), or a curable epoxy such as a UV curable epoxy.

Figures 3, 4:
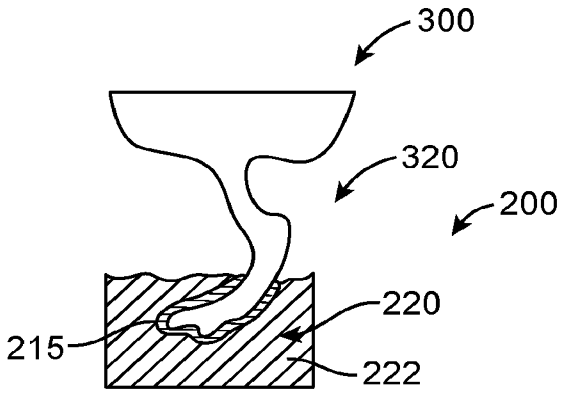

FIG. 3-4 shows an embedding step 320.

In order to provide both protection of the fragile thin shell and to provide a base for future handling, the PVS impression and coating 215 can be embedded in a small cylindrical cup 220 holding the same uncured pattern resin 222, or a UV curable epoxy or acrylate which is allowed to cure. The two-step molding process can allow the use of a large cross-sectional mold for ease of handling without the dimensional changes that may result from the larger cross section when used to create the internal mold dimensions without the shell. The PVS impression 210 can then be removed from the mold. The finished positive mold 225 is then machined flat to provide a smooth, orthogonal surface for future handling of the Parylene™ part as described herein.

The pattern resin can be replaced with a low-shrinkage acrylate, for example a UV curable acrylate, such that the mold 225 can be created by embedding the PVS impression without forming the coating. The pattern resin may comprise a shrinkage of about 3% when cured, for example, and the low shrinkage acrylate may have a shrinkage less than 1%, such that the low shrinkage acrylate or epoxy can be used to form the mold without forming the shell, for example when the low shrinkage acrylate comprises a UV curable acrylate having a shrinkage of less than 1%.

Many materials can be used to form the mold from the PVS impression, and a person of ordinary skill in the art can determine many materials based on the teachings as described herein.

The cured pattern resin may comprise a positive mold 225 of the user's ear canal.

Figures 3, 4, 5:
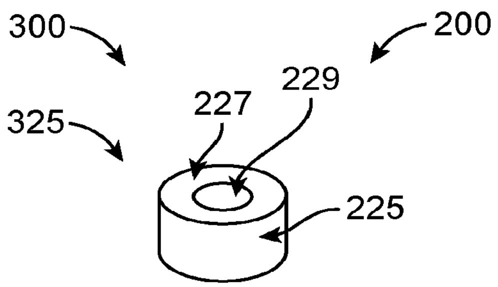
Figures 3, 4, 5, 6:
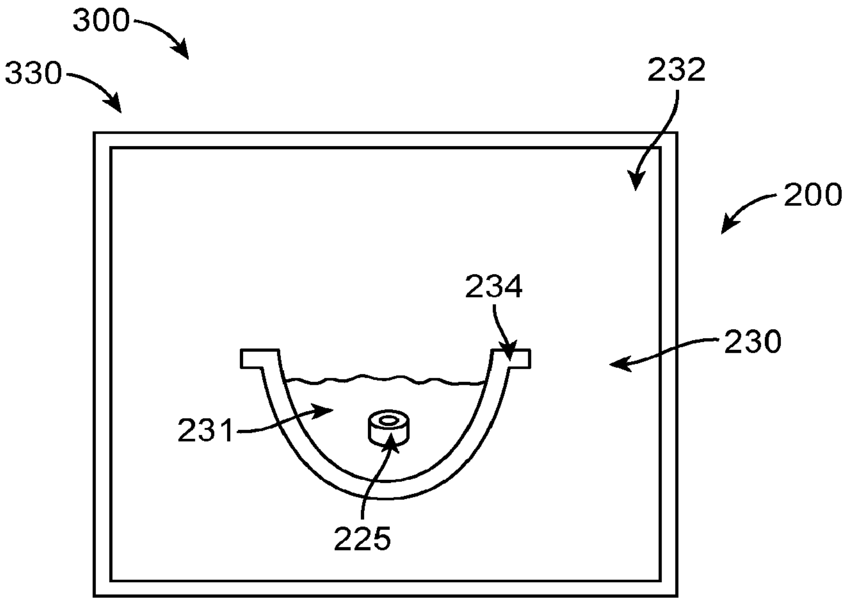
Figures 3, 4, 5, 6, 7:
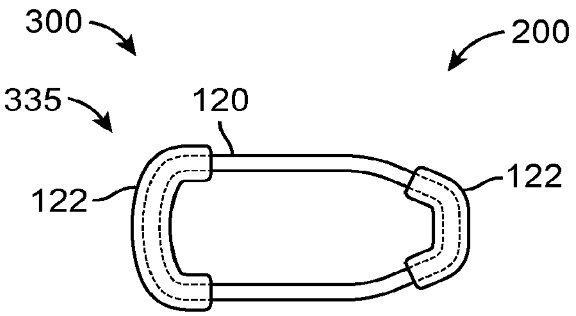
Figures 3, 4, 5, 6, 7, 8:
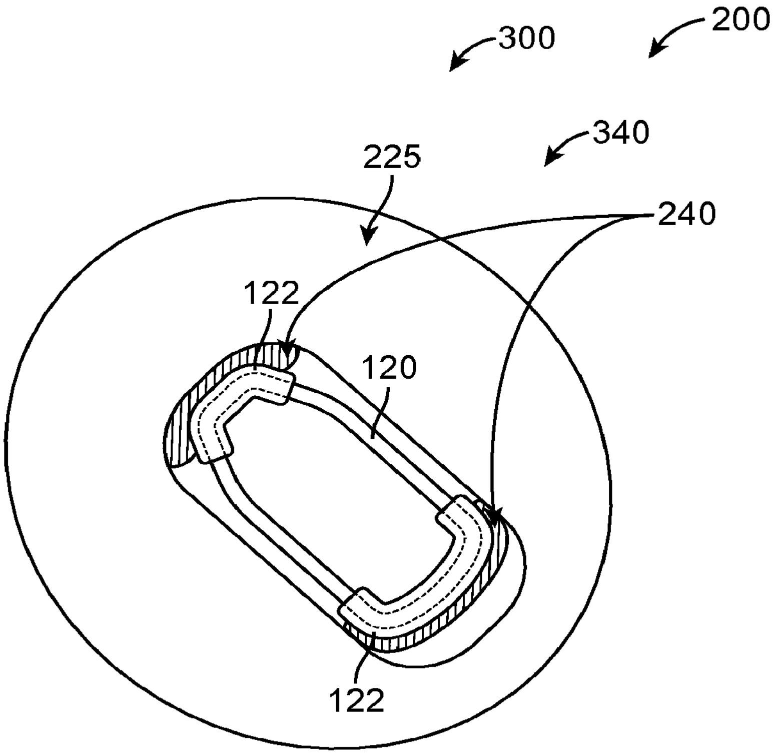
Figures 3, 4, 5, 6, 7, 8, 9:
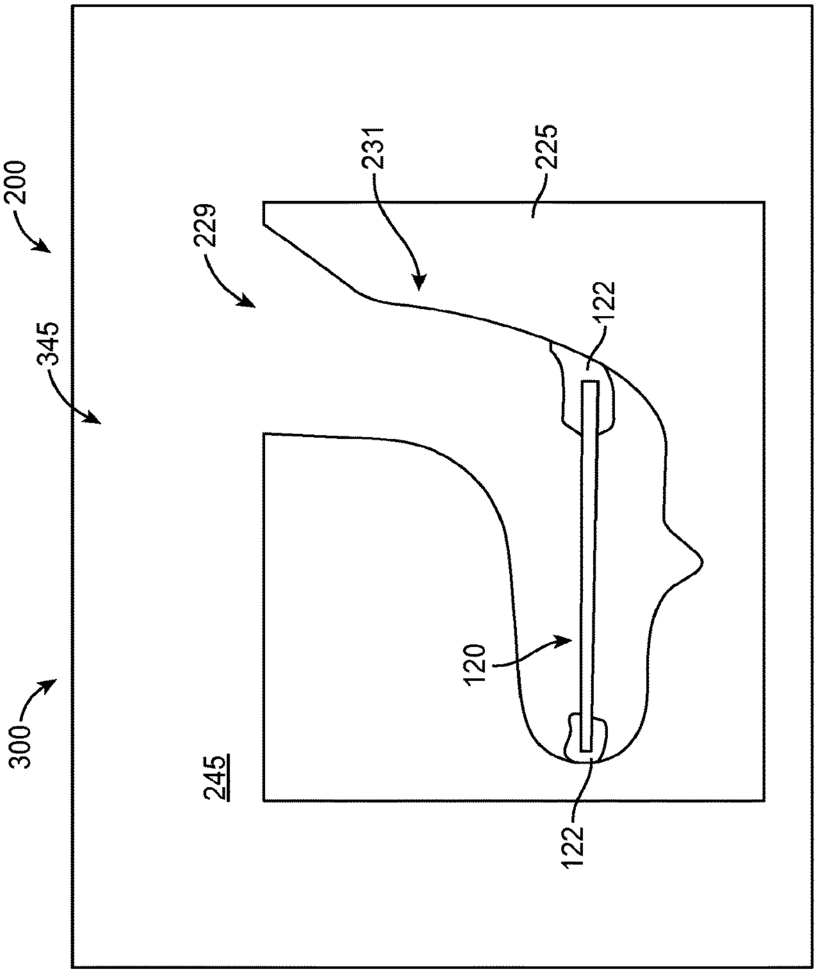

FIG. 3-5 shows a machining step 325. The cured pattern resin can be molded in a cylindrical mold. The negative impression 210 can be removed leaving a channel 229 corresponding to the ear canal, and the cured surface can be machined substantially orthogonal to the axis of the cylinder. The flat machined surface 227 can be used to handle the Parylene™ layer 115 when deposited on the mold 225 comprising the machined surface 227 and the cured coating 215.

Passivation and Removal Agent Coating of Positive Mold

FIG. 3-6 shows a submersion step 330, in accordance with embodiments of the method of FIG. 3;

The pattern resin can be porous and may also contain volatile compounds (water, air, and organic vapors), which are a result of the polymerization reaction of the pattern resin. The volatile compounds can interfere with the deposition of Parylene™. The affect of the porous surface and the volatile compounds of the mold 225 can be decreased substantially with treatment prior to the vapor deposition and polymerization. Gases can be released from the surface of the mold when the Parylene™ layer is deposited in the vacuum chamber. In order to decrease this gas release, the mold material can be passivated prior to placement into the deposition chamber. This passivation process can substantially improve the quality of the Parylene™ finished "film", as the number of pinholes formed by gas release are decreased, and the mold surface is smoothed with the release agent filling the pores near the deposition surface.

After removal of the PVS impression from the mold, the mold is placed into a bath of heated petroleum jelly such that the heated petroleum jelly comprises a liquid, for example heated to 100 degrees C. The bath of heated petroleum jelly can be provided with a container 234 comprising the heated petroleum jelly. The container 234 and mold can be placed in a vacuum chamber 232 to provide low pressure and elevated temperature. The petroleum jelly may comprise the release agent 231.

To remove the volatile compounds, a pre-deposition pump down (low pressure) time period of 2-4 hours can be used, and the mold 225 immersed in the bath can be placed in a vacuum of about 5 to 10 Torr for the 2-4 hour period, so as to inhibit formation of pinholes when the vapor is deposited and polymerized. The mold immersed in the bath can be heated when placed in the vacuum for the 2-4 hour period.

After the de-gas step is complete, the pressure is allowed to return to atmosphere while the mold remains submerged in the heated liquefied petroleum jelly. This allows many evacuated cavities within the mold 225 to be replaced with the liquefied petroleum jelly, such that petroleum jelly substantially fills the cavities and pores. The mold 225 can be removed, placed upside down so as to drain the liquefied petroleum jelly, and allowed to cool, so as to provide a substantially smooth surface to receive the Parylene™ precursor vapor and form the smooth coating and so as to release the formed coating from the smooth surface.

The petroleum jelly can be wiped at room temperature so as to provide the smooth surface for deposition of the Parylene™ precursor monomer and formation of the Parylene™.

The petroleum jelly, can be referred to as petrolatum or soft paraffin, CAS number 8009-03-8, is a semi-solid mixture of hydrocarbons, with a majority carbon numbers mainly higher than 25. The petroleum jelly may comprise a semi-solid mixture of hydrocarbons, having a melting-point usually within a few degrees of 75° C. (167° F.). Petroleum jelly can comprise a non-polar hydrocarbon that is hydrophobic (water-repelling) and insoluble in water.

Support Chassis Placement on Positive Mold

FIG. 3-7 shows a pretreatment step 335 of coating a support chassis.

After the mold 225 is removed from the petroleum jelly bath, the stainless steel support chassis can be placed into the mold. The chassis support 120 may comprise an internal support, or "skeleton", for the placement and positioning of the transducer on the finished assembly, and the placement and orientation of the chassis can be important to the final performance and positional stability of the final activated assembly.

The positional stability of the chassis within the mold can be accomplished by a two-step bumperization of the support chassis using fluorosilicone. This thin region of fluorosilicone may comprise a cushion between the stainless steel chassis and the sensitive skin of the ear canal.

Prior to placement in the mold 225, the support can be treated with a coating to protect the skin of the ear canal and the tympanic membrane of the user, and to improve adherence of the support 120 to the resilient retention structure 110. For example, the support may comprise a metallic sheet material securely connected to the resilient Parylene™ retention structure.

The ends of support 120 can be coated in many ways. For example, each end of the support 120 can be dipped in fluorosilicone to form an elastomeric bumper 122 on each end of support 120.

FIG. 3-8 shows a step 340 of coupling the coated support to the mold.

When the dip coated fluorosilicone is cured, a second coating of fluorosilicone can be applied to the ends of the support and the support can be placed in the mold. The second application 240 can be applied to each of the cured bumpers 122. The support 120 can be inserted into the mold and aligned with positive impression of the ear, for example aligned with the eardrum and anterior sulcus, so as to correspond with an intended alignment of the ear of the user. This second step application 240 of fluorosilicone can provide positional stability of the support in the mold and provide mechanical connection between the support and the Parylene™, for example with an increased surface area so as to improve adhesion. The elastomer comprising fluorosilicone disposed between the support 120 and resilient retention structure 110 can improve coupling, for example when the retention structure 110 is resiliently deformed and the support 120 retains a substantially fixed and rigid configuration when the retention structure and support are advanced along the ear canal. When the fluorosilicone application is complete and fully cured, the support chassis is very stable for the handling of the mold prior to and during the Parylene™ deposition process.

Parylene™ DEPOSITION ON POSITIVE MOLD AND SUPPORT CHASSIS

FIG. 3-9 shows a step 345 of vapor deposition of monomer precursor to the mold to form a layer 115 of Parylene™ polymer film 250. The vapor deposition may occur in a chamber 245. The Parylene™ precursor monomer enters the mold through an opening 229 corresponding to a cross section of the ear canal EC. The vapor is deposited on support 120 and bumpers 122. The bumpers 122 contact the release agent 231 deposited on the cured coating 215. The vapor deposition and Parylene™ formation process can occur at an ambient room temperature, for example when the release agent comprising petroleum jelly is a solid.

FIG. 3-9A shows the structure of Parylene™, in accordance with embodiments. Parylene™ is the trade name for members of a unique genus of polymers, which includes one or more of Parylene™ N, Parylene™ C, or Parylene™ HT among others. The resilient retention structure 110 as described herein may comprise one or more commercially available Parylene™, such as one or more of Parylene™ N, Parylene™ C, or Parylene™ HT. The thickness of the retention structure 110 can be within a range from about 2 um to about 100 um, for example within a range from about 5 to 50 um, so as to provide the custom resilient retention structure 110 from the custom acrylic mold substrate such that the retention structure can be resiliently folded by the skin tissue of the ear canal when advanced along the ear canal. Work in relation to embodiments suggests that a Parylene™ thickness within a range from about 10 to 25 um can be preferred. The modulus of the deposited layer 115 comprising Parylene™ can be at least about 200,000 PSI, for example at least about 300 PSI. Based on the teachings described herein, a person of ordinary skill in the art can determine the modulus and thickness so as to provide resilient structure 110 with suitable rigidity for advancement along the ear canal and placement against one or more of the eardrum or skin as described herein.

Parylene™ comprises a polymer having aromatic rings connected with carbon-carbon bonds. Parylene™ can be formed with deposition of monomer molecules having the aromatic rings, so as to form the Parylene™ polymer having the aromatic rings.

In accordance with embodiments described herein, Parylene™ can be formed with deposition on a substrate corresponding to a shape profile of a tissue structure of the subject, and the formed Parylene™ can unexpectedly be separated from the substrate so as to provide the resilient support having the shape profile of the subject. Parylenes™ suitable for incorporation in accordance with embodiments as disclosed herein are described on the world wide web, for example on Wikipedia. (wikipedia.org/wiki/Parylene)

Parylene™ is the trademark for a variety of chemical vapor deposited poly(p-xylylene) based polymers and derivatives thereof that can be deposited on the substrate with a release agent to form the support. The Parylene™ may comprise one or more of Parylene™ A, Parylene™ C, Parylene™, D or Parylene™.

Parylene™ C and AF-4, SF, HT can be used for medical devices and may comprise an FDA accepted coating devices permanently implanted into the body.

FIG. 3-9B shows the structure of Parylene™ C. In many embodiments, the Parylene™ comprises Parylene™ C having a hydrogen atom of the benzene ring substituted with substituted chlorine, for example at the C1 location.

Parylene™ N is a polymer manufactured from di-p-xylylene, a dimer synthesized from p-xylylene. Di-p-xylylene, more properly known as [2.2]paracyclophane, can be made from p-xylylene in several steps involving bromination, amination and elimination.

Parylene™ N may comprise an unsubstituted molecule. Heating [2.2]paracyclophane under low pressure (0.01-1 Torr) conditions can give rise to a diradical species which polymerizes when deposited on a surface. The monomer can be in a gaseous phase until surface contact, such that the monomer can access the entire exposed surface.

There are many Parylene™ derivatives, Parylene™ N (hereinafter "N Poly(p-xylylene)", hydrocarbon), Parylene™ C (hereinafter "poly(chloro-p-xylylene)", one chlorine group per repeat unit), Parylene™ D (hereinafter "poly(dichloro-p-xylylene)", two chlorine groups per repeat unit), Parylene™ AF-4 (generic name, aliphatic flourination 4 atoms), Parylene™ SF (Kisco product), Parylene™ HT (hereinafter "fluorinated poly(p-xylylene)", AF-4, SCS product), Parylene™ A (one amine per repeat unit, Kisco product), Parylene™ AM (one methylene amine group per repeat unit, Kisco product), Parylene™ VT-4 (generic name, fluorine atoms on the aromatic ring), Parylene™ CF (VT-4, Kisco product), and Parylene™ X (a cross-linkable version, not commercially available).

Parylene™ can have the following advantages: a hydrophobic, hydrophobic, chemically resistant; biostable, biocompatible coating; FDA approved, thin highly conformal, uniform, transparent coating, coating without temperature load of the substrates as coating takes place at ambient temperature in the vacuum, homogeneous surface, low intrinsic thin film stress due to its room temperature deposition, low coefficient of friction (AF-4, HT, SF). The Parylene™ coating can have a uniformity within a range from about +/−25 percent, for example.

Parylene™ Film Removal/Cutting

FIG. 3-10 shows a top view of the mold and step 350 of cutting the layer 115 of Parylene™ polymer film 250 to prepare the film for removal from the mold.

Once the Parylene™ has been deposited onto the mold/support/fluorosilicone assembly, the next step can be to remove the Parylene™ structure (herein "film") from the mold. Due to the extremely thin cross section of the Parylene™ and its relatively inelastic mechanical properties, the Parylene™ layer 115 of polymer film 250 can be subject to being permanently deformed during removal, which can compromise its dimensional accuracy as it relates to the human anatomy such that the film may no longer fit in the ear. This is where the preparation of the mold can be helpful to the successful removal of the Parylene™ film. The defect-free, smooth surface of the mold and lubricious character of the release agent comprising petroleum jelly can be helpful for a successful outcome at this step.

In order to prepare the mold for the film release, the mold is placed into an oven so as to liquefy the thin layer of petroleum jelly that separates the Parylene™ film from the acrylate mold substrate and so as to release the Parylene™ film. Alternatively or in combination, the release agent may comprise a surfactant, or polyethylene glycol (hereinafter "PEG") and the Parylene™ film can be separated from the mold with water so as to decouple the then film from the mold when the water contacts the surfactant.

The film 250 is then cut along the circumference of the machined upper surface 227 of the mold so as to provide a flat, substantially circular flange 252, which can be used as a handle with which the film can be removed from the mold.

FIG. 3-11 shows step 355 of removing the layer 115 of Parylene™ polymer film 250 from the mold with the film comprising a 3D self supporting structure and suitable for supporting with a backing material for cutting. The support 120 and the Parylene™ film comprising the resilient retention structure 110 are shown removed from the mold. The thin film can benefit from a stiff backing material in order to be accurately cut with acceptable edge condition. The film can be supported with a backing material such as polyethylene glycol (hereinafter "PEG") In order to accomplish this, the intact free film is filled with heated liquid polyethylene glycol (PEG) which hardens when it cools to room temperature as described herein. Due potentially excessive shrinkage, the film can be lightly pressurized to force the outer dimensions of the film to be maintained during the PEG cooling.

FIG. 3-12 shows a step 360 of cutting the layer 115 of polymer film 250 with a backing material, in accordance with embodiments of the method of FIG. 3.

The film can be cut into the intended shape. The film 250 can be fixed by the flat flange 252 to an X, Y, Z alignment device 264. The alignment device 264 may comprise an alignment device having six degrees of freedom, three rotational and three translational, such as a goniometer coupled to an X,Y,Z, translation stage. A planar cutting guide can then correctly oriented to the first desired cut. The outside of the PEG-filled film is then scored with a blade to cut through the film along the plane 262 of the blade guide 260. A second cut is made in the same manner, the result of which may comprise the desired shape of retention structure 110 and support 120. Alternatively to mechanical cutting, the Parylene™ coating can be cut with light such as excimer laser ablation, or other laser ablation, for example. The PEG can be dissolved with water.

The resilient Parylene™ retention structure and support 120 can be suitable combination with additional components of output transducer assembly 100 as described herein.

In some embodiments, the vapor comprises polyvinyl alcohol (PVA), or its hydrogel form (PVA-H).

Alternative to Parylene™ deposition or in combination with Parylene deposition, the deposited material may comprise one or more of a hydrogel material such as polyvinyl alcohol (hereinafter "PVA"), a sugar, cellulose, a carbon based material such as a diamond like coating or silicon based material such as SiO2. The material can be deposited in many ways such as vapor deposition, thermo deposition, radiofrequency deposition, or plasma deposition. For example, PVA-H can be blended before or after deposition with one or more other materials such as chitosan, gelatin, or starch. PVA-H can be deposited and polymerized by chemical crosslinking photocrosslinking, irradiation, or physical crosslinking, such as a freeze-thaw technique. When PVA-H is crosslinked, the cross-linked PVA-H can have stable volume and material properties. The deposited polymer can be coagulated, for example with quenching a deposited polymer solution in an aqueous nonsolvent, resulting in solvent-nonsolvent exchange and polymer precipitation.

A biocompatible nano composite material can be formed when PVA is combined with bacterial cellulose (BC) fibers. These can have the desired mechanical properties and manufacturing repeatability to make a resilient retention structure as described herein.

In many embodiments, the monomer molecules are deposited and polymerized using thermal deposition methods and using Radio Frequency deposition methods, such as plasma vapor deposition. Carbon based materials such polyethylene are compatible with such techniques.

The method 300 can be performed in many ways, and one or more of the materials may be substituted or combined with one or more materials to provide one or more of the steps as described herein. The material to provide the coating 215 on the PVS negative impression 210 can be one or more of many materials that can provide a stiff coating that retains the shape of the impression, for example with a stiff shell 215. In many embodiments, the material provides a rigid shell 215 over the PVS negative impression when cured. Suitable materials include adhesive, UV curable adhesive, epoxy, UV curable epoxy, UV curable acrylates, PMMA, and other castable resins such as epoxy, polyester, etc. The material of the coating 215 may comprise a substantially non-porous material, such as epoxy. Work in relation to embodiments indicates that UV curable adhesives such as UV curable epoxy substantially retain the shape of the negative impression 210 when cured, and that epoxies may comprises a porosity substantially less than acrylates such as PMMA. A UV cured epoxy can retain the shape of the negative impression 210, and has a sufficiently low porosity so as to be capable of use with one or more of many release agents.

The use of clear mold materials can enable visualization of components when place so as to ensure proper alignment with the tissue structures of the ear canal. For example, the photodetector can be placed within the canal of the positive mold and visualized and aligned within the canal so as to ensure alignment, for example. In many embodiments, a plurality of components are visualized within the canal, for example, the placement of one or more of the support 120, the transducer 130, the post 134, the coupling structure 136, the at least one spring 140, or the photodetector 150, and combinations thereof, can be visualized and aligned when placed in the canal of the positive mold.

In order to make the positive mold 225, the coating 215 and PVS impression 210 can be handled in many ways so as to protect of the fragile thin shell and to provide a base for future handling. The PVS impression 210 and coating 215 can be embedded in a small container, for example cylindrical cup 220, holding a flowable material similar to the material of coating 215. The flowable material can harden over the coating 215 so as to protect coating 215. The flowable material that hardens over the coating 215 may comprise one or more of resin, pattern resin, epoxy, epoxy resin, or UV curable epoxy resin, for example. In many embodiments, the flowable material comprises a UV curable resin 222 which is cured in the container, for example cup 220.

The positive mold 225 may comprise a translucent mold to allow visualization of the components placed in the positive mold, and in many embodiments mold 225 is transparent. The coating 215 may comprise a translucent material, for example a transparent material, and the material placed over the coating 215 to form mold 225 may comprise a translucent material, for example a transparent material. The positive mold 225 can be machined in many ways, and the optically transmissive material can be machined so as to provide a smooth surface permitting visualization of the components placed in the positive mold 225.

The release agent 231 provided on coating 215 to release the layer 115 of Parylene™ film 250 may comprise one or more of PEG, a hydrophilic coating, a surface treatment such as corona discharge, a surfactant, a wax, hydrophilic wax, or petroleum jelly, for example. The release agent 231 may comprise a material deposited on the surface, such as a surfactant, or a surface resulting from treatment such as corona discharge such that the surface becomes hydrophilic in response to the treatment.

In many embodiments, the coating 215 comprises a UV curable epoxy and the release agent 231 comprises a hydrophilic material, such that the coating 215 can be separated from the layer 215 with application of a solvent such as water.

In many embodiments, the coupling structure 136 comprises layer 115 of Parylene™ film 250. The release agent 231 provided on coating 215 can be configured so as to release the layer 115 of Parylene™ film 250 from positive mold 225 at a location corresponding to coupling structure 136. The layer 115 can be removed from positive mold 225, and the layer 115 can be cut so as to permit coupling structure 136 to vibrate. For example, the layer 115 can be cut so as to separate the coupling structure 136 from the retention structure 110. The coupling structure 136 comprising layer 115 can reduce the mass of the vibratory structures coupled to the umbo, can provide anatomical alignment of the coupling structure 136 to the umbo, and can be readily manufactured based on the teachings described herein, and can ensure that the coupling structure 136 remains attached to post 134.

It should be appreciated that the method 300 of making the resilient retention structure provides non-limiting examples in accordance with embodiments as described herein. A person of ordinary skill in the art will recognize many variations and adaptations based on the teachings described herein. For example, the steps of the method can be performed in any order, and the steps can be deleted, or added, and may comprise multiple steps or sub-steps based on the teachings described herein. Further the method can be modified so as to provide any retention structure or output transducer assembly as described herein and so as to provide one or more of the functions any one or more of the retention structures or assemblies as described herein.

FIG. 4 shows an assembly drawing and a method of assembling output transducer assembly 100, in accordance with embodiments of the present invention. The resilient retention structure 110 as described herein can be coupled to the support 120 as described herein, for example with bumpers 122 extending between the resilient retention structure 110 and the support 120. The resilient retention structure 110 may define an aperture 110A having a width 110AW corresponding to the wide profile configuration. The support 120 may define an aperture 120A having a width 120AW that remains substantially fixed when the resilient retention structure is compressed. The aperture 110A of the resilient retention structure can be aligned with the aperture 120A of the support. The support 120 can be affixed to resilient retention structure 110 in many ways, for example with one or more of Parylene™ vapor deposition as described herein, or with an adhesive, or combinations thereof. The resilient retention structure 110 may comprise the Parylene™ layer 115, a fluorosilicone layer 115, an O-ring sized to the user, or a C-ring sized to the user, or combinations thereof.

The support 120 can be coupled to the photodetector 150 as described herein. The support 120 may comprise mounts 128, and mount 128 can be coupled to couple arm 128 and bracket 152, such that the support is coupled to the photodetector 150.

The transducer 130 may comprise a housing 139 and a mount 138 attached to the housing, in which the mount 138 is shaped to receive the at least one spring 140. The transducer 130 may comprise a reed 132 extending from the housing, in which the reed 132 is attached to a post 134. The post 134 can be connected to the inner soft coupling structure 136.

The support 120 can be coupled to the transducer 130 with the at least one spring 140 extending between the coil and the transducer such that the inner soft coupling structure 136 is urged against the eardrum TM when the assembly 100 is placed to transmit sound to the user. The support 120 may comprise mounts 126, for example welded tubes, and the mounts 126 can be coupled to a first end of the at least one spring 140, and a second end of the at least one spring 140 can be coupled to the transducer 130 such that the at least one spring 140 extends between the support and the transducer. The spring has a spring constant corresponding approximately to a mass and distance from the pivot axis of the coil spring to the inner soft coupling structure 136 such that the spring urges the inner soft coupling structure toward the eardrum TM within a range of force from about 0.5 mN to about 2.0 mN when the resilient retention structure 110 is placed against one or more of the eardrum, the eardrum annulus or the skin of the ear canal wall, for example skin of an anterior sulcus define with the ear canal wall. The coil spring may comprise a torsion spring, and the torsion spring constant can be within a range from range from 0.1e-5 to 2.0e-4 mN*m/rad, for example within a range from about 0.5e-5 N-m/rad to about 8e-5 N-m/rad. This range can provide sufficient force to the inner support so as to maintain coupling of the inner support to the eardrum when the head of the user is horizontal, for example supine, and when the head is upright, for example vertical.

The resilient retention structure and the support can be configured in many ways so as a resistance to deflection within a range from about 1 N/m to about 10,000 N/m, for example within a range from about 250 N/m to about 10,000 N/m. The resistance to deflection within this range can provide sufficient stiffness to the retention structure 110 to support the transducer with the retention structure and so as to allow the retention structure to deflect inward when advanced into the ear canal so as to comprise the narrow profile configuration when the retention structure 110 slides along the ear canal, for example. In many embodiments, the resistance to deflection of the retention structure 110 coupled to support 120 is between the resistance to deflection of the ear canal and the resistance to deflection of the eardrum. The resistance to deflection within this range provides sufficient support to displace the eardrum and enough flexibility to permit the retention structure 110 to transform from the wide profile configuration to the narrow profile configuration as described herein when advanced into the ear canal.

Figure 5A:
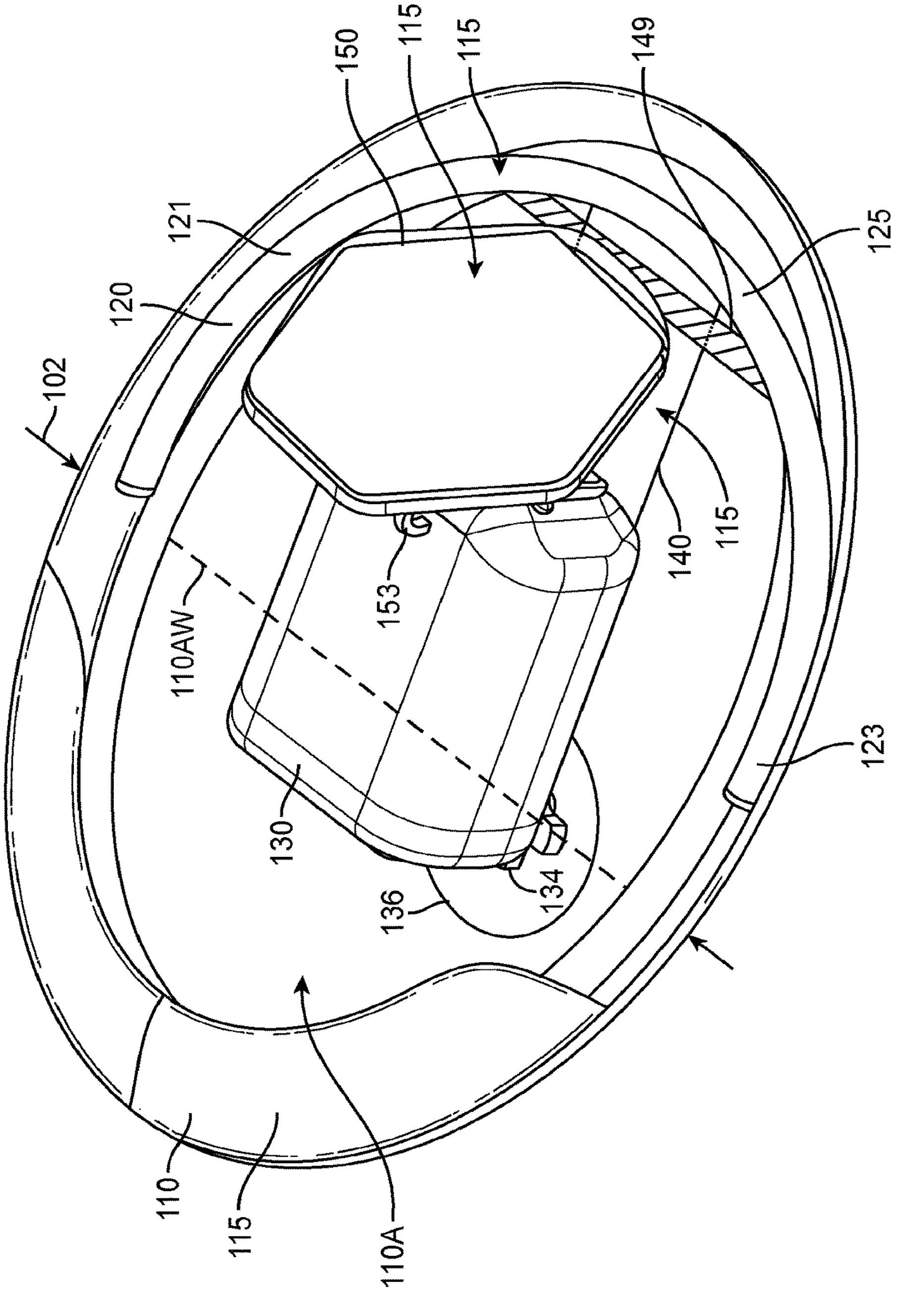
FIGS. 5A and 5B show top and bottom views, respectively, of a retention structure comprising a stiff support extending along a portion of the retention structure, in accordance with embodiments of the present invention.
Figure 5B:
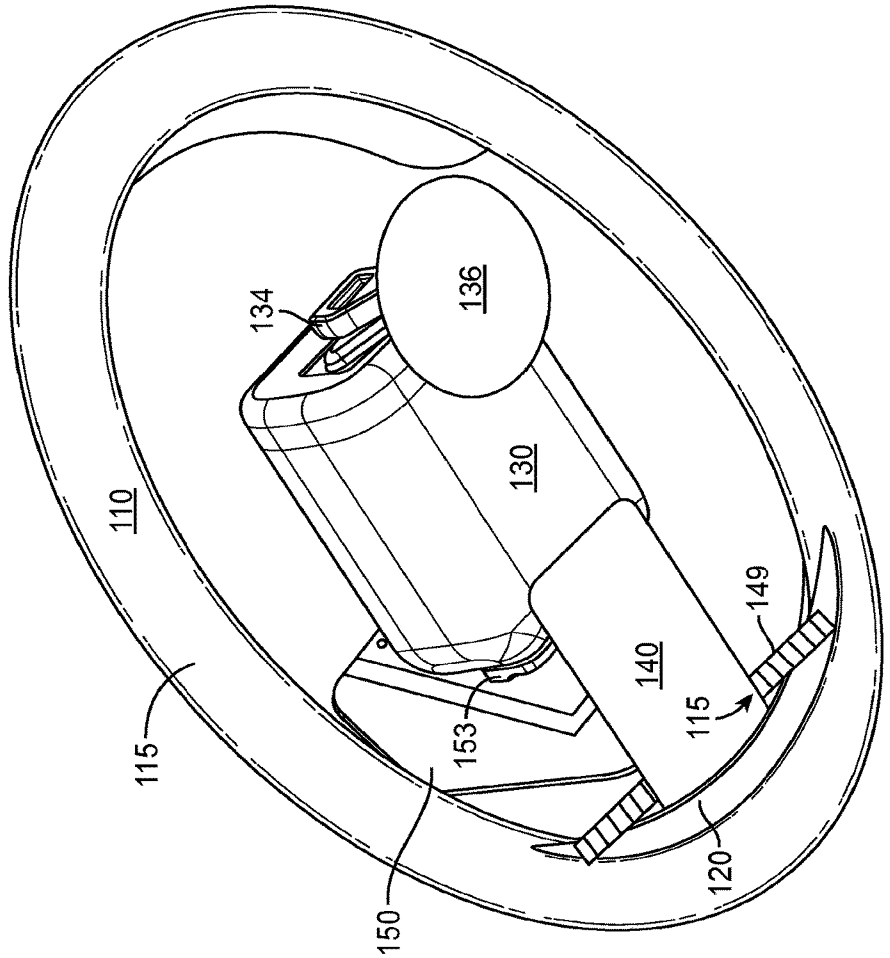

FIGS. 5A and 5B show top and bottom views, respectively, of an output transducer assembly 100 having a retention structure 110 comprising a stiff support 120 extending along a portion of the retention structure. The stiff support 120 may comprise a pair of arms comprising a first arm 121, a second arm 123 opposite the first arm, and an intermediate portion 125 extending between the first arm and the second arm. The stiff support 110 may comprise the resilient spring 140 coupled to the intermediate portion 125, for example. In many embodiments, the resilient spring and stiff support 120 comprise an integrated component such as an injection molded unitary component comprising a modulus of elasticity and dimensions so as to provide the resilient spring 140 and the stiff support 110.

The stiff support 120 and resilient spring 140 can be configured to couple the output transducer 130 to the eardrum TM when the retention structure is placed. The resilient spring 140 can be attached to the stiff support 120, such that the resilient spring 140 directly engages the stiff support 120. The stiff support 120 can be affixed to the resilient spring 140 so as to position the structure 136 below the retention structure 110, such that the structure 136 engages the tympanic membrane TM when the retention structure 110 is placed, for example on the eardrum annulus TMA. The resilient spring 140 can be configured to provide an amount of force to the eardrum when placed.

The stiff support can be configured in many ways so as to comprise the stiffness capable of deflection when placed and resistance to deflection to couple the output transducer 130 to the eardrum TM. The stiff support 120 may comprise one or more of many materials such as polymer, cured epoxy, silicone elastomer having a suitable rigidity, biaxially-oriented polyethylene terephthalate (hereinafter "BoPET", commercially available under the trademark Mylar™), metal, Polyether ether ketone (hereinafter "PEEK"), thermoplastic, shape memory material, nitinol, thermoplastic PEEK, shape memory PEEK, thermoplastic polyimide, acetal, Parylene™, and combinations thereof, for example. These polymer materials can be crosslinked to enhance their resistance to long term creep. The stiff support material may comprise a modulus, tensile strength and dimensions such as a cross-sectional diameter and length so as to provide the stiffness capable of deflection when placed and resistance to deflection to couple the output transducer.

The resilient spring 140 can be configured in many ways so as to comprise the resistance to deflection and force in response to displacement so as to couple the output transducer 130 to the eardrum TM. In many embodiments, the resilient spring 140 comprises a cantilever, in which the cantilever is fixed on a first end to the stiff support 120 and affixed to the output transducer 130 on an opposite end. The spring 140 may comprise one or more of many materials such as polymer, cured epoxy, elastomers, Mylar™, metal, Polyether ether ketone (hereinafter "PEEK"), thermoplastic, shape memory material, nitinol, thermoplastic PEEK, shape memory PEEK, and combinations thereof, for example. The resilient spring material may comprise a modulus, tensile strength and dimensions such as a cross-sectional diameter and length so as to provide the stiffness capable of deflection when placed and resistance to deflection to couple the output transducer.

The stiff support 120 and resilient spring 140 may comprise similar materials, and may comprise substantially the same material in many embodiments, for example.

The coupling structure 136 many comprise one or more of many materials as described herein. For example the coupling structure 136 may comprise a soft material such as an elastomer, for example. Alternatively, the coupling structure 136 may comprise a stiff material, for example a layer of Parylene™ film as described herein. The coupling structure 136 may comprise layer 115 deposited on the positive mold, for example. The Parylene™ layer can be cut as described herein so as to provide the coupling structure 136, for example. Alternatively, the coupling structure may comprise a curable material, for example a UV curable epoxy.

In many embodiments, the assembly 100 comprises a biasing structure 149 coupled to the stiff support 120 and the resilient spring 140 to position the structure 136 for engagement with the eardrum. The at least one spring 140 may comprise a resilient cantilever beam, for example a spring having a size and thickness as described herein. The biasing structure can be configured in many ways, and may comprise a shim or spacer, for example. The biasing structure 149 can be placed between the stiff support 120 and resilient spring 140 so as to deflect the spring and position the structure 136 to engage the eardrum TM. For example, the biasing structure 149 can be placed on a lower surface of stiff support 120 and on an upper surface of resilient spring 140 so as to deflect the spring. The biasing structure coupled directly to the stiff support 120 and resilient spring 140 can inhibit creep of the structure 136 relative to retention structure 110 so as to maintain coupling of the structure 136 to the eardrum when placed. In many embodiments, the biasing structure is adjusted to deflect the resilient spring 140 prior to or subsequent to deposition of the layer 115, such that the layer 115 can lock the biasing structure in place.

The photodetector 150 can be attached to the output transducer 130 with a mount 153. The photodetector and output transducer can deflect together when the biasing structure 149, for example a spacer, is adjusted to couple the output transducer 130 and the structure 136 to the tympanic membrane TM.

In many embodiments, the components are assembled in the mold and coated with Parylene™. The photodetector 150 can be placed in the mold and coated with one or more components of output transducer assembly 100. The layer 115 of film 250 may comprise a translucent material that can be deposited on the light receiving surface of the photodetector 150. A substantial amount of light can be transmitted through the coating and received with the photodetector to provide the output signal to the user. Parylene™ comprises a light transmissive material such that the coating can be any desirable thickness so as to provide strength to assembly 100. The resilient spring 140 can be coated with the layer 115, for example the layer Parylene™ film 250 as described herein. Each of the components of the output transducer assembly 100 can be coated with the layer 115 of Parylene™ film, for example, so as to provide a protective coating and form the resilient retention structure 110.

FIG. 5A1 shows an integrated component 400 comprising the stiff support 120 and resilient spring 140. The integrated component 400 can be formed in many ways. The integrated component can be formed by one or more of placing a flowable material in a mold, curing a flowable material, or an injection molding, and combinations thereof. The integrated component 400 may comprise a modulus of elasticity and dimensions so as to provide the resilient spring 140 and the stiff support 110 based on the cross-sectional dimensions and length of the spring 140 and cross-sectional dimensions and length of stiff support 140.

FIGS. 5A2 and 5A3 show cross-sectional views of the resilient spring 140 and the stiff support 120, respectively. The resilient spring 140 may comprise a leaf spring having a thickness 140T and a width 140W, for example. The stiff support 120 may comprise a cross-sectional dimension 120D, for example. The thickness 140T may be less than a cross-sectional dimension of the stiff support 120 and a width greater than the cross-sectional dimension of the stiff support. For example, the leaf spring may have a thickness less than a cross-sectional diameter of the stiff support 120 and a width greater than the cross-sectional diameter of the stiff support. Alternatively, the stiff-support may have non-circular cross-sectional dimensions, such as oval, square, or rectangular, for example.

FIGS. 5A4 and 5A5 show a top view and a side view, respectively, of a stiff support 120 comprising a graspable projection 410 that may be used to place the output transducer assembly in the ear canal. The projection 410 can be affixed to the stiff support 120. The at least one spring 140 may comprise a resilient spring having a width and thickness as described herein and can be affixed to the stiff support 120. The at least one spring 140 may comprise a cantilever spring affixed to stiff support 120 on one end and supporting the transducer on the other end, for example. Alternatively or in combination, the projection 410 may be detachable from the stiff support 120. In many embodiments, the integrated component 400 comprises the resilient spring 140, the stiff support 120, and the projection 410. The integrated component 400 can be made in one or more of many ways as described herein, and may comprise substantially the same material for each of the stiff support 120, the resilient spring 140 and the projection 410.

FIG. 5B1 shows a lower surface structure 136 positioned a distance 149D beneath the lower surface of retention structure 110. The distance 149D may comprise a sufficient distance, for example about 1 mm such that structure 136 can engage the eardrum TM with movement of the eardrum, for example movement in response to pressure change Changes in atmospheric pressure can result in displacements of the umbo of about 1 mm, for example. The amount of displacement for sound can be about 1 um, for example. The resilient spring structure 140 can be configured so as to deflect about 1 mm and provide a force to the eardrum TM, for example about 5 mN. The deflection of the coupling structure 136 at the umbo can be about 3 mm during placement of the device, and the at least one spring 140 can be configured to deflect at least about 3 mm, for example.

FIG. 5B2 shows a component of the output transducer assembly 100 retained between a first layer 115A and a second layer 115B. The layer 115 may comprise the first layer 115A and the second layer 115B, for example. Any one or more of the components of the transducer assembly 100 can be placed on the first layer 115A, and the second layer 115B applied so as to affix the one or more components between the first layer 115A and the second layer 115B. For example, the one or more components can be sandwiched between the first layer 115A and the second layer 115B so as to retain the one or more components between the first layer and the second layer, which each may comprise Parylene™. In many embodiments, the stiff support 110 can be retained between a first layer 115A and a second layer 115B of the retention structure 115B. The first layer 115A and the second layer 115B may increase the stiffness of the stiff support 120 when retained between layers, for example.

In many embodiments, the stiff support 120 and resilient retention structure 110 can be resiliently deflected when inserted into the ear canal EC. To place the retention structure 110 on the surface of one or more of the eardrum TM, the eardrum annulus TMA, or the bony portion BP of the ear canal, it can be helpful, and in some instances necessary, for the retention structure to deflect from a wide profile configuration having a first width 110W 1 to an elongate narrow profile configuration having a second width 110W2 when advanced along the ear canal EC as described herein. The stiff support 120 can be configured to deflect inward to provide the narrow profile configuration, and configured with sufficient resilience so as to return to the wide profile configuration having the first width when placed. The stiff, deflectable support 120 may also comprise sufficient stiffness so as to couple the output transducer 130 to the retention structure 110 so as to distribute force of the transducer substantially along the retention structure 110 and transmit force from the resilient spring 140 to locations away from resilient spring 140. This distribution of force to locations away from the resilient structure 140 sufficient surface area of retention structure 110 can allow the retention structure 110 to the couple the output transducer 130 to the eardrum with a surface tension of a coupling agent such as an oil, for example.

The first layer 115A may be formed with film 250 as described herein. The components can be placed in the positive mold on the first layer 115A, which may comprise a translucent layer, for example a transparent layer, so as to allow placement within the positive mold transparent block 400 as described herein. The second layer 115B can be deposited on positive mold having the components placed on the first layer.

Figure 6A:
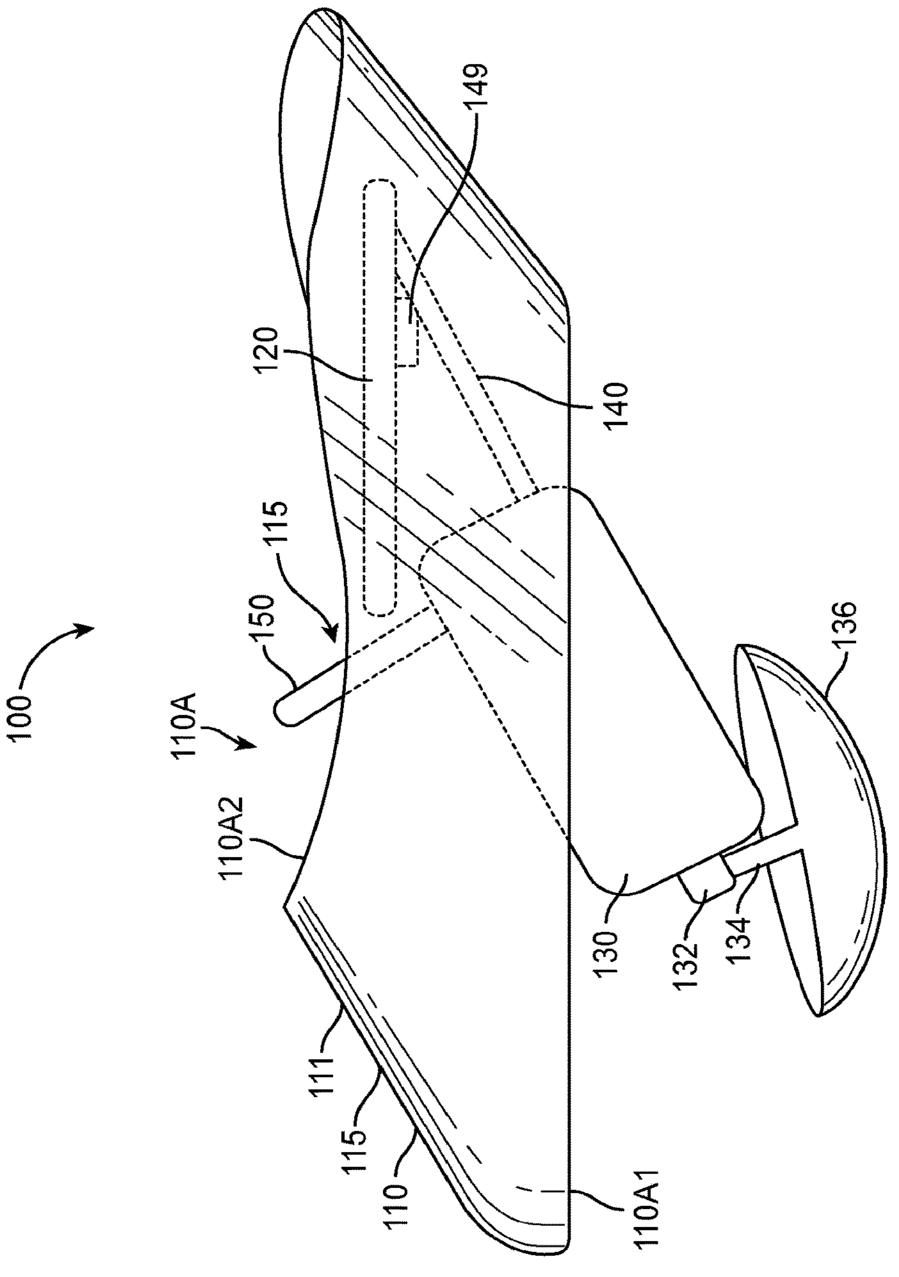
FIGS. 6A and 6B show side and top views, respectively, of a resilient tubular retention structure comprising a stiff support extending along a portion of the resilient tubular retention structure, in accordance with embodiments of the present invention.
Figure 6B:
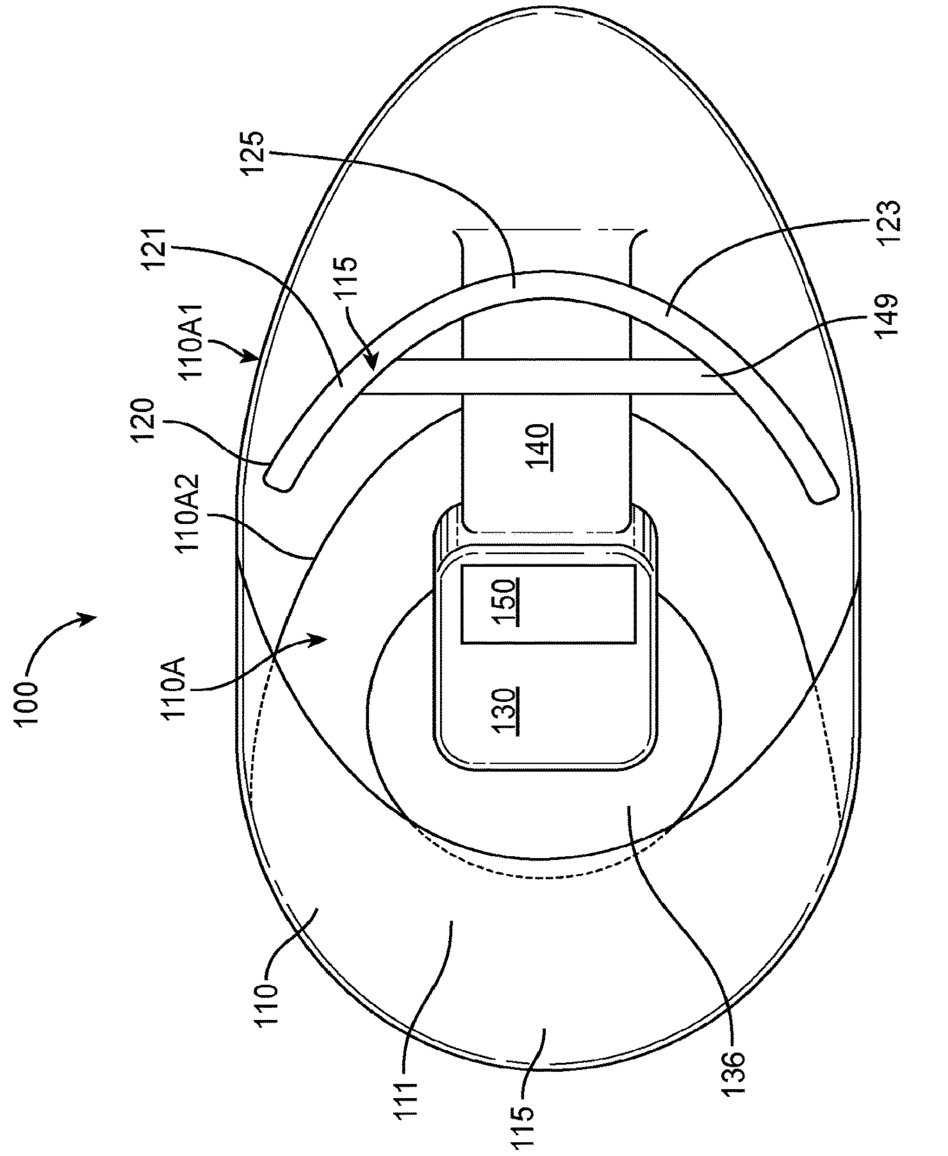

FIGS. 6A and 6B show side and top views, respectively, of a resilient retention structure comprising a stiff support extending along a portion of the resilient tubular retention structure. The stiff support 120 may comprise a pair of arms comprising a first arm 121, a second arm 123 opposite the first arm, and an intermediate portion 125 extending between the first arm and the second arm. The retention structure 110 comprises a curved portion, for example an arcuate portion 111, so as to engage the ear canal wall opposite the eardrum TM. The curved portion such as arcuate portion 111 can improve stability of the retention structure 110 in the ear canal, and provide improved coupling of the transducer 130 to the eardrum TM so as to decrease reliance on oil, for example. The curved portion such as arcuate portion 111 provides a structure opposite the tympanic membrane TM, and provides a second region on an opposite side of the ear canal to which the retention structure 110 and transducer 130 can couple. The retention structure and arcuate portion 111 comprise the layer 115 of material comprising Parylene™ film 250, such that the retention structure comprising arcuate portion 111 is shaped to the ear canal EC of the user as described herein.

The resilient retention structure 110 can engage one or more of the bony portion BP of the ear canal wall, the eardrum annulus TMA, the eardrum TM. In many embodiments, the leading end opposite the stiff support 120 can extend into the anterior sulcus when placed. The retention structure 110 may comprise a substantially tubular portion of the film 250 deposited in the ear canal mold. The substantially tubular portion may comprise a medial cut edge 110A1 and a lateral cut edge 110A2. The cut edge 110A1 and the cut edge 110A2 may define ends of the substantially tubular cut portion of the film 250. The substantially tubular portion may comprise an axis, and the cut edge 110A1 and the cut edge 110A2 can be cut oblique to the axis. Aperture 110A can extend through the substantially tubular retention structure 110.

Figure 7A:
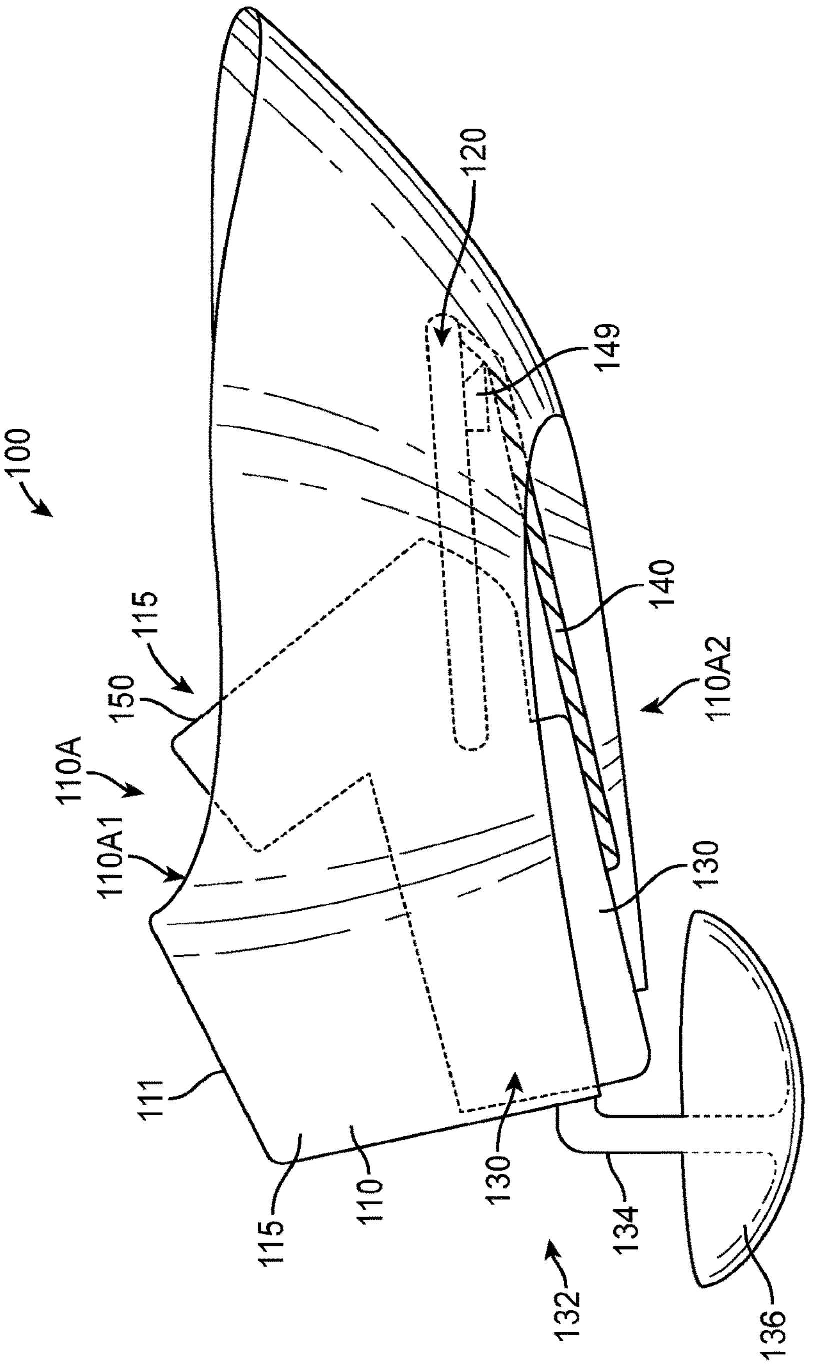
FIGS. 7A, 7B and 7C show side, top and front views, respectively, of a resilient retention structure comprising an arcuate portion and a stiff support extending along a portion of resilient retention structure, in accordance with embodiments of the present invention.
Figure 7B:
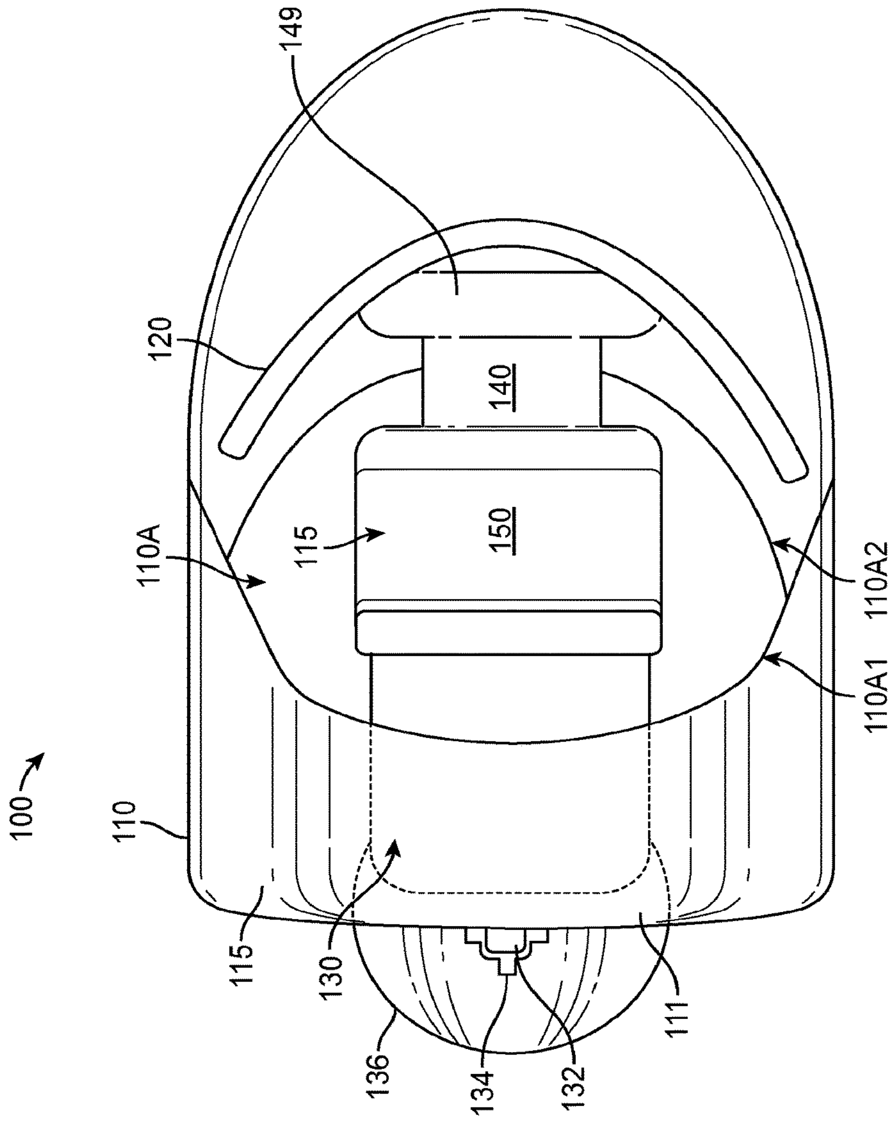
Figure 7C:
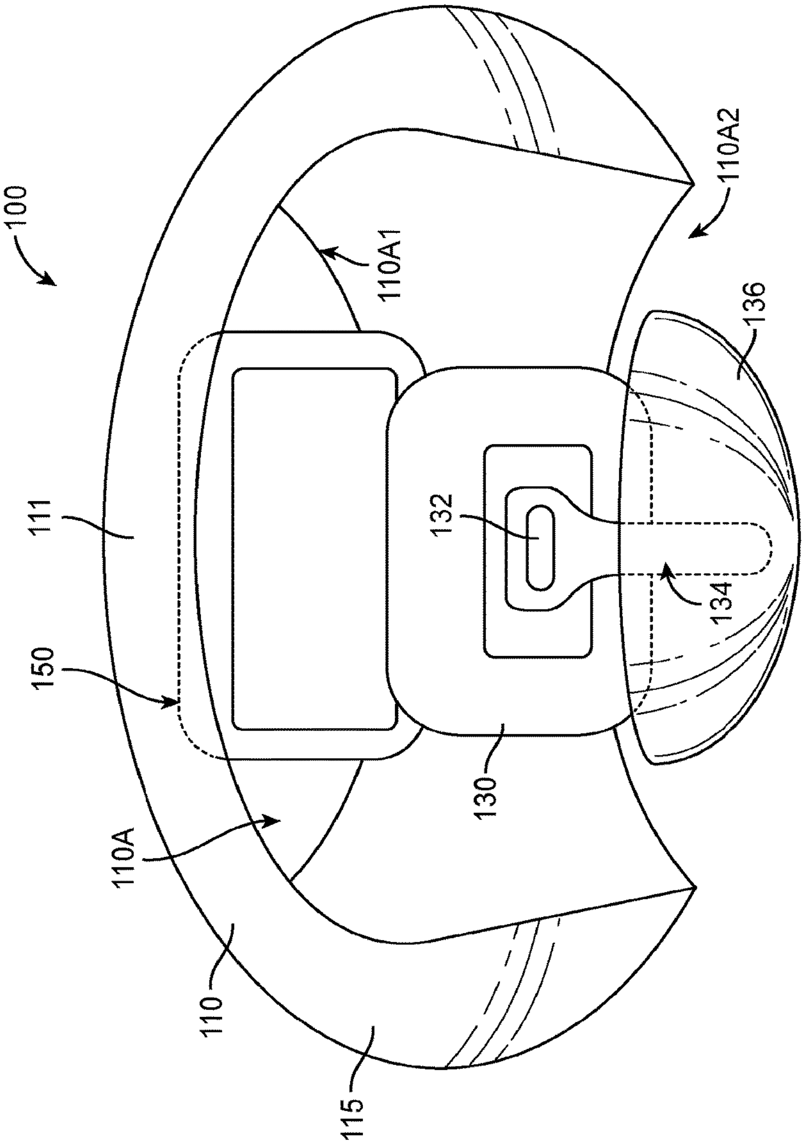

FIGS. 7A, 7B and 7C show side, top and front views, respectively, of an output transducer assembly 100 having a resilient retention structure 110 comprising curved portion such as an arcuate portion 111 and a stiff support 120 extending along a portion of the resilient retention structure. The retention structure 110 comprises a curved portion such as an arcuate portion 111 to engage the ear canal wall opposite the eardrum TM similar to the arcuate structure of FIGS. 6A and 6B. However, the portion extending into the anterior sulcus may be cut away. Work in relation to embodiments indicates that the anterior sulcus AS can be difficult to view, and truncation of the medial end of the film 250 can shape the retention structure 110 such to inhibit placement of the retention structure 110 in the anterior sulcus AS. The curved portion such as arcuate portion 111 can provide substantially coupling of the transducer to the bony portion BP of the ear canal EC wall opposite the eardrum TM. The stiff support 120 may provide provides sufficient stiffness so as to pivotally couple transducer 130 to the canal wall with the curved portion such as arcuate portion 111.

The retention structure 110 can be molded as described herein so as to comprise a thin layer 115 of material corresponding tubular portion of the ear canal. An aperture 110A can extend through the tubular portion. The aperture 110A can be defined with a first cut profile 110A1 and the second cut profile 110A2 of the tubular section of Parylene™.

The resilient retention structure 110 may comprise enough stiffness so as to couple the arcuate portion to the ear canal wall opposite tympanic membrane TM to the transducer 130.

The embodiments illustrated in FIGS. 6A to 7C show examples of retention structures, and the retention structure 110 may comprise a shape intermediate to FIGS. 6A-6B and FIGS. 7A-7C, for example. In many embodiments, the layer 115 comprises a tubular structure, and the shape of retention structure 110 depends upon the first cut profile 110A and the second cut profile 110B, for example.

Figure 8A:
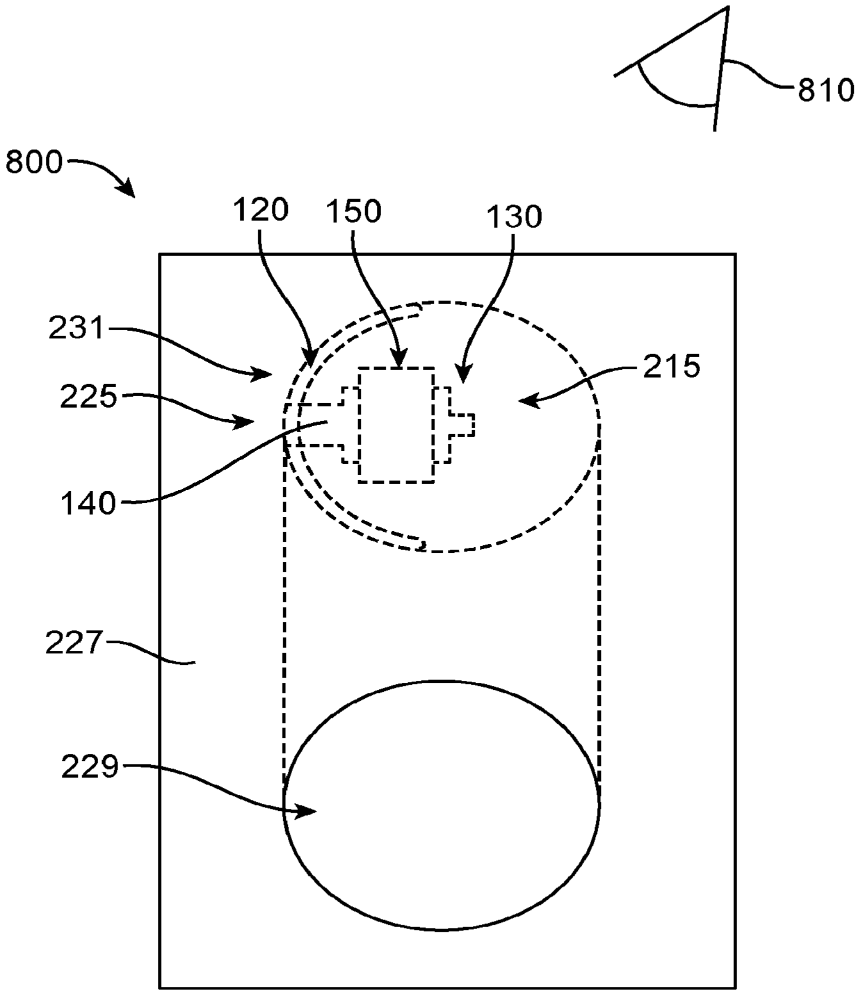
FIG. 8A shows components of an output transducer assembly placed in a transparent block of material comprising a positive mold of the ear canal and eardrum of a patient, in accordance with embodiments of the present invention.

FIG. 8A shows components of an output transducer assembly 100 placed in a transparent block 800 of material comprising the positive mold 225 of the ear canal and eardrum of the patient. The transparent block 800 may comprise the cured coating 215, the flat machined surface 227 and the release agent 231. The components placed in the transparent block 800 comprising the transparent mold 225 of the ear canal and eardrum may comprise one or more of the transducer 130, the photodetector 150, the at least one spring 140, or the support 120, and combinations thereof. The transparent block 800 permits the components placed in the block 800 to be viewed by an eye 810 of an assembler 810. The assembler may be a person or a machine such as a robotic arm. The Parylene™ can be deposited before, or after the components have been placed, or both before and after the components have been placed so as to sandwich the components between layers of Parylene™ film 250. The photodetector can be placed in the mold 225 such that Parylene™ is coated on the detector and light transmitted through the Parylene™ when the output transducer assembly 100 is placed in the ear and used. In addition to providing the retention structure 110, the sealing of the components can provide reliability and optical transmission through the protective coating.

Figure 8B:
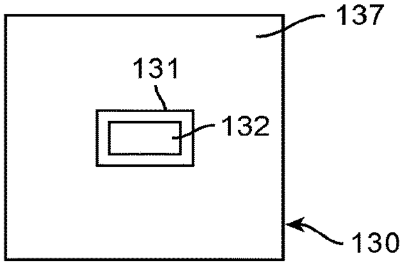
FIG. 8B shows a transducer configured to receive a vapor deposition coating, in accordance with embodiments of the present invention.

FIG. 8B shows a transducer 130 configured to receive a layer of a coating deposited with a vapor as described herein.

Figure 8C:
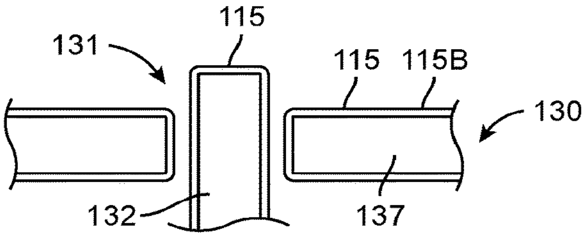
FIG. 8C shows the transducer of FIG. 8B with a deposited layer, in accordance with embodiments of the present invention.

FIG. 8C shows the transducer of FIG. 8B with a deposited layer.

The transducer 130 may comprise an opening 131 formed in the casing 137 of the output transducer 130. The reed 132 can extend through the opening 131 to couple to the post as described herein. The deposited layer 115 may comprise the second layer 115B, for example when the components are placed on first layer 115A. The vapor can pass through the opening 131 to form layer 115 on the reed. The opening 131 can be sized so as to decrease the thickness of the layer 115B deposited on the reed 132. Work in relation to embodiments as described herein indicate that layer 115 can affect tuning of the reed 132. By sizing the opening 131 to decrease the thickness of the layer 115, the output transducer 130 can be used with the coating 115B, for example.

In many embodiments, the opening 131 is sized to inhibit passage of a liquid, for example water or oil, through the opening 131. The opening 131 can be sized based on the contact angle of the liquid, so as to inhibit passage. For layer 115 providing a steep contact angle, the opening 131 can be larger than for a layer 115 providing small contact angle.

Figure 8D:
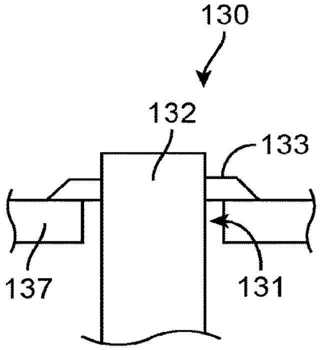
FIG. 8D shows the transducer of FIG. 8B with a blocking material to inhibit formation of the deposited layer on the reed of the transducer, in accordance with embodiments of the present invention.

FIG. 8D shows the output transducer 130 of FIG. 8B with a blocking material 133 to inhibit formation of the deposited layer on the reed 132 of the transducer. The blocking material may comprise the backing material as described herein, for example PEG, such that the Parylene™ deposited on the blocking material can be cut away.

Figure 8E:
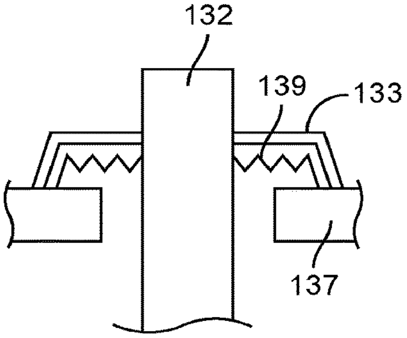
FIG. 8E shows the transducer of FIG. 8B with a blocking material placed over a bellows to inhibit formation of the deposited layer on the bellows of the transducer, in accordance with embodiments of the present invention.

FIG. 8E shows the transducer of FIG. 8B with a blocking material 133 placed over a bellows 139 to inhibit formation of the deposited layer on the bellows 139 of the transducer. The deposited layer 115 can decrease movement of the bellows, and the structure comprising blocking material 133 can be placed over the bellows to inhibit deposition of the material on the bellows. The structure comprising blocking material 133 can be placed before the output transducer 130 is placed in the transparent block 800, for example. The layer 115 deposited on the structure comprising blocking material 133 can be cut away, so as to expose the bellows, for example.

Oleophobic Coatings

In many embodiments a coupling agent such as oil can be used to couple the output transducer assembly 100 to the eardrum TM and wall of the ear canal EC. Although oil can be helpful to maintain coupling, accumulation of excessive oil can decrease performance. The inhibition of oil accumulation on vibratory components can substantially decrease autophony when the output transducer 130 is coupled to the eardrum TM with coupling structure 136, as microactuator of the output transducer 130 can be configured to allow the eardrum move in response to the user's self-generated sounds so as to decrease autophony. The formation of a puddle of oil under or over the microactuator can inhibit movement of the microactuator and contribute to autophony, and the oleophobic coating can be configured to inhibit formation of the puddle of oil so as to inhibit the autophony. An oleophobic coating can be provided on one or more locations to decrease accumulation of oil. The accumulation of oil may comprise a wetting of oil on the surfaces, and the wetting can be related to a contact angle of oil with the surface. The oleophobic coating can be provided on one or more of the microactuator, the resilient spring 140, the stiff support 120, the retention structure 110, one or more surfaces of the retention structure 110, or one or more surfaces of output transducer 130, and combinations thereof, so as to inhibit accumulation of oil.

The oleophobic coating may comprise one or more known coatings, and can be provided over the layer 115, for example. In many embodiments, the layer 115B may comprise an oleophobic coating. Alternatively, the oleophobic coating can be provided over the second layer 115B.

Figure 8F:
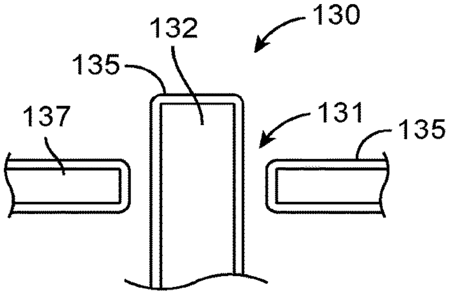
FIG. 8F shows an oleophobic layer deposited on the output transducer, in accordance with embodiments of the present invention.
Figure 9A:
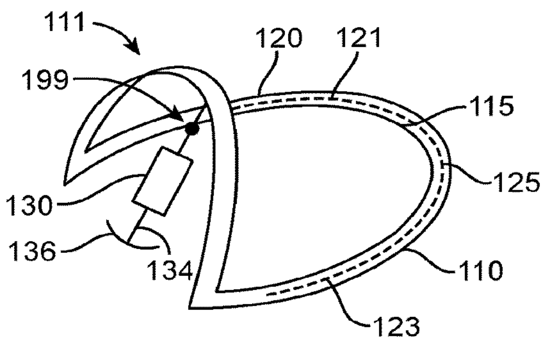
Figure 9B:
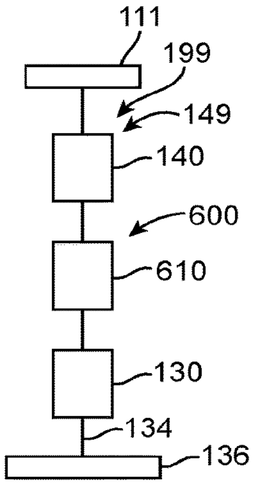

FIG. 8F shows an oleophobic layer 135 deposited on the output transducer 130. The oleophobic layer 135 can inhibit accumulation of oil on the housing. The oleophobic layer can be located on one or more of many surfaces of the output transducer assembly 100.

The bellows 139 may comprise the oleophobic layer as described herein, so as to inhibit accumulation of oil on or near the bellows, for example.

Figures 3, 4, 5, 6, 7, 8, 9, 9A:
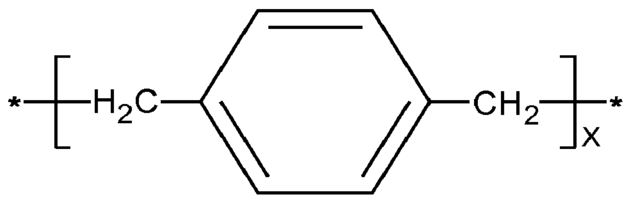

FIG. 9A shows a retention structure 110 comprising curved portion such as an arcuate portion 111 shaped to extend along a surface of the bony portion of the ear canal opposite the eardrum TM when placed. The retention structure 110 may comprise a stiff support 120, as described herein, in combination with layer 115 so as to stiffen the retention structure 110, for example. The stiff support 120 may comprise a pair of arms comprising a first arm 121, a second arm 123 opposite the first arm, and an intermediate portion 125 extending between the first arm and the second arm. Alternatively or in combination, the arcuate portion 111 may comprise the stiff support in combination with the layer 115. The arcuate portion 111 can be coupled to transducer 130 with at least one structure 199 extending between the coupling structure 136 and the arcuate portion 111 so as to couple the arcuate portion 111 to the eardrum TM with transducer located in between. The coupling of the arcuate portion 111 to the transducer and to the eardrum can provide the opposing surfaces of the eardrum and the arcuate portion 111 for the transducer to push against. The at least one structure 199 may comprise the biasing structure 149 and at least one spring 140, for example, in which the distance 149D between the lower surface of coupling structure 136 and the lower surface of retention structure 110 can be adjusted prior to placement in an unloaded configuration as described herein. The at least one structure 199 comprising the biasing structure 149 and at least one spring can support the transducer 130 and the coupling structure 136 in the unloaded free standing configuration as described herein.

The at least one structure 199 may comprise one or more of many structures a described herein to couple the transducer 130 and the coupling structure 136 to the eardrum TM, and may comprise one or more of a biasing structure, a biasing mechanism, a spring, a coil spring, a telescopic spring, a leaf spring, a telescopic joint, a locking telescopic joint, or a transducer.

Figures 3, 4, 5, 6, 7, 8, 9, 9B:
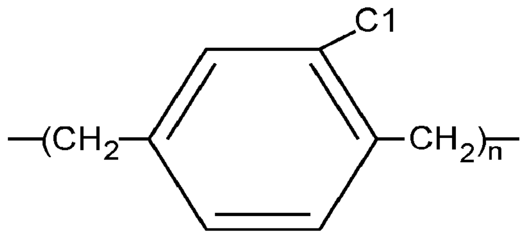
Figures 3, 4, 5, 6, 7, 8, 9, 10:
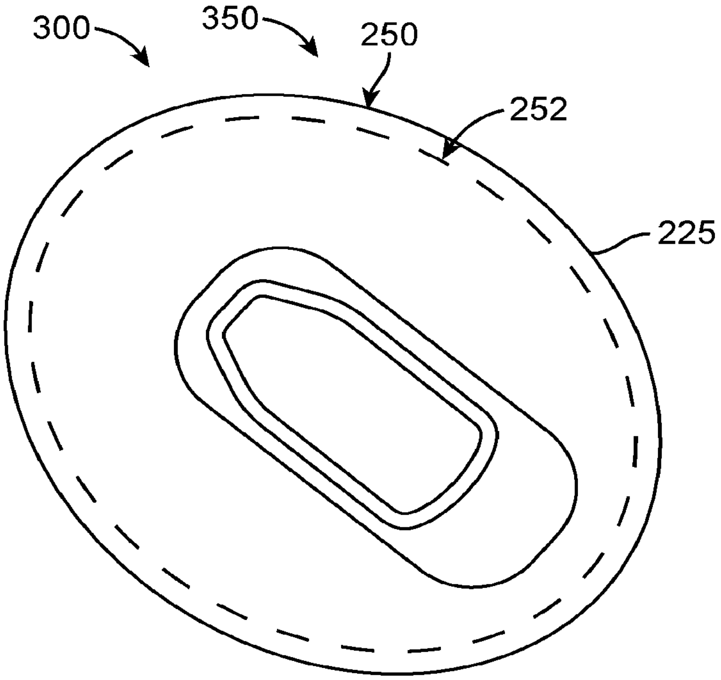

FIG. 9B shows a dynamic biasing system 600 coupled to the arcuate portion 111 and the coupling structure 136. The at least one structure 199 may comprise the at least one spring 140 and the dynamic biasing system 600. The dynamic biasing system 600 can be configured to engage the eardrum TM with coupling structure 136 when transducer 130 vibrates and configured to disengage the coupling structure 136 from the eardrum TM when transducer 130 comprises a non-vibrating configuration, for example when no substantial signal energy is transmitted to the output transducer assembly 100. The transducer 610 of biasing system 600 as described herein and may comprise rectification or other circuitry, so as to urge the output transducer 130 toward the eardrum so as to couple the output transducer to the eardrum in response to a signal transmitted to transducer 130. The transducer 610 of the dynamic biasing system 600 may comprise one or more transducers as described herein, for example one or more of a microactuator, a photostrictive transducer, a piezoelectric transducer, an electromagnetic transducer, a solenoid, a coil and magnet, or artificial muscle, for example. The transducer 610 can be coupled to the photovoltaic with wires and rectification circuitry to dynamically bias the transducer 610 in response to light energy received by the photodetector 150. Alternatively, the photostrictive material can receive electromagnetic light energy directed toward the photodetector and bias the transducer 130 in response to the light energy signal directed toward the photodetector 150 and received by the photostrictive material.

The arcuate portion provides a support for the transducer to be lifted away from the eardrum TM when the transducer 130 is not active, for example, and a support for the transducer to engage and couple to the eardrum when the transducer 130 is active, for example. The decoupling and coupling can decrease user perceived occlusion when the transducer 130 is not in use.

The at least one structure 199 coupled to the curved portion 111 can be combined with pivoting of the transducer 130 in relation to the stiff support 120 as described herein. For example, the at least one structure 199 can urge the transducer 130 toward the eardrum to couple to the eardrum, and the transducer 130 can be resiliently coupled to the support 120 with the at least one spring 140, for example a cantilever as described herein.

The transducer 130 may comprise one or more transducers as described herein, such as one or more of a microactuator, a photostrictive transducer, a piezoelectric transducer, artificial muscle, an electromagnetic transducer, a balanced armature transducer, a rod and coil transducer, a bimorph transducer, a bender, a bimorph bender, or a piezoelectric diaphragm, for example.

The at least one structure 199 may comprise one or more of many structures configured to couple the transducer to the eardrum and the arcuate portion 111. For example, the at least one structure 199 may comprise a spring or an elastic material or a combination thereof. For example the spring may comprise a leaf spring or a coil spring. The at least one structure 199 may comprise an elastic material, such as silicone elastomer configured to stretch and push the transducer toward the eardrum when the support is positioned on the eardrum. The at least one structure may comprise a viscoelastic material. Alternatively or in combination, the post 134 may comprise the at least one structure 199. The at least one structure 199 may comprise one or more of the tuning structures, for example. The at least one structure may comprise a hydraulic telescoping mechanism, for example, so as to decouple the transducer from the eardrum at low frequencies and couple the eardrum the to transducer at high frequencies. Additional structures suitable for use with at least one structure 199 in accordance with embodiments are described in U.S. Pat. App. No. 61/217,801, filed Jun. 3, 2009, entitled “Balanced Armature Device and Methods for Hearing”; and PCT/US2009/057719, filed 21 Sep. 2009, entitled “Balanced Armature Device and Methods for Hearing”, published as WO 2010/033933, the full disclosures of which have been previously incorporated herein by reference as suitable for combination in accordance with embodiments described herein.

The transducer 130 may pivot about a pivot axis to couple to the eardrum as described herein.

Figure 10A:
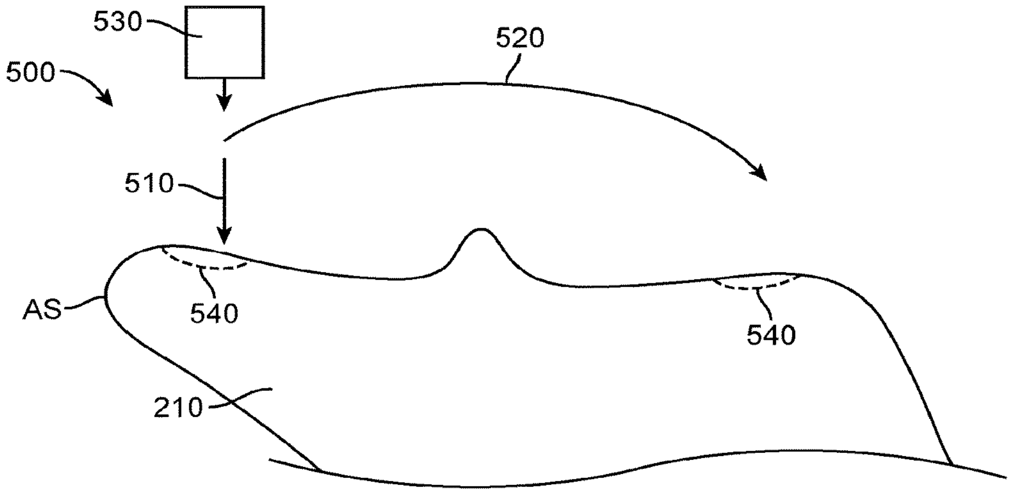
FIG. 10A shows laser sculpting of a negative mold to provide a deflection of the epithelium contacting surface of the retention structure to receive migrating epithelium, in accordance with embodiments of the present invention.

FIG. 10A shows machining such as laser sculpting 500 of a negative mold to provide a deflection of the epithelium contacting surface of the retention structure to receive migrating epithelium. The laser sculpting may comprise ablation, for example. A laser system 530 may comprise a laser to provide a source of laser energy, and a laser delivery system comprising scanning optics, for example. A leaser beam 510 can be directed to the negative mold 210 to remove material from the negative mold, such that the positive mold comprises the deflection. The laser beam can be directed in a scan patter 520 so as to ablate a predetermined profile 540 in the surface of the negative mold.

Figure 10B:
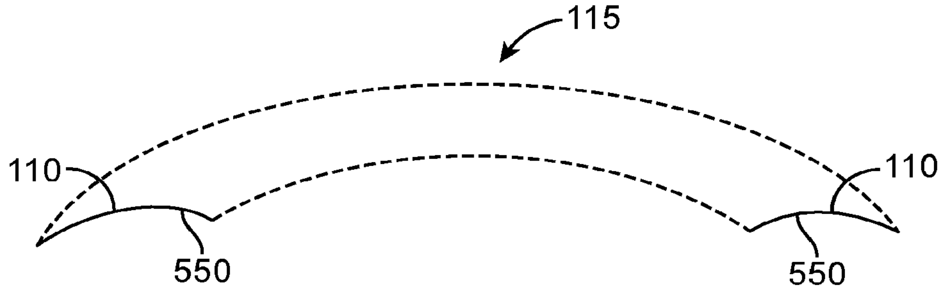
FIG. 10B shows a deflection of the epithelium contacting surface of the retention structure to receive migrating epithelium, in accordance with embodiments of the present invention.

FIG. 10B shows one or more deflections 550 of the epithelium contacting surface of the retention structure to receive migrating epithelium. The one or more deflections 550 can be shaped with a curved edge such that epithelium advancing toward the edge passes under the edge. The retention structure 110 may comprise an annular retention structure having an inner edge oriented toward the umbo and an outer edge oriented toward the canal wall. The inner edge may comprise the one or more deflections 550 to receive the migrating epithelium.

Figure 10C:
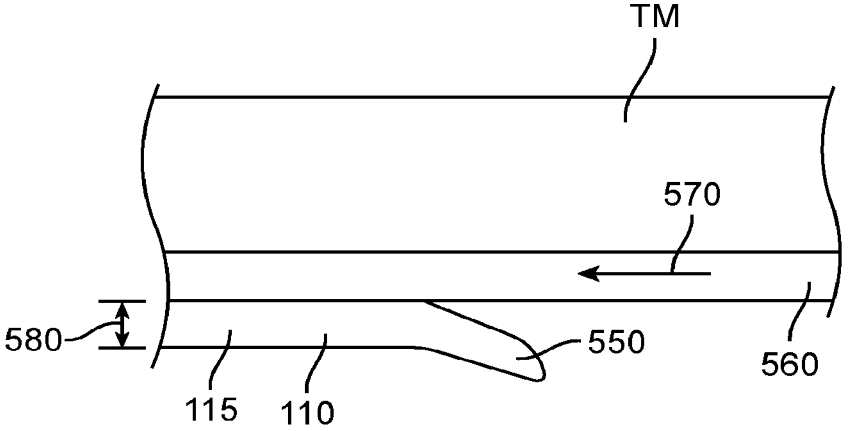
FIG. 10C shows a epithelium migrating under the deflection of FIG. 10B, in accordance with embodiments of the present invention.
Figure 11:
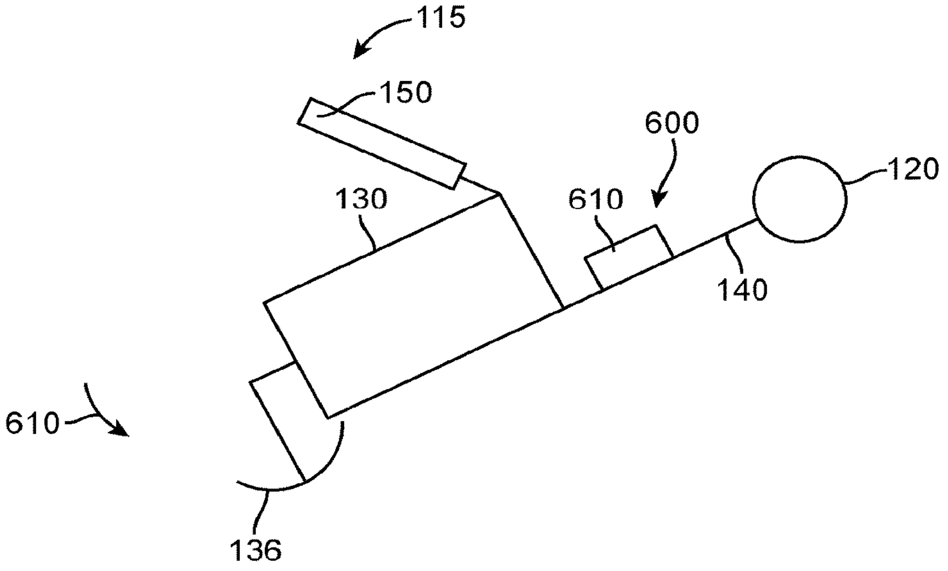
Figure 12:
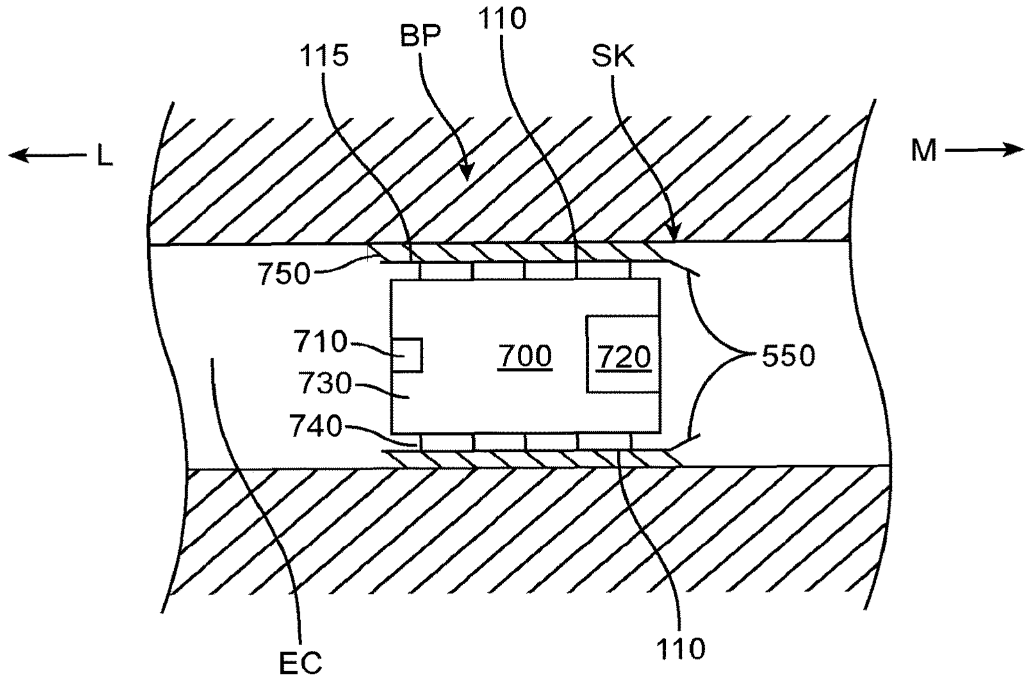

FIG. 10C shows a epithelium 560 migrating under the one or more deflections 550 of FIG. 10B. The retention structure may comprise an annular structure having an aperture positionable over the umbo. In many patients, the epithelium can migrate in a direction 570 outward from the umbo along the surface of the eardrum toward the eardrum annulus and canal wall. The epithelium can migrate from the eardrum annulus to the canal wall, and subsequently in a direction 570 along the canal wall toward the opening to the ear canal. The deflection 550 may comprise a portion of the retention structure having a thickness similar to a majority of the retention structure.

In many embodiments, the thickness of the retention structure 110 is within a range from about 5 to about 50 um, such that the thickness of the retention structure is approximates to the thickness of the epithelium. The epithelium on the umbo can be about 15 um thick, for example, and can be thicker on the ear canal, for example about 50 to 100 um thick. The one or more deflections 550 can provide sufficient clearance to pass the epithelium under the edge of the deflection 550. The amount of deflection may comprise a distance 580 corresponding to the profile of material removed from the negative mold, for example the ablation profile. The distance 580 can be proportional to the thickness of the epithelium at the location of placement, and the distance 580 can be at least as thick as the epithelium. The distance 580 can be at least about 15 um, for example at least about 50 um, and in many embodiments 100 um or more. A similar deflection can be provided by depositing material on the positive mold, for example as an alternative to removal of material from the negative mold.

Figures 3, 4, 5, 6, 7, 8, 9, 10, 11:
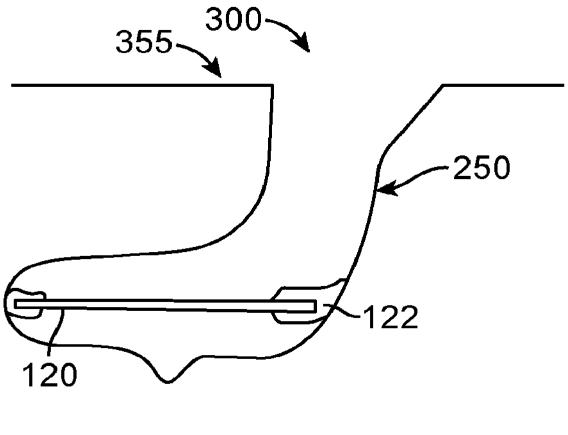

FIG. 11 shows a dynamic biasing system 600 comprising a transducer 620 configured to deflect the output transducer 130 toward the eardrum so as to couple the output transducer to the eardrum. The dynamic biasing system 600 comprising the transducer 620 can move one or more of the transducer 130, the arm 134 or the structure 136, or combinations thereof, toward the eardrum with a movement 610. The at least one spring 140 can be coupled to the dynamic biasing system to allow movement of the coupling structure 136. The biasing structure 149 of the at least one spring can be coupled to the at least one spring 140 as described herein. The dynamic biasing system 600 comprising the transducer 620 may comprise one or more of many known transducers, such as one or more of a piezoelectric transducer, a coil and magnet transducer, a photostrictive material, artificial muscle, or combinations thereof. The transducer 620 can be configured to couple the transducer to the eardrum when the transducer 130 transmits sound to the user. In many embodiments, the dynamic biasing system 600 comprising the transducer 620 is configured to couple to the eardrum in response to the signal transmitted to transducer 130. For example, dynamic biasing system 600 comprising the transducer 620 may comprise rectification circuitry to provide a voltage to the transducer in response to an AC signal to transducer 130. The transducer 620 may comprise photostrictive material configured to provide movement 610 when a light beam is transmitted to photodetector 150 and a portion of the light beam is absorbed by the photostrictive material. The transducer 620 may comprise artificial muscle, commercially available from Artificial Muscle, Inc., of Sunnyvale, Calif.

Figures 3, 4, 5, 6, 7, 8, 9, 10, 11, 12:
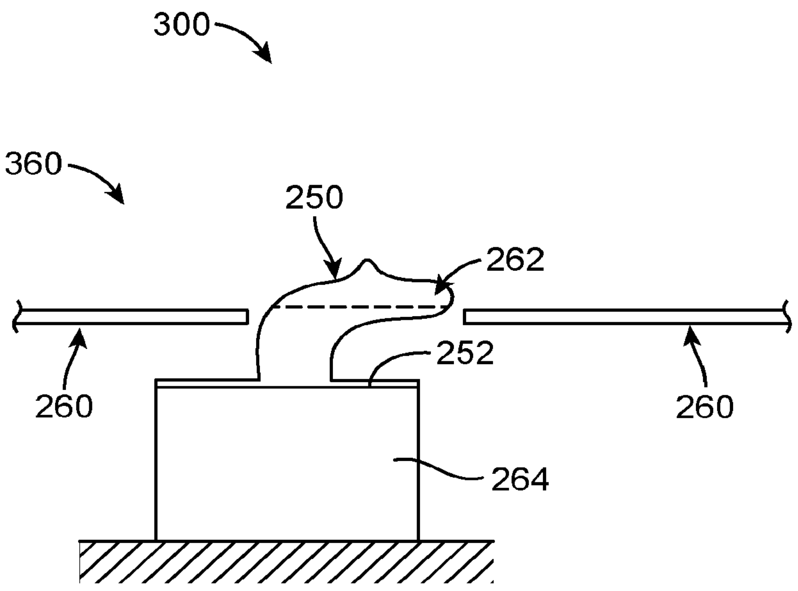
Figure 4:
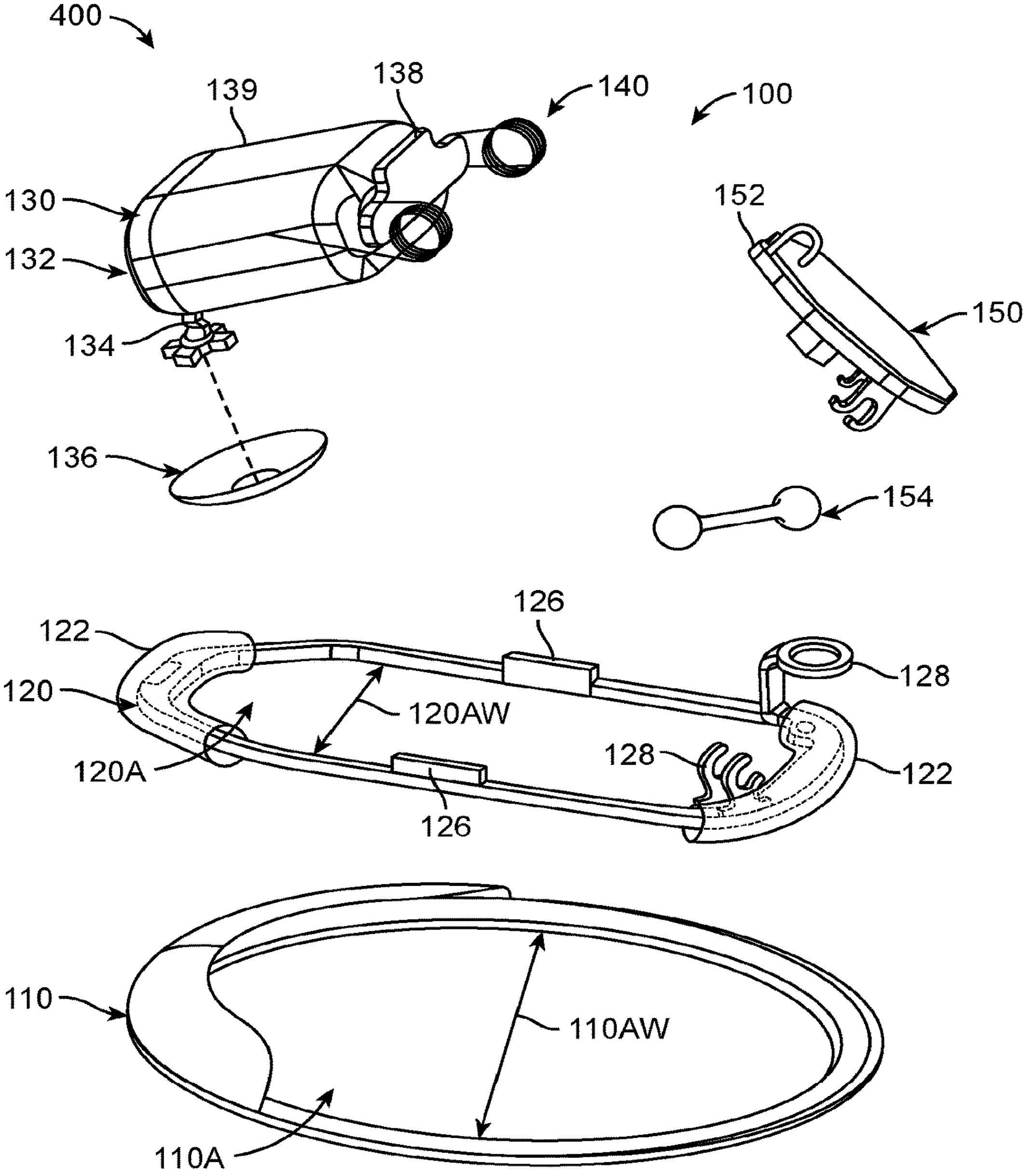

FIG. 12 shows a retention structure 110 comprising layer 115 configured for placement in the middle ear supporting an acoustic hearing aid 700. The retention structure 110 comprising layer 115 can be manufactured as described herein and configured for placement in deep in the ear canal, so as to couple to the bony portion BP of the ear canal. The retention structure 110 may comprise a molded tubular structure having the shape of the ear canal, and can be manufactured from cut sections as described herein.

The retention structure 110 comprises one or more deflections 550 as described herein. The retention structure 110 may comprise a thickness within a range from about 1 um to about 100 um as described herein, for example within a range from about 5 um to about 50 um. The thickness of the Parylene™ retention structure within this range can be sufficiently resilient so as to support the retention structure 110 and to deflect when inserted or the patient chews, for example. As the epithelium covering the bony portion of the ear canal may comprise a thickness within a range from about 50 um to about 100 um, the retention structure 110 may comprise a thickness less than the thickness of the epithelium.

The one or more deflections 550 can be oriented toward the eardrum of retention structure 110 and shaped so as to receive epithelium migrating outward toward the ear canal opening. The one or more deflections deflect away from the epithelium toward the source of epithelium so as to inhibit epithelial growth over an edge of the retention structure 550. The eardrum is located medially M to the retention structure 110 and the ear canal opening is located laterally L to the retention structure 110. The lateral side 110 may comprise deflections similar to the one or more deflections 550 to facilitate removal of the retention structure 110.

The retention structure 110 can be configured in one or more ways as described herein so as to retain the hearing aid 700 in the ear canal. The retention structure 110 can be place in the ear canal without lubrication and can remain in the ear canal without application of a coupling agent such as an oil. Alternatively, the user can apply oil 750 to the ear canal, and the oil 750 can pass between the retention structure 110 and the ear canal EC. The presence of oil between the skin SK and the retention structure 110 can couple the retention structure to the skin SK, and can reduce adhesion of the skin to the retention structure 110. The oil can facilitate removal and can decrease adhesion of the skin SK to the retention structure, such that the retention structure 110 can be removed from the ear canal without tearing of the skin SK, for example. In many embodiments, the retention structure can remain placed in the ear canal EC for one or more months, for example about three or more months.

The acoustic hearing aid 700 may comprise one or more of many components to decrease occlusion and feedback, for example. The hearing aid 700 may comprise a microphone 710 on the temporal side T of the device, such that the microphone 710 can be positioned deep in the ear canal to provide sound localization. The hearing aid 700 may comprise and acoustic speaker 720 to vibrate the eardrum TM. The hearing aid 700 can decrease sound transmission from the acoustic speaker 720 to the microphone 710 in one or more of many ways. The molded fit of the retention structure 110 to the ear canal can inhibit the formation of sound conduction pathways such as gaps that can transmit sound from the acoustic speaker to the microphone. The hearing aid 700 can be configured further to inhibit sound transmission from the acoustic speaker to the microphone, for example by substantially inhibiting air flow from the medial side M to the lateral side L with a casing 730 and a support material 740 to couple the retention structure 110 to the casing 730. The casing 730 may comprise a rigid material, and support material 740 may comprise one or more of a compressible or an elastic material, such as a foam or elastomer or a combination thereof. The deep placement on the bony portion BP can inhibit user perceived occlusion when the hearing aid 700 occludes the ear canal and blocks sound transmission from the medial side M to the lateral side L.

The acoustic hearing aid 700 may comprise one or more components of a commercially available hearing aid, such as the Lyric™, commercially available from InSound Medical, Inc. (website www.lyrichearing.com), or a similar known hearing aid commercially available from Starkey, for example. The Lyric™ hearing aid can be combined with the retention structure 110 in accordance with embodiments as described herein. The hearing aid 700 can be placed deep into the bony portion of the ear canal so that the receiver resides approximately 4 mm from the eardrum, and the microphone can be 4 mm or more from the opening of the ear canal. This placement deep in the ear canal provides a number of sound quality benefits.

The retention structure 110 comprising layer 115 can be well suited to fit many complex ear anatomies, including ear canals that are one or more of narrow, or short as compared to a population of patient and combinations thereof. Additional anatomies the retention structure 110 comprising layer 110 is well suited to fit include a significant step-up in the canal floor, extreme v-shaped canal, or a large bulge in the canal, and combinations thereof. These complex ear anatomies can be fit comfortably so as to decrease the chance of discomfort to the user. The retention structure 115 comprising layer 110 can provide a lateral seal of the ear canal so as to inhibit feedback and decrease occlusion.

The placement deep in the ear canal can provide improved directionality and localization (ability to tell where sounds are coming from). The hearing aid 700 placement deep in the ear canal can allows the pinna (outer part of the ear) to interact naturally with incoming sounds. The acoustic transformations produced by the pinna as sound enters the ear canal contribute to the ability to accurately determine where sounds are coming from in the environment, similar to assembly 100.

The hearing aid 700 can provide decreased user perceived occlusion and decreased feedback. As the receiver sits closer to the eardrum than with traditional hearing aids, less output can be used to accommodate hearing loss, which can decrease feedback.

The hearing aid 700 can reside substantially in the hard-walled bony portion BP of the ear canal, so as to decrease movement of the device. As the retention structure 110 can be molded, the fit between the ear canal and the device can inhibit sound transmission between the retention structure 110 and the ear canal so to inhibit feedback. The placement deep in the ear canal can allow the hearing aid 700 to be configured so as to inhibit sound transmission from the receiver end toward the microphone, similar to the Lyric™.

The hearing aid 700 can be retained anchored in the ear canal so as to inhibit slippage and also in a manner that fits irregular shapes and contours of various ear canals, as the retention structure 110 can be molded. As the retention structure 110 comprises a resilient structure capable of changing shape, the fit to the ear canal can be maintained when the ear changes shape during chewing and talking. This can prevent slippage of the hearing aid 110 and inhibit sound leakage and feedback.

Deep canal fitting of hearing aid 700 can result in an increase in sound pressure level at the eardrum as compared with a conventional hearing aid. This increase can be up to 15 dB in the high frequencies, and can caused by a combination of reduced residual ear canal volume between the receiver and the eardrum and the microphone location deeper in the ear canal allowing for pinna effects.

Security of fit and retention of the molded retention structure 110 can provide improved patient comfort with hearing aid 700.

EXPERIMENTAL

Output transducer assemblies as described herein have been placed in many ears of many users to evaluate comfort, sound quality and retention. In many embodiments, the retention structure comprises a Parylene™ coating having a thickness of about 20 um.

The retention structure having this thickness can deform when advanced along the ear canal of the user and can expand to the wide profile configuration comprising the shape of the ear canal based on the vapor deposition to the positive mold as described herein. The resistance to deflection can be determined with concentrated loads on opposite sides of the retention structure similar to the inward deflection provided by ear canal, for example.

The resistance to deflection can be determined based on material properties and dimensions of the retention structure 110 as described herein. Non-limiting examples of numerical calculations to determine the approximate resistance to deflection include calculations for the following two embodiments:

Embodiment 1. The retention structure 110 comprises a flat ribbon 2 mm high and 18 um thick. The radius is 5 mm and the elastic modulus is about 1 GPa. The resistance to deflection of the stiff retention structure is about 5 N/m. In many embodiments, a lower resistance to deflection can be used, for example about 1 N/m.

Embodiment 2. The retention structure comprises a c channel 2 mm high (with a radius of 1 mm) and 18 um thick. The overall radius is 5 mm and the elastic modulus is about 1 GPa. The resistance to deflection of the stiff retention structure is about 27,000 N/m. As the asymmetric shape of the anatomy of the ear canal may result in varying resistance to deflection along the perimeter of the retention structure, local areas of the retention structure may absorb a substantial majority of the deflection, such that a resistance to deflection of about 10,000 N/m may be appropriate. The resistance to deflection can be within a range from about 1 N/m to about 10,000 N/m, for example.

In many embodiments, the eardrum comprises a resistance to deflection of about 250 N/mm. In some embodiments, it can be helpful to provide the retention structure with a resistance to deflection within a range from about 250 N/m to about 10,000 N/m, for example.

While the exemplary embodiments have been described in some detail, by way of example and for clarity of understanding, those of skill in the art will recognize that a variety of modifications, adaptations, and changes may be employed. Hence, the scope of the present invention shall be limited solely by the appended claims.

What is claimed is:

1. A method of making a support for placement on a tissue of a user, the method comprising:
- depositing a material of a vapor on a substrate to form the support, the substrate having a shape profile corresponding to the tissue and wherein the support is separated from the substrate,
- wherein the shape profile of the substrate corresponds to a shape profile of a tissue surface and wherein the shape profile comprises a portion having a deflection away from the shape profile of the tissue surface so as to provide a deflection in the support away from a surface of the tissue.

2. The method of claim 1, wherein the material is polymerized on the substrate to form the support having the shape profile.

3. The method of claim 2, wherein a solid layer of the material forms having the shape profile and wherein the support comprises the solid layer when separated from the substrate.

4. The method of claim 3, wherein a release agent is disposed on the substrate between the substrate and the support when the vapor is deposited on the release agent to form the support.

5. The method of claim 4, wherein the release agent comprises one or more of one or more of PEG, a hydrophilic coating, a surface treatment such as corona discharge, a surfactant, a wax, hydrophilic wax, or petroleum jelly.

6. The method of claim 4, wherein the release agent comprises a solid when the vapor is deposited at an ambient temperature and wherein the release agent is heated so as to comprise a liquid when the support is separated from the substrate.

7. The method of claim 4, wherein the release agent has a first surface oriented toward the substrate and in contact with the substrate and a second surface oriented away from the substrate to contact the support, the second surface smoother than the first surface.

8. The method of claim 4, wherein the release agent comprises one or more of a surfactant or a water soluble polymer to release the solid layer from the substrate with water.

9. The method of claim 1, wherein the material of the vapor comprises monomer molecules having aromatic rings and wherein the monomer molecules are polymerized to form a polymer on the substrate having the aromatic rings.

10. The method of claim 1, wherein the material of the vapor comprises one or more of poly(p-xylylene) based monomer or poly(p-xylylene) based polymers and the slip agent comprises petroleum jelly.

11. The method of claim 1, wherein the material of the vapor comprises one or more of PVA or PVA-H.

12. The method of claim 1, wherein the material of the vapor is deposited with one or more of thermal deposition, radio frequency deposition, or plasma deposition.

13. The method of claim 1, wherein the tissue surface comprises an epithelial surface and wherein the deflection is configured to extend away from the epithelial surface when the support is placed and wherein the deflection is oriented on the support so as to receive the advancing epithelium under the deflection.

14. The method of claim 1, wherein the substrate comprises a portion of an optically transmissive positive mold of the tissue and wherein components of a hearing device are placed in the mold with visualization of the components through the optically transmissive positive mold.

15. The method of claim 14, wherein the tissue comprises at least a portion of an ear canal or a tympanic membrane of a user, the method further comprising:

making a negative mold of the at least the portion or the tympanic membrane;

coating the negative mold with an optically transmissive material;

curing the coating;

placing the cured coating in a container comprising an optically transmissive flowable material; and curing the optically transmissive flowable material to form a positive mold, wherein the cured coating inhibits deformation of the negative mold when the optically transmissive flowable material is cured.

16. The method of claim 1, wherein the support comprises a first layer of the polymerizable material and a second layer of the polymerizable material and wherein components of a hearing device are situated between the first layer and the second layer.

17. The method of claim 16, further comprising placing components of the hearing device on the first layer and depositing the second layer on the components placed on the first layer.

18. The method of claim 16, further placing an oleophobic coating on one or more of the first transducer or the retention structure.

19. The method of claim 1, wherein the support comprises a retention structure shaped for placement in an ear canal of a user, further comprising placing a part comprising at least one spring, a support component comprising arms and an intermediate section extending between the arms and wherein the arms are affixed to the retention structure.

20. The method of claim 19, wherein the vapor is deposited on the part to affix the part to the retention structure.

21. The method of claim 19, wherein a projection extends from the part to place the retention structure in the ear canal of the user.

22. The method of claim 1, wherein the support comprises a retention structure shaped for placement in an ear canal of a user and wherein the support is cut along a portion toward an eardrum and a portion toward an opening of the ear canal so as to define an aperture to couple a transducer to an eardrum of the user.

23. The method of claim 22, wherein the portion toward the eardrum corresponds to an anterior sulcus of the ear canal and wherein the portion toward the opening of the ear canal corresponding to the bony part of the ear canal.

24. The method of claim 22, wherein the portion toward the eardrum is cut to limit insertion depth such that the portion toward the eardrum can be viewed by a clinician when placed.

* * * * *